(12) United States Patent
Walavalkar et al.

(10) Patent No.: US 9,913,603 B2
(45) Date of Patent: Mar. 13, 2018

(54) REFLOWED GOLD NANOSTRUCTURES FOR SURFACE ENHANCED RAMAN SPECTROSCOPY

(71) Applicants: CALIFORNIA INSTITUTE OF TECHNOLOGY, Pasadena, CA (US); THE REGENTS OF THE UNIVERSITY OF CALIFORNIA, Oakland, CA (US); UNIVERSITY OF SOUTHERN CALIFORNIA, Los Angeles, CA (US)

(72) Inventors: Sameer Walavalkar, Studio City, CA (US); Chieh-feng Chang, Pasadena, CA (US); Axel Scherer, Barnard, VT (US); Brandon Marin, San Diego, CA (US); Scott E. Fraser, Glendale, CA (US); Andrea R. Tao, La Jolla, CA (US)

(73) Assignees: CALIFORNIA INSTITUTE OF TECHNOLOGY, Pasadena, CA (US); THE REGENTS OF THE UNIVERSITY OF CALIFORNIA, Oakland, CA (US); UNIVERSITY OF SOUTHERN CALIFORNIA, Los Angeleles, CA (US)

( * ) Notice: Subject to any disclaimer, the term of this patent is extended or adjusted under 35 U.S.C. 154(b) by 344 days.

(21) Appl. No.: 14/621,286

(22) Filed: Feb. 12, 2015

(65) Prior Publication Data
US 2015/0223739 A1      Aug. 13, 2015

Related U.S. Application Data

(60) Provisional application No. 61/938,784, filed on Feb. 12, 2014, provisional application No. 62/046,628, (Continued)

(51) Int. Cl.
*G01N 21/65* (2006.01)
*G01N 33/18* (2006.01)
(Continued)

(52) U.S. Cl.
CPC .......... *A61B 5/1459* (2013.01); *A61B 5/0075* (2013.01); *A61B 5/14735* (2013.01);
(Continued)

(58) Field of Classification Search
CPC .............................. G01N 21/658; B82Y 40/00
See application file for complete search history.

(56) References Cited

U.S. PATENT DOCUMENTS 4,674,878 A * 6/1987 Vo-Dinh .............. G01N 21/658
356/301
6,259,937 B1 * 7/2001 Schulman .......... A61B 5/14532
600/300

(Continued)

FOREIGN PATENT DOCUMENTS

EP      2653530 A2    10/2013
JP    2004-286570 A    10/2004
(Continued)

OTHER PUBLICATIONS

Walavalkar, S et al. "Scalable Method for the Fabrication and Testing of Glass-Filled, Three-Dimensionally Sculpted Extraordinary Transmission Apertures." Nano Lett. vol. 14 (1), pp. 311-317 2014.

(Continued)

*Primary Examiner* — Dominic J Bologna
(74) *Attorney, Agent, or Firm* — Steinfl + Bruno LLP

(57) ABSTRACT

Methods and systems for nanopillar sensors are described. Nanopillars can be defined on a substrate, and metal deposited on the nanopillars. A thermal treatment can reflow the metal on the nanopillars forming metallic bulbs on the top
(Continued)

end of the nanopillars. These structures can have enhanced optical detection when functionalized with biological agents, or can detect gases, particles and liquids through interaction with the metal layer on the nanopillars.

41 Claims, 34 Drawing Sheets

Related U.S. Application Data filed on Sep. 5, 2014, provisional application No. 62/065,224, filed on Oct. 17, 2014, provisional application No. 62/049,256, filed on Sep. 11, 2014.

(51) Int. Cl.
| | | |
|---|---|---|
| *G01N 33/483* | (2006.01) | |
| *G01N 33/00* | (2006.01) | |
| *A61B 5/1459* | (2006.01) | |
| *H01L 27/146* | (2006.01) | |
| *A61B 5/1473* | (2006.01) | |
| *A61B 5/07* | (2006.01) | |
| *A61B 5/00* | (2006.01) | |
| *B82Y 40/00* | (2011.01) | |
| *B82Y 30/00* | (2011.01) | |

(52) U.S. Cl.
CPC ........... *A61B 5/686* (2013.01); *G01N 21/658* (2013.01); *H01L 27/14698* (2013.01); *A61B 5/076* (2013.01); *A61B 5/6848* (2013.01); *A61B 2562/0233* (2013.01); *A61B 2562/0285* (2013.01); *A61B 2562/12* (2013.01); *B82Y 30/00* (2013.01); *B82Y 40/00* (2013.01)

(56) References Cited

U.S. PATENT DOCUMENTS

| | | | | |
|---|---|---|---|---|
| 7,951,299 | B2* | 5/2011 | Hossein-Zadeh .. | G02B 6/12007 216/2 |
| 8,080,468 | B2 | 12/2011 | Scherer et al. | |
| 2007/0243519 | A1 | 10/2007 | Hess et al. | |
| 2008/0032420 | A1 | 2/2008 | Lambert et al. | |
| 2008/0119832 | A1* | 5/2008 | Cronin ................ | A61B 5/0059 606/15 |
| 2009/0131245 | A1* | 5/2009 | Esconjauregui ......... | B01J 23/75 502/100 |
| 2009/0215050 | A1 | 8/2009 | Jenison | |
| 2010/0066346 | A1* | 3/2010 | Zhang ................. | B81C 1/00166 324/71.1 |
| 2010/0265680 | A1* | 10/2010 | Tai ........................ | A61B 5/0031 361/760 |
| 2011/0053794 | A1* | 3/2011 | Zhang ................... | B01J 19/0046 506/9 |
| 2011/0116089 | A1* | 5/2011 | Schmidt ............... | G01N 21/658 356/301 |
| 2011/0128536 | A1* | 6/2011 | Bond ..................... | B82Y 20/00 356/301 |
| 2012/0142119 | A1 | 6/2012 | Zhang et al. | |
| 2013/0090536 | A1 | 4/2013 | Milner et al. | |
| 2013/0153860 | A1* | 6/2013 | Kim ..................... | H01L 51/0002 257/14 |
| 2013/0236881 | A1* | 9/2013 | Spatz ................... | B81C 1/00031 435/5 |
| 2014/0011013 | A1* | 1/2014 | Jin ........................ | B05D 5/08 428/297.4 |
| 2014/0024131 | A1 | 1/2014 | Kim et al. | |
| 2014/0199778 | A1 | 7/2014 | Wu et al. | |
| 2015/0173656 | A1* | 6/2015 | Barcelo ................ | A61B 5/1459 600/341 |

FOREIGN PATENT DOCUMENTS

| | | |
|---|---|---|
| WO | 2012/024006 A2 | 2/2012 |
| WO | 2013/158114 A1 | 10/2013 |
| WO | 2014/021809 A1 | 2/2014 |

OTHER PUBLICATIONS

Barman, I. et al. "Accurate Spectroscopic Calibration for Noninvasive Glucose Monitoring by Modeling the Physiological Glucose Dynamics." Anal. Chem. 82, pp. 6104-6114. 2010.
Henry, M.D., et al. "Alumina etch masks for the fabrication of high-aspect-ratio silicon micropillars and nanopillars." Nanotechnology, vol. 20, 255305, pp. 1-4. 2009.
Walavalkar, S.S., et al. "Controllable deformation of silicon nanowires with strain up to 24%." Journal of Applied Physics, vol. 107, 124314, pp. 1-5. 2010.
Walavalkar, S.S., et al. "Tunable visible and near-IR emission from sub-10 nm etched single crystal Si nanopillars." Nano Letters, 2010. vol. 10, p. 4423-4428.
Walavalkar, S.S., et al. "Size tunable visible and near-infrared photoluminescence from vertically etched silicon quantum dots." Applied Physics Letters, 2011.vol. 98, pp. 153114-153117.
Walavalkar, S.S., et al. "Three-dimensional etching of silicon for the fabrication of low-dimensional and suspended devices." Nanoscale, 2013. vol. 5, pp. 927-931.
Walavalkar, S.S., et al. "Coulomb blockade in vertical, bandgap engineered silicon nanopillars." Applied Physics Letters, 2013. vol. 102, 183101, pp. 1-3.
Walavalkar, S.S., et al. "Scalable method for the fabrication and testing of glass-filled, three-dimensionally sculpted extraordinary transmission apertures." Nano letters, 2014. vol. 14, pp. 311-317.
Wulfkuhle, J.D., et al. "Proteomic applications for the early detection of cancer." Nature reviews. Cancer, 2003.vol. 3, pp. 267-275.
Dalby, T. et al. "Laboratory diagnosis of pertussis: agglutination is not suitable." Respirology (Carlton, Vic.), 2011. vol. 16, pp. 1160-1162.
Campbell, H., et al., "Oral fluid testing for pertussis, England and Wales, Jun. 2007-Aug. 2009." Emerging Infectious Diseases, 2014. vol. 20, pp. 968-975.
Rasooly, A., et al. "Development of biosensors for cancer clinical testing." Biosensors & Bioelectronics, 2006. vol. 21, pp. 1851-1858.
Soper, S.A., et al. "Point-of-care biosensor systems for cancer diagnostics/prognostics." Biosensors & Bioelectronics, 2006. vol. 21, pp. 1932-1942.
Wang, J., "Electrochemical biosensors: towards point-of-care cancer diagnostics." Biosensors & Bioelectronics, 2006.vol. 21: pp. 1887-1892.
Wei, F., et al. "Electrochemical sensor for multiplex biomarkers detection." Clinical Cancer Research, 2009. vol. 15: pp. 4446-4452.
Tothill, I.E. "Biosensors for cancer markers diagnosis." Seminars in Cell & Developmental Biology, 2009. vol. 20: pp. 55-62.
Lozano, R., et al. "Global and regional mortality from 235 causes of death for 20 age groups in 1990 and 2010: a systematic analysis for the Global Burden of Disease Study 2010." Lancet, 2012. vol. 380, pp. 2095-2128.
Howlader N, N.A., et al. SEER Cancer Statistics Review, 1975-2011, 2014: National Cancer Institute. Bethesda, MD.
Shah, F.D., et al., "A review on salivary genomics and proteomics biomarkers in oral cancer." Indian Journal of Clinical Biochemistry : IJCB, 2011. vol. 26: pp. 326-334.
Punyani, S.R. et al. "Salivary level of interleukin-8 in oral precancer and oral squamous cell carcinoma." Clinical Oral Investigations, 2013. vol. 17, pp. 517-524.
Cheng, Y.S.L., et al. "A review of research on salivary biomarkers for oral cancer detection." Clinical and Translational Medicine, 2014.vol. 3,10 pg.
Tondella, M.L., et al., "International Bordetella pertussis assay standardization and harmonization meeting report. Centers for Disease Control and Prevention, Atlanta, Georgia, United States, Jul. 19-20, 2007." Vaccine, 2009. vol. 27: pp. 803-814.

(56) References Cited

OTHER PUBLICATIONS

Melvin, J.A., et al. "Bordetella pertussis pathogenesis: current and future challenges." Nature Reviews. Microbiology, 2014. vol. 12: pp. 274-288.
Atwell, J.E., et al. "Nonmedical vaccine exemptions and pertussis in California, 2010." Pediatrics, 2013.vol. 132: pp. 624-630.
Locht, C. "Molecular aspects of Bordetella pertussis pathogenesis, in International Microbiology." vol. 2, pp. 137-144. 1999.
De Gouw, D., et al. "Pertussis: a matter of immune modulation." FEMS microbiology reviews, 2011. vol. 35: pp. 441-474.
Shembekar, V.R., et al. "A protecting group for carboxylic acids that can be photolyzed by visible light." Biochemistry, 2005. vol. 44: pp. 7107-7114.
Kumar, S., et al. "Directional conjugation of antibodies to nanoparticles for synthesis of multiplexed optical contrast agents with both delivery and targeting moieties." Nature protocols, 2008. vol. 3: pp. 314-320.
Li, Y., et al. "Salivary transcriptome diagnostics for oral cancer detection." Clinical Cancer Research: an official journal of the American Association for Cancer Research. 2004. vol. 10: p. 8442-8450.
Sung, H.J., et al. "Inhibition of human neutrophil activity by an RNA aptamer bound to interleukin-8." Biomaterials, 2014. vol. 35: pp. 578-589.
Ellington, A.D. et al. "In vitro selection of RNA molecules that bind specific ligands." Nature, 1990. vol. 346: pp. 818-822.
Hamaguchi, N., et al. "Aptamer beacons for the direct detection of proteins." Analytical Biochemistry, 2001. vol. 294, pp. 126-131.
Roberts, R.W., et al. "RNA-peptide fusions for the in vitro selection of peptides and proteins." Proceedings of the National Academy of Sciences, 1997. vol. 94: pp. 12297-12302.
Takahashi, T.T., et al. "mRNA display: ligand discovery, interaction analysis and beyond." Trends in Biochemical Sciences, 2003.vol. 28: pp. 159-165.
Wilson, D.S., et al. "The use of mRNA display to select high-affinity protein-binding peptides." Proceedings of the National Academy of Sciences of the United States of America, 2001. vol. 98: pp. 3750-3755.
Aoyama, T., et al. "Comparison of blood-free medium (cyclodextrin solid medium) with Bordet-Gengou medium for clinical isolation of Bordetella pertussis." J. Clin. Microbiol., 1986. vol. 23: pp. 1046-1048.
Yang, X., et al. "Construction and selection of bead-bound combinatorial oligonucleoside phosphorothioate and phosphorodithioate aptamer libraries designed for rapid PCR-based sequencing." Nucleic Acids Research, 2002. vol. 30: e132, 8 pgs.
Goldman, W.E., et al. "Detection, isolation, and analysis of a released Bordetella pertussis product toxic to cultured tracheal cells." Infect. Immun., 1982. vol. 36: pp. 782-794.
Rosenthal, R.S., et al., "Major fragment of soluble peptidoglycan released from growing Bordetella pertussis is tracheal cytotoxin." Infect. Immun., 1987. vol. 55: pp. 2117-2120.
Leavitt, A.J., et al. "Chemical reactive studies of hydrogen sulfide on Au(111)." Surface Science, 1994. vol. 314: pp. 22-33.
International Search Report dated May 26, 2015 for PCT/US2015/015693 filed on Feb. 12, 2015 in the name of California Institute of Technology.
Written Opinion dated May 26, 2015 for PCT/US2015/015693 filed on Feb. 12, 2015 in the name of California Institute of Technology.
International Search Report dated May 28, 2015 for PCT/US2015/015698 filed on Feb. 12, 2015 in the name of California Institute of Technology.
Written Opinion dated May 28, 2015 for PCT/US2015/015698 filed on Feb. 12, 2015 in the name of California Institute of Technology.
International Search Report dated May 28, 2015 for PCT/US2015/015701 filed on Feb. 12, 2015 in the name of California Institute of Technology.
Written Opinion dated May 28, 2015 for PCT/US2015/015701 filed on Feb. 12, 2015 in the name of California Institute of Technology.
International Search Report dated May 29, 2015 for PCT/US2015/015705 filed on Feb. 12, 2015 in the name of California Institute of Technology.
Written Opinion dated May 29, 2015 for PCT/US2015/015705 filed on Feb. 12, 2015 in the name of California Institute of Technology.

* cited by examiner

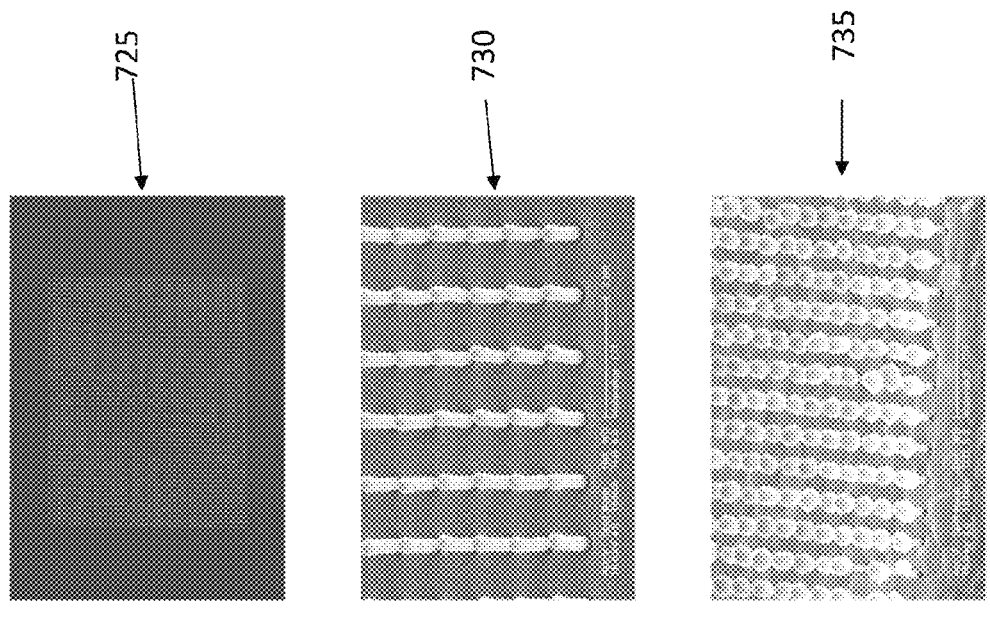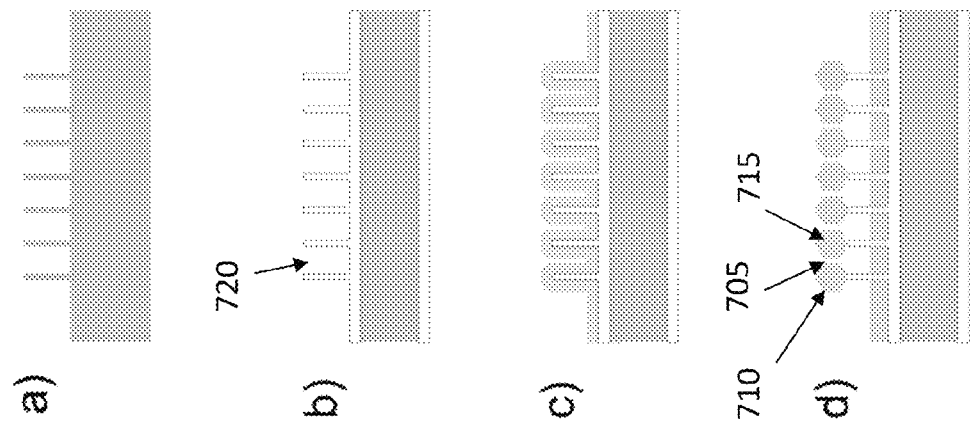
FIG. 7

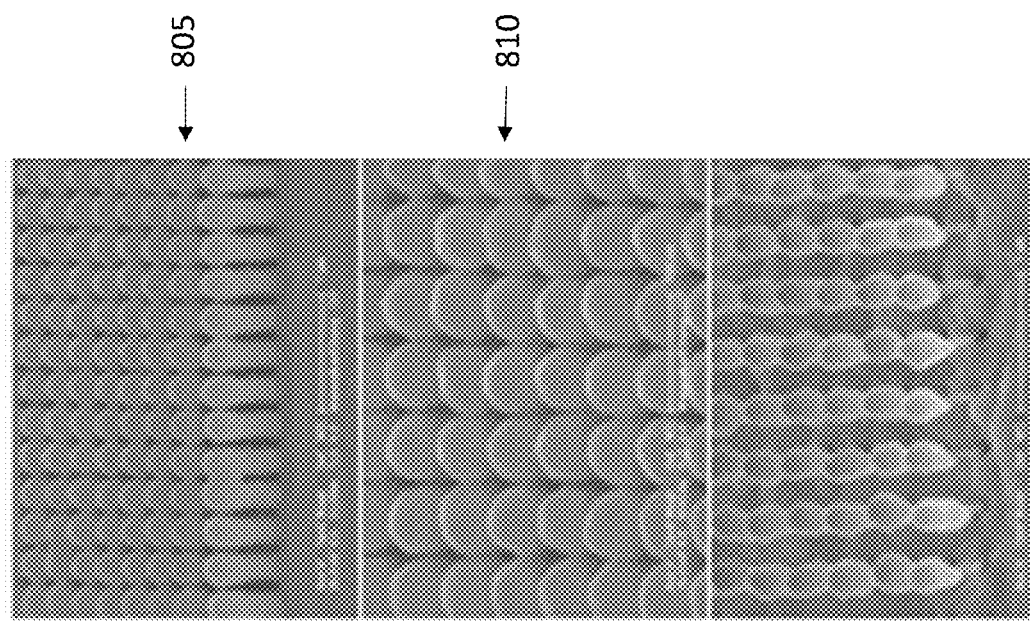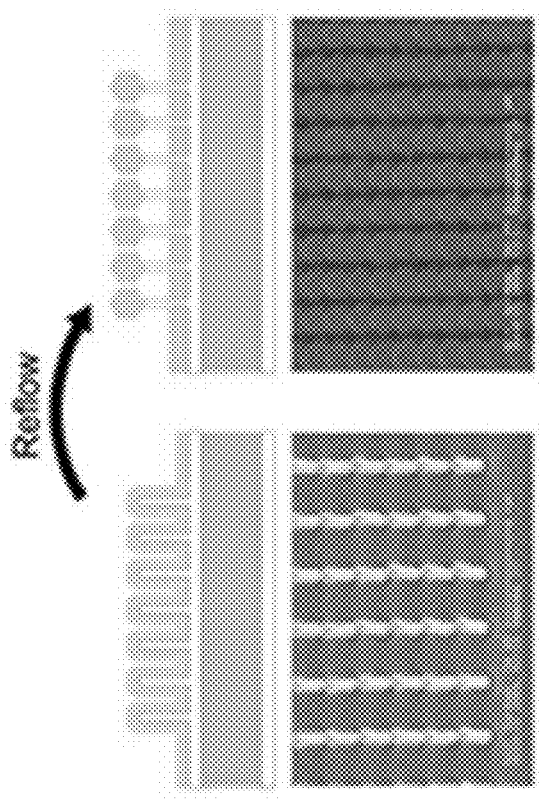
FIG. 8

FIG. 32

REFLOWED GOLD NANOSTRUCTURES FOR SURFACE ENHANCED RAMAN SPECTROSCOPY

CROSS REFERENCE TO RELATED APPLICATIONS

The present application claims priority to U.S. Provisional Patent Application No. 61/938,784, filed on Feb. 12, 2014, U.S. Provisional Patent Application No. 62/046,628, filed on Sep. 5, 2014, U.S. Provisional Patent Application No. 62/049,256, filed on Sep. 11, 2014, and U.S. Provisional Patent Application No. 62/065,224, filed on Oct. 17, 2014, and may be related to U.S. patent application Ser. No. 14/621,265, titled "PLASMONICS NANOSTRUCTURES FOR MULTIPLEXING IMPLANTABLE SENSORS" filed concurrently herewith, U.S. patent application Ser. No. 14/621,286, titled "REFLOWED GOLD NANOSTRUCTURES FOR SURFACE ENHANCED RAMAN SPECTROSCOPY" filed concurrently herewith, U.S. patent application Ser. No. 14/621,295, titled "SURFACE ENHANCED RAMAN SPECTROSCOPY DETECTION OF GASES, PARTICLES AND LIQUIDS THROUGH NANOPILLAR STRUCTURES" filed concurrently herewith, and U.S. patent application Ser. No. 14/621,306, titled "MULTIPLEXED SURFACE ENHANCED RAMAN SENSORS FOR EARLY DISEASE DETECTION AND IN-SITU BACTERIAL MONITORING" filed concurrently herewith, the disclosures of all of which is incorporated herein by reference in their entirety.

TECHNICAL FIELD

The present disclosure relates to implantable sensors. More particularly, it relates to reflowed gold nanostructures for surface enhanced Raman spectroscopy.

BRIEF DESCRIPTION OF DRAWINGS

The accompanying drawings, which are incorporated into, and constitute a part of, this specification illustrate one or more embodiments of the present disclosure and, together with the description of example embodiments, serve to explain the principles and implementations of the disclosure.

FIG. 7 illustrates regions with nanopillars.

FIG. 8 illustrates reflowing of gold on the nanopillars.

FIGS. 32-34 illustrate data on thiophenol experiments.

SUMMARY

Figure 1:
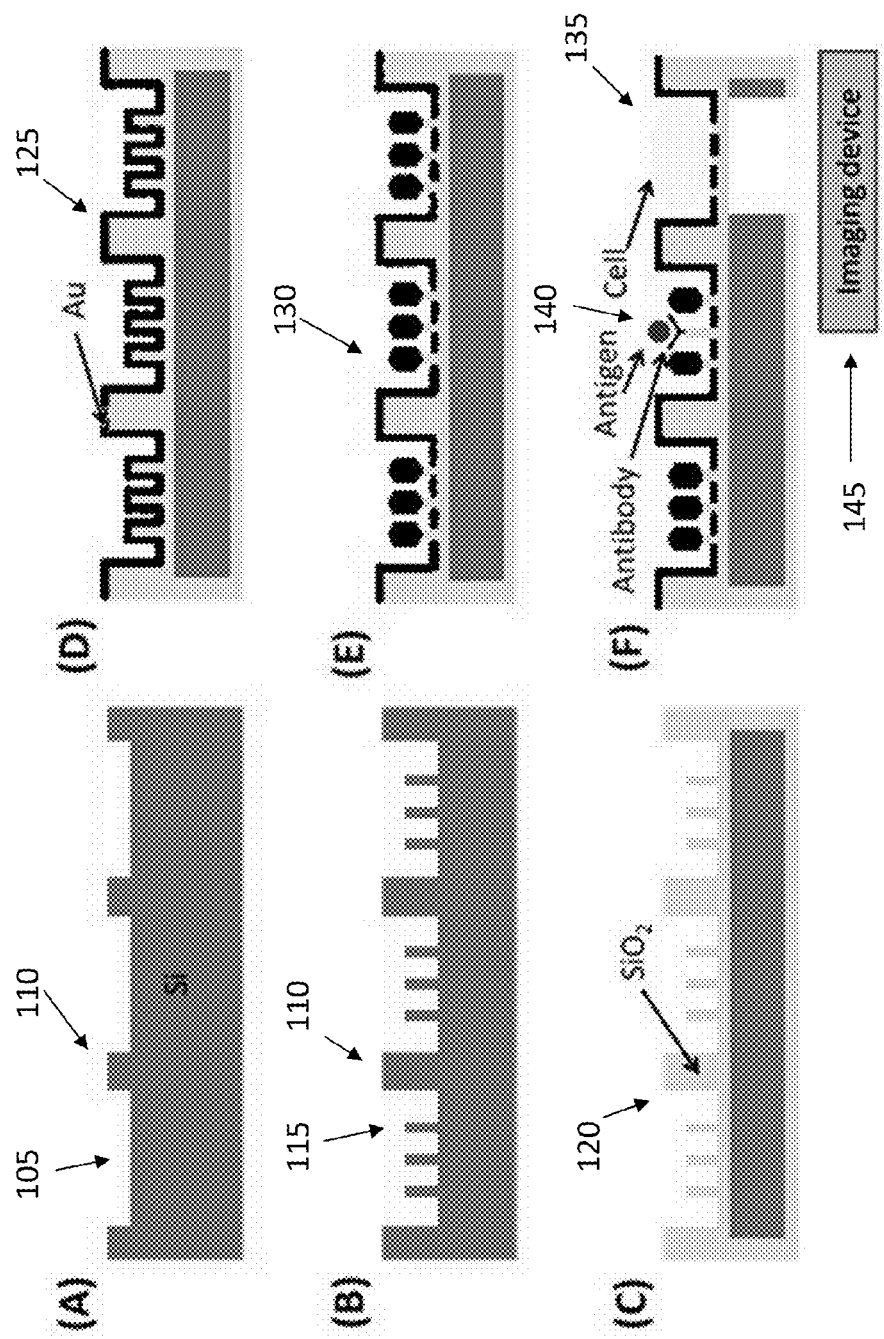
FIG. 1 illustrates an embodiment of a fabrication method for implantable sensors.

In a first aspect of the disclosure, a method is described, the method comprising: providing a substrate; defining at least one recessed region in the substrate; forming nanopillars in the at least one recessed region; depositing a metallic layer on a top end of the nanopillars; by heating the metallic layer, reflowing the metallic layer on the top end of the nanopillars while removing the metallic layer from a middle portion of the nanopillars, thereby forming metallic bulbs on the top end of the nanopillars; and functionalizing the metallic bulbs on the top end of the nanopillars.

In a second aspect of the disclosure, a method is described, the method comprising: providing a substrate; etching at least one recessed region in the substrate; etching at least one groove on a surface of the at least one recessed region; forming nanopillars in the at least one recessed region close to but not within the groove; depositing a metallic layer on a top end of the nanopillars and on a side surface of the at least one recessed region; by heating the metallic layer, reflowing the metallic layer on the top end of the nanopillars while removing the metallic layer from a middle portion of the nanopillars, thereby forming metallic bulbs on the top end of the nanopillars; functionalizing the metallic bulbs on the top end of the nanopillars; and attaching an optic fiber to the groove, the optic fiber having a surface substantially parallel and opposite to the side surface of the at least one recessed region.

In a third aspect of the disclosure, a method is described, the method comprising: providing a substrate; forming nanopillars on the substrate; depositing a metallic layer on a top end of the nanopillars; by heating the metallic layer, reflowing the metallic layer on the top end of the nanopillars while removing the metallic layer from a middle portion of the nanopillars, thereby forming metallic bulbs on the top end of the nanopillars; functionalizing the metallic bulbs on the top end of the nanopillars; etching the substrate on a surface opposite the surface with the nanopillars; inserting an optic fiber in the etched side of the substrate, on the surface opposite the surface with the nanopillars; and lifting the nanopillars with the optic fiber.

In a fourth aspect of the disclosure, a method to detect one or more biomolecules is described, the method comprising: providing a sensor, the sensor comprising a substrate, at least one recessed region on the substrate, nanopillars defined in the at least one recessed region, metallic bulbs on a top end of the nanopillars; exposing the sensor to a composition comprising said one or more biomolecules; and illuminating, by a laser, the metallic bulbs on the top end of the nanopillars, thereby detecting presence or absence of the one or more biomolecules.

DETAILED DESCRIPTION

The present disclosure describes several methods for fabricating plasmonic nanostructures for implantable sensors, as well as different types of implantable sensors. By initially etching into, or depositing onto, some regions of a chip it is possible to fabricate nanostructures in recessed areas. These recessed nanostructures are less likely to be damaged during the implantation process. The nanostructures location can be properly controlled. The nanostructures can comprise deposited metals, which can be subjected to a thermal treatment. By controlling the thermal treatment, it is possible to achieve different levels of surface plasmon enhancement for nonlinear optical processes. For example, taking advantage of the nanoscopic spacing between pillars and metal structures, it is possible to functionalize certain nanostructures for optical readout methods like Förster resonance energy transfer. Wavelength- or polarization-dependent extraordinary transmissions can be implemented by varying the shapes of nanostructures to facilitate on-chip imaging of biological structures, like cells. All these modalities can be combined onto a single chip for multiplexing measurements with raster scanning of the incident laser beam. In such a way, sensors can be fabricated that allow optical measurement and are sensitive to the presence of biological entities. These sensors can be implanted in biological tissues and allow measurement of biological quantities. These sensors can also be implanted in a biological medium to allow measurement of various properties, for example microorganism growth. Exemplary biological media will be apparent to one skilled in the art, and include agar plates, bacterial growth media, and other substances.

In some embodiments, some parts of a chip containing a sensor can be left blank in order to provide baseline signals. These blank areas can also serve as "bar codes". For example, regarding chip orientation during a raster scan, the bar codes can allow the determination of the chip orientation. These blank areas can be termed as empty "grids", while other grids, or areas, can be functionalized with known chemicals to generate strong signals in order to identify the chip orientation. In other words, some parts or grids of a chip may be empty, other parts may be functionalized with known chemicals, and other parts may be used for detection. For example, the parts used for detection can be functionalized to detect a specific biological entity.

As known to the person skilled in the art, top-down fabrication of plasmonics nanostructures can be carried out with a focused ion beam (FIB) technique for precise nanoscopic control of metals like Au or Ag. The FIB technique, however, can be restricted by its focusing ability, the beam tail, and the angular distribution of focused ion beams. These factors can pose a limitation on the smallest achievable features, as well as on the aspect ratio when patterning apertures on metal films that are thicker than 200 nm. Moreover, the FIB method can be slow and therefore non-scalable. Recently, Walavalkar et al. invented a new technique that allows scalable fabrication of plasmonics nanostructures—see Reference [1]. Rather than being handcrafted individually by focused ion beams, with the methods described in Reference [1] plasmonics nanostructures can be produced not only efficiently but also with repeatability. Applications of such nanostructures include, but are not limited to, functionalized assays, high-resolution on-chip imaging via extraordinary transmission, surface-enhanced Raman spectroscopy (SERS), and so on.

As known to the person skilled in the art, non-invasive optical measurement of biophysical signals is also an important topic of research. For example, monitoring of glucose levels with Raman spectroscopy is described in Reference [2]. In a biological system, however, many biological constituents are simultaneously present, and the signal of interest is often buried in the general background. Furthermore, for measurements that utilize a nonlinear optical effect such as Raman scattering, the process is typically very weak and the signal-to-noise ratio again deteriorates. These issues can be addressed with the implantation of a sensor that can respond optically with biochemical specificity, or with an enhanced nonlinear optical process.

The present disclosure describes methods for fabricating implantable sensors with biochemical specificity, and with an enhanced nonlinear optical process. In some embodiments, the methods of the present disclosure begin with defining regions in a silicon wafer. Other types of materials may be used instead of silicon, when suitable for the specific application. The person skilled in the art will understand that variations from the fabrication techniques described below can be carried out, when suitable for specific applications.

For example, regions to be etched in a silicon wafer can be defined with standard techniques such as photolithography. Referring to FIG. 1, step (A) shows a cross section view of an etched wafer. Etched regions (105) are visible, together with non etched areas or mesas (110). Using similar fabrication procedures known to the person skilled in the art, for example as described in Reference [1], nanoscopic patterns (115) can be defined inside the etched regions (105). For example, techniques such as e-beam lithography can be applied, followed by a pseudo-Bosch etch to obtain 3D-sculpted nanostructures with vertical sidewalls as shown in step (B). As can be seen from FIG. 1, the nanostructures (115) lie below the top surface (110), therefore there is no risk of damage during the implantation process.

In a subsequent step, the sensor chip can be oxidized so that the nanostructures are transformed into glass, as indicated in step (C). For example, the silicon chip is oxidized to form a layer of silica (120). Metal can then be deposited onto the chip. For example, in step (D) gold (125) can be sputtered onto the silica. Other metals or deposition techniques can be applied.

With an appropriate thermal treatment, the metal deposited on the nanostructures can separate from the bottom layer and wick onto the pillar tops. For example, as visible in step (E) of FIG. 1, the gold wicks on the top of the nanopillars (130) form due to the thermal treatment. By controlling the thermal process, the spacing between the metal structures on the top (130) can be on the order of 5 to 50 nm. Such spacing presents a great improvement over the spacing that is typically achievable with a focused ion beam. Further, the whole process described in the present disclosure is scalable. With such a short spacing between metal structures, surface plasmons can greatly increase the efficiency of Raman scattering, which facilitates optical measurement through surface-enhanced Raman spectroscopy. As a consequence, greatly improved sensors can be fabricated. The person skilled in the art will understand that different spacings are possible, for example smaller than 50 nm or greater than 5 nm.

As visible in FIG. 1, a metallic layer is deposited on the nanopillars, comprising a metallic layer on a top end of the nanopillars, the metallic layer on the top end of the nanopillars being thicker than the metallic layer on a remaining part of the nanopillars. This thicker part of the metallic layer is formed due to the application of the thermal treatment and can have a bulbous shape.

With further fabrication steps, some of the nanopillars can be functionalized into a chemical assay, and various methods can be used for optical readout of these functionalized sites. For example, Förster resonance energy transfer (FRET) can be applied to take advantage of the short distance between the functional groups and the nearby metal structures.

In some embodiments it is possible to remove parts of the nanopillars, obtaining a high-aspect-ratio glass region through the optically-thick metal film. This region allows high-resolution imaging based on plasmonic extraordinary transmission for on-chip objects such as cells. In some embodiments, the sensors are optimized solely for these high-aspect-ratio glass regions. An example of these regions is visible in step (F), with a cell being detected (135). In some embodiments, the nanopillars are removed after deposition of the metallic layer (as per Walavalkar et al. in Reference [1]), therefore the region for detection of cells comprises a non-continuous metallic layer with silicon or silica areas where the nanopillars were previously present.

By varying the nanoscopic patterns, the transmission used for imaging may be wavelength- or polarization-dependent, making the imaging capability more versatile. An imaging device (145), such a wirelessly-powered complementary metal-oxide semiconductor (CMOS) sensor, can be attached under the chip to transmit the images wirelessly back to a receiver. These variations are depicted in step (F). As visible in step (F), some nanopillars can be functionalized (140). For example, antigens and antibodies can be used in the functionalization. In step (F), an example of a functionalizing agent is illustrated in a nanopillar without a gold top. However, such functionalizing agents can be applied to nanopillars with a gold top as well.

Figure 2:
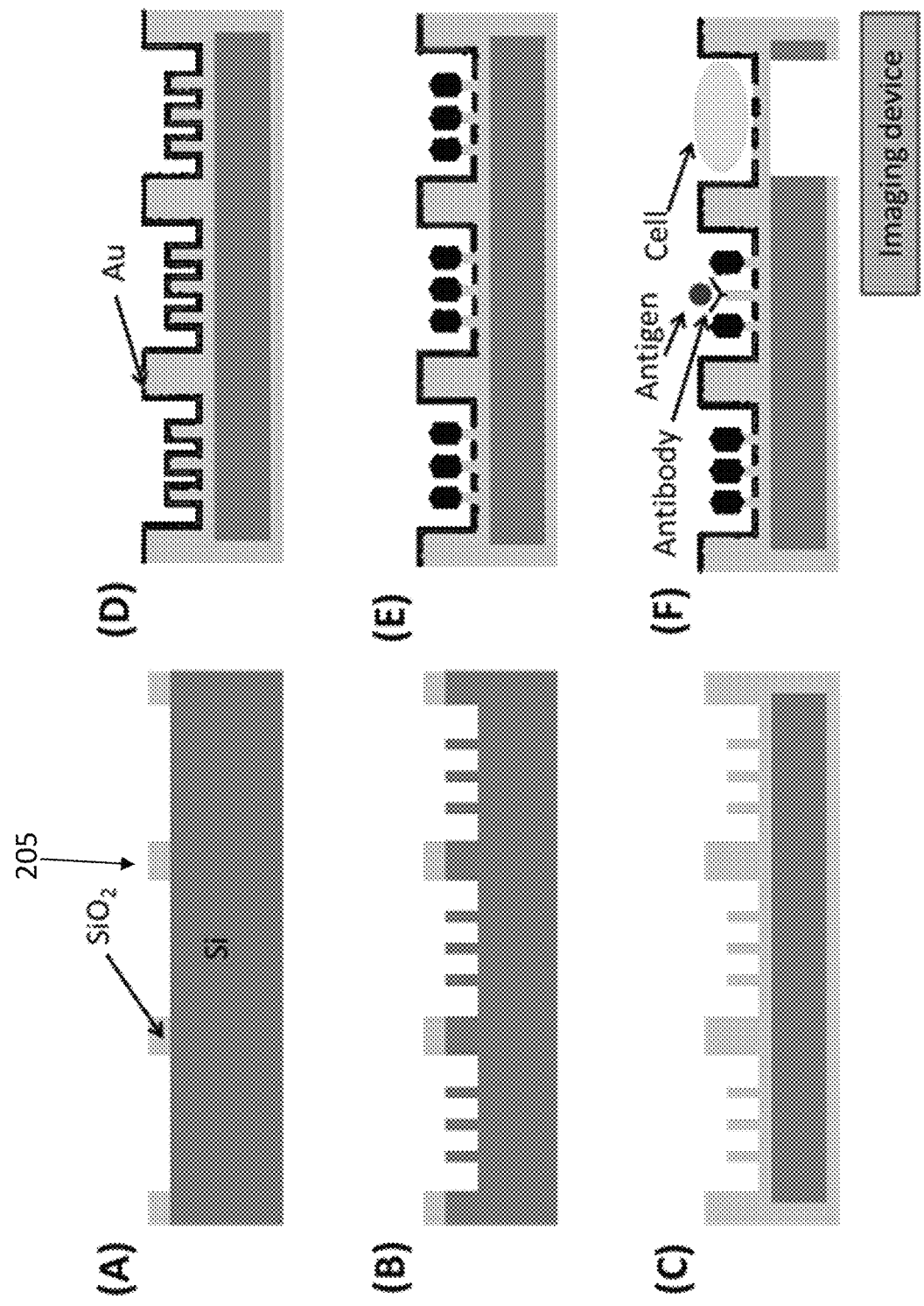
FIG. 2 illustrates an embodiment of a fabrication method for implantable sensors.

In other embodiments, other methods can be used to protect the nanostructures during the implantation process. Referring to FIG. 2, step (A), for example, an additional layer (205), such as $SiO_2$, can be fabricated at the beginning of the fabrication process. For example, the mesas (205) have been oxidized, on top of the silicon wafer. Other regions have been etched similarly to FIG. 1. The remaining steps, (A)-(F), visible in FIG. 2 are equivalent to those in FIG. 1, apart from the initial oxidization step that created the oxidized regions (205).

Figure 3:
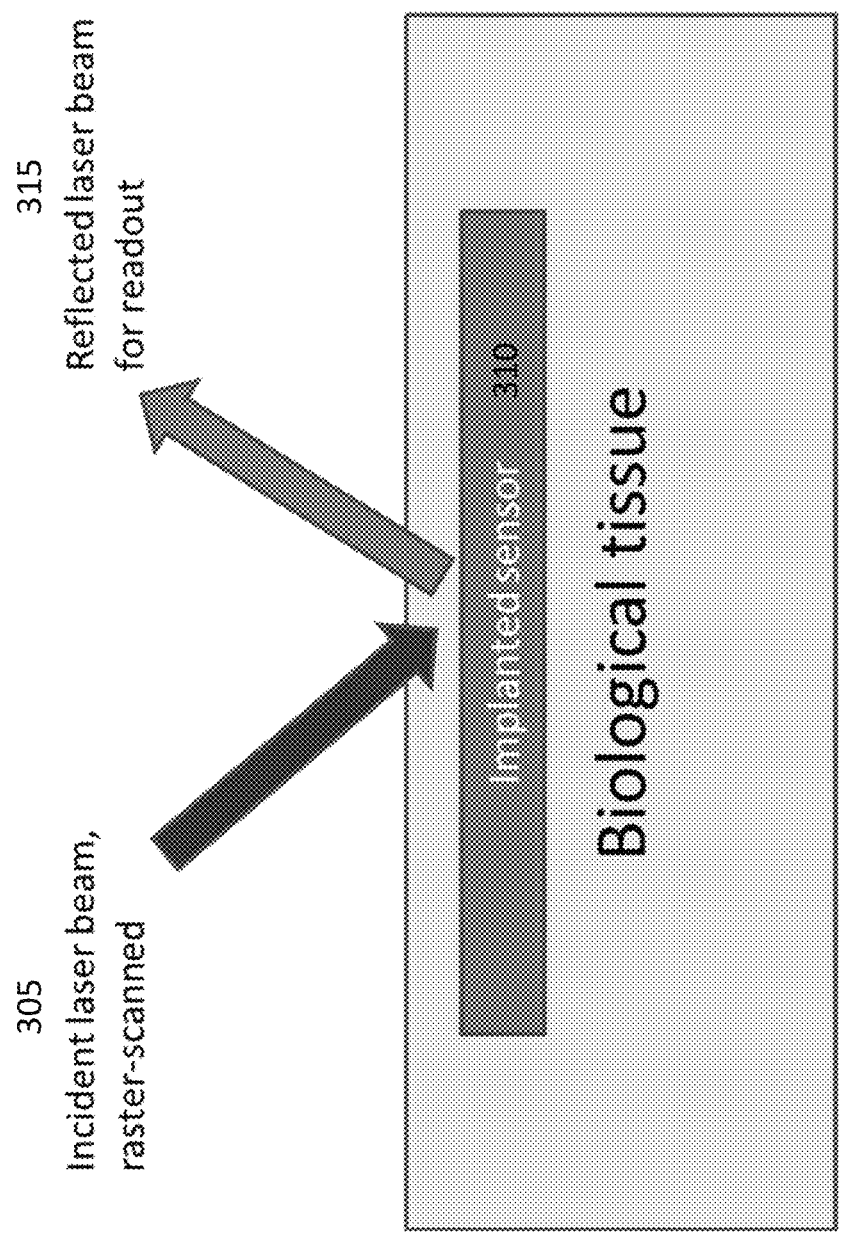
FIG. 3 illustrates an embodiment of a detection method for implantable sensors.
Figure 4:
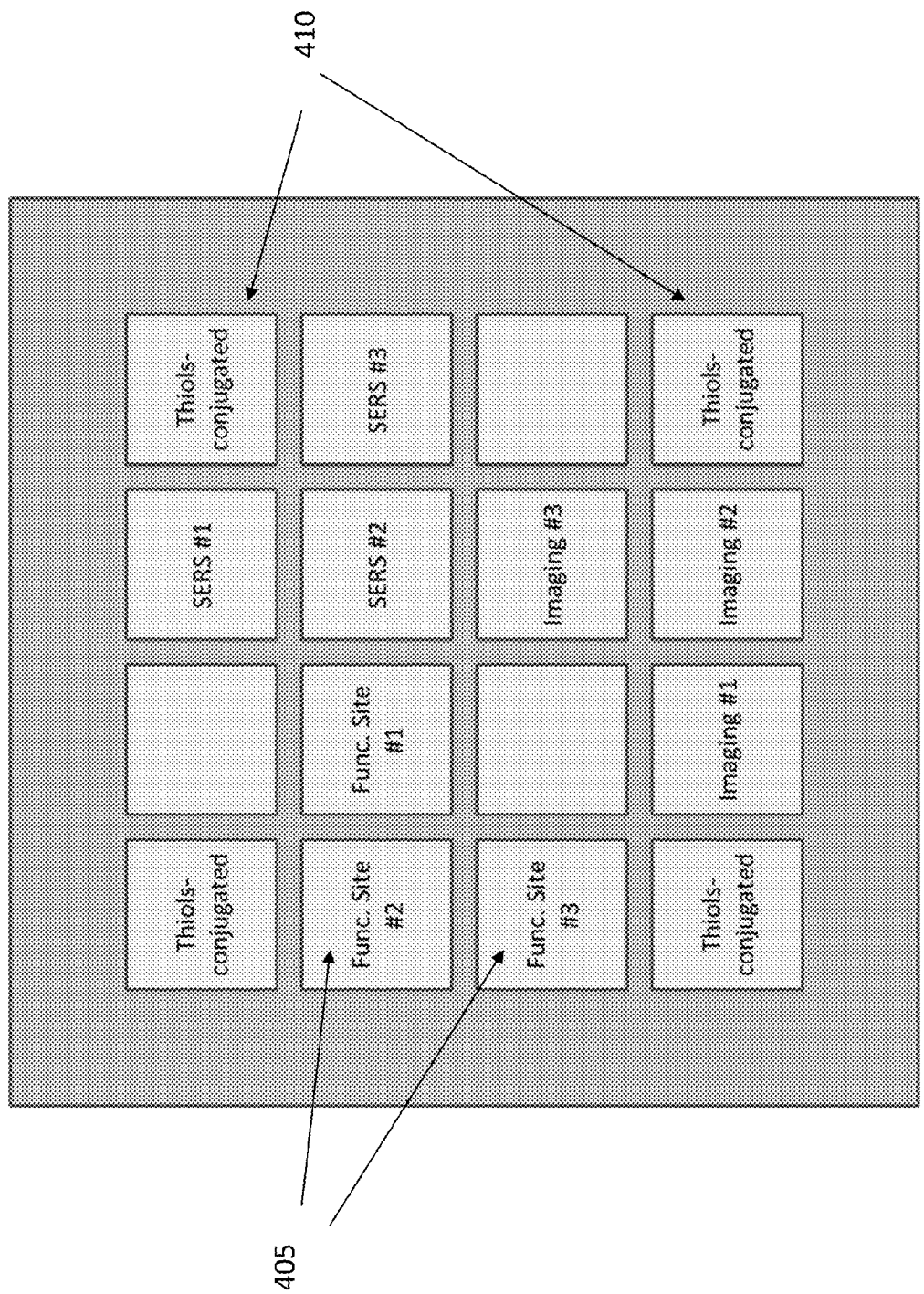
FIG. 4 illustrates an embodiment of an array of detecting regions.

Subsequently to fabrication, the chip can be implanted into biological tissues, as shown for example in FIG. 3. A laser beam (305) can be illuminated onto the implant region (310). The reflected beam (315), which may carry the Raman spectroscopic information, can be collected by the associated optical setup. By fabricating multiple groups of structures on the same chip, it is possible to multiplex the measurement by raster-scanning the incident laser beam. Referring to FIG. 4, for example, there can be different functionalized sites (405), each functionalized individually for a unique biochemical target. Each site (405) can have SERS structures with different spacing between metal parts or pillar locations, so that each structure corresponds to a different level of enhancement. In some embodiments, there can be different nanoscopic openings for wavelength- or polarization-dependent imaging on the chip. Some grids can be left blank without nanostructures, to serve as "bar codes" for the raster scan; in this manner, the scan direction doesn't have to be parallel with an edge of the entire layout, which would be convenient when the chip is implanted in a living animal or a patient for clinical purposes. For example, when the laser beam scans onto the metal-coated region, which is empty of nanostructures, the abrupt increase of reflected signals can be used to identify the general location of the chip. The reflection from these "bar-code" areas can be used to deduce the orientation of the chip to calculate the exact location of individual nanostructure groups for the multiplexing measurement. These blank regions can also provide a baseline signal for the ever-changing biological environment. For example, if the chip is implanted under the skin, reflected signals from these regions can serve as a baseline for the interstitial fluid and help resolve the enhanced signals from the nanostructures. Another method to identify the chip orientation is to functionalize specific regions with known chemicals that generate strong signals. In FIG. 4 the four corners, such as (410), are functionalized with thiol conjugated to fluorescent molecules, for example. The example of FIG. 4 can be considered an array of recessed regions, each with defined nanopillars, and constituting an implantable sensor.

As illustrated above, the present disclosure describes methods to etch areas on the chip, in which nanostructures are subsequently fabricated, so that they would not be damaged during the implantation process. In some embodiments, the height of the nanopillars is equal or less than the height of the remaining parts of the structure, such as the mesas (110) of FIG. 1. In some embodiments, protective materials can be deposited to protect the nanostructures from being damaged during the implantation process. For example, oxides, metals or polymers can be used as protective materials. The protective materials can encase the sensor chip while allowing access from biological entities to the top surface where the nanostructures are located. Due to the small spacing between metal structures, surface-enhanced Raman spectroscopy (SERS) can be used for optical measurement of biochemical species on the chip. By functionalizing some nanostructures, the close spacing to the neighboring metal structures allows for optical readout of the biochemical binding. One example of a method that can be used for optical readout of these functionalized sites is Förster resonance energy transfer.

Figure 5:
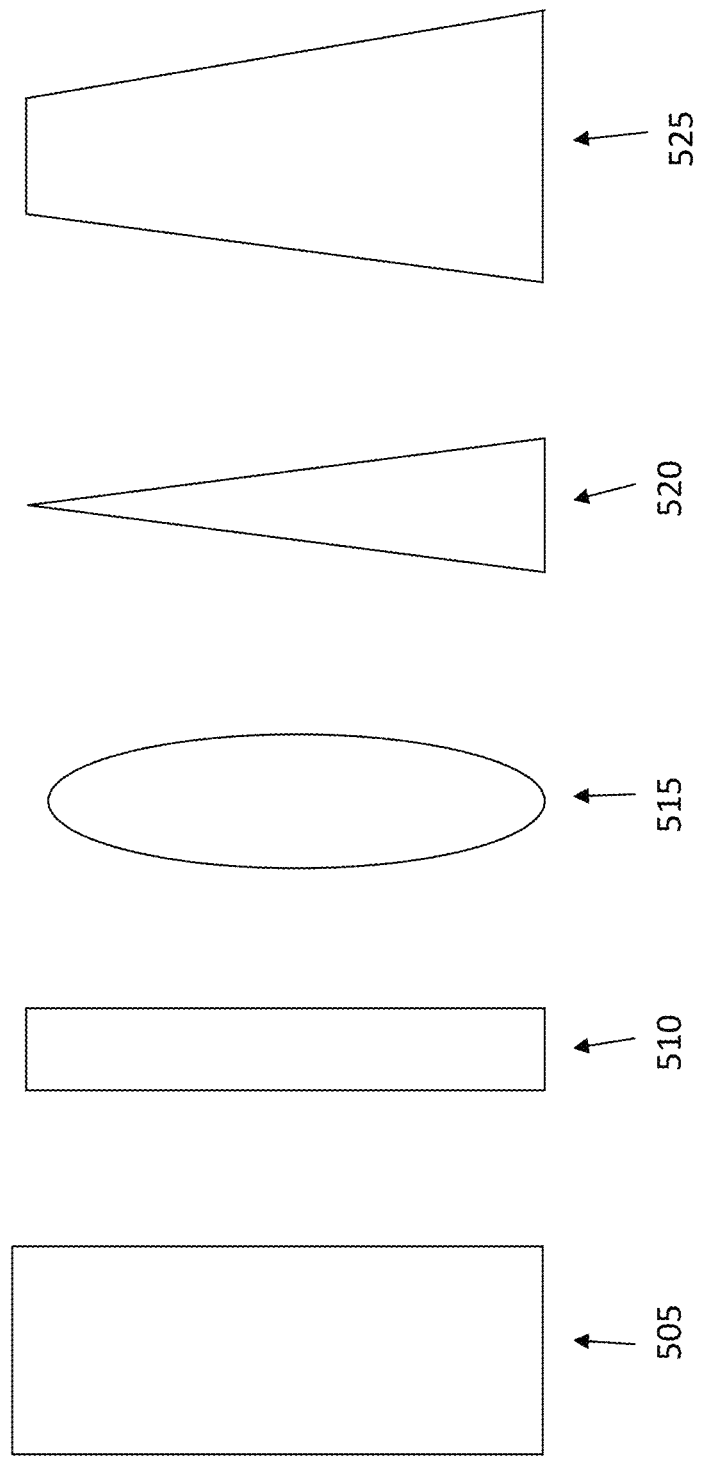
FIG. 5 illustrates different types of nanopillars.
Figure 6:
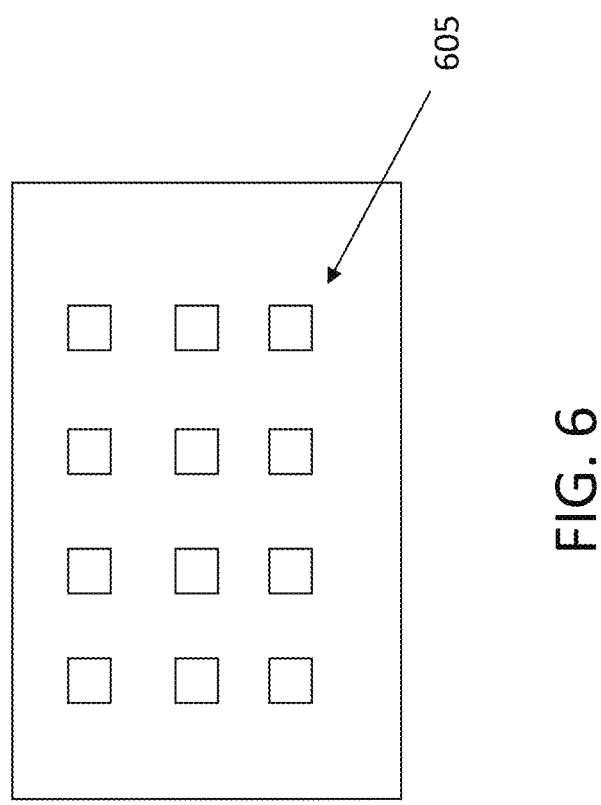
FIG. 6 illustrates an embodiment of an array of detecting regions.

Various shapes of nano structures can achieve wavelength- or polarization-dependent extraordinary transmission, which can be used for on-chip imaging of biological structures like cells. For example, as show in FIG. 5, the nanopillars in each region of an array of detecting regions may be parallelepipeds (505, 510), ellipsoids (515), pyramidal (520), or tapered (525), and have different lateral dimensions, height, or spacing. Different metals or different functionalizing agents may be deposited on each detecting region in order to distinguish between regions. In some embodiments, each of the detecting regions may be optimized for a different optical technique, such as SERS. The example array of FIG. 4 is a square array, as the array has the same number of regions in the two lateral dimensions. FIG. 6 illustrates an example of a rectangular array, where each area (605) is a region with nanopillars.

An imaging device can be attached to the chip, and the imaging part can be wirelessly powered with another wireless data-link. Different types of nanostructures can be fabricated onto the same chip for multiplexing measurements; the incident laser beam then raster-scans onto the chip for the optical reading. Different functionalized sites can individually target a unique biochemical species for multiplexing. Different spacing between pillars and/or metal structures can be fabricated to achieve different degrees of surface plasmon enhancement. Some regions can be left blank without nanostructure fabrication, so that the reflected laser beam carries the baseline signal of its ambient environment. The blank regions can be specifically arranged into a pattern as "bar codes" on the chip, so that the scanning results can be post-processed to identify the chip orientation. Some regions can be functionalized with known chemicals that generate strong optical responses to identify the chip orientation.

In some embodiments, the implantable sensors can be configured to employ SERS detection. Raman spectroscopy is an inelastic scattering technique that can extract the spatial, chemical, conformational and bonding nature of a substance. Raman spectroscopy works by shining an incident laser at a known wavelength at a sample and examining the change in wavelength of the light returning from the sample, as visible for example in FIG. 3. Changes in wavelength are caused by the absorption of small amounts of energy into vibrational modes of the molecule. The amount of energy lost to each vibration mode is unique to the type of bond (single/double/triple), the chemical species involved in the bonding (e.g., C bonded to H), and the chemical species that surround the bond (e.g., whether a bond is participating in hydrogen bonding). However, this technique can be inefficient, as about 1 in 10 million photons participates in Raman scattering.

SERS, on the other hand, is a more efficient Raman technique. SERS relies on the use of surface-based metallic nanostructures to enhance and focus both the incident and outgoing light to greatly improve the efficiency of Raman scattering. One of the best structures for this enhancement is a 'nano-gap' structure, featuring a nanoscale (<50 nm) gap between two electrically isolated metallic structures. An example of such a structure is the nanopillars structure as illustrated for example in FIG. 1. Light incident to a SERS structure sets up a polarizing electric field across the gap, which is enhanced and strengthened by charges in the metal. Previous methods known to the person skilled in the art have relied on stochastic techniques (e.g., spinning gold beads onto a glass substrate and hoping two are near each other), FIB techniques, or top-down lithographic techniques to fabricate SERS structures. The method that is presented in the present disclosure is a template fabrication method that combines both top-down and bottom-up fabrication to create nano-gap junctions in the nanometer range. For example, the spacing between nanopillars can be in the 5 nm range. The Raman signal from these structures can be enhanced by a factor greater than $10^{\wedge}10$. This technique can be used (without labels) to detect, for example, thiophenol, tracheal cytotoxin, structures of DNA aptamers, and single Thrombin molecules. Tracheal cytotoxin, for example, was previously impossible to detect in situ or without complex HPCL techniques, without the methods presented in the present disclosure.

Similarly to the methods described referring to FIGS. 1 and 2, SERS structures can be fabricated on a substrate, such as a silicon substrate. Silicon nanopillars can be fabricated and oxidized as described, for example, in U.S. Pat. No. 8,080,468, filed on Jun. 10, 2010, the disclosure of which is incorporated herein by reference in its entirety. Referring to U.S. Pat. No. 8,080,468, fabrication methods are described in FIG. 1, steps a-b of U.S. Pat. No. 8,080,468. Specifically, a thin layer of titanium, followed by a 100-300 nm thick layer of gold, can be sputtered onto the substrate using an Ar+ sputtering gun (as in step c of FIG. 1 of U.S. Pat. No. 8,080,468). The chip can then be inserted in a rapid thermal annealer to cause the gold to bead on top of the silica nanopillars. The temperature, ramp up, and ramp down parameters can be tuned to create either spherical or rod-like shapes. These shapes can be further enhanced through other top-down and bottom-up fabrication techniques (such as, for example, ion milling, chemical etching, etc.).

Referring to FIG. 7 of the present disclosure, some examples are illustrated of the small gaps that can be created between the reflowed metal. For example, the gap (705) between nanopillars (710, 715) covered in a bulb of metal is smaller than the gap (720) between nanopillars not covered by metal. As visible in FIG. 7, the nanopillars in step a) are oxidized in step b). Subsequently a metal layer is deposited in step c) and a thermal process causes the metal to bead up on top of the nanopillars as in step d). Therefore, in some embodiments, in step c) the metallic layer covers entirely the nanopillars, while after beading up, in step d) the metallic layer covers the top end of the nanopillars and the bottom of the regions, but not the mid portion of the nanopillars.

There can be several variations to this design with respect to the 3D shape of the pillar (conical, sculpted, etc.), cross section of the pillar (square, rectangular, oval, etc.), cross sectional area of the pillar, spacing between pillars, initial metal thickness, reflow time, reflow temperature, cooling speed, and heating speed. Each of these provides a unique metallic knob or bulb in this fabrication process to tune the final gold bulb diameter and gap size between gold bulbs. FIG. 7 illustrates exemplary scanning electron microscope (SEM) images of an array of nanopillars (725, 730), and nanopillars with a metallic bulb (735).

While keeping the bulbs electrically isolated from each other can be important for enhancing the gap-based electric field, in some embodiments it is possible to design structures that have bulbs that are not electrically isolated yet still display Raman enhancements. For example, referring to FIG. 8, the SEM images (805, 810) illustrate examples of non-electrically isolated nanopillar structures. The physical reason for the Raman signal of the structures of FIG. 8 comes from the fact that in an optical detection cycle the electrons cannot move from one bulb to the other along the U-shaped electrical path from bulb to bulb. Therefore, for the purpose of detection, the electrons behave in a manner that is effectively similar to that of isolated structures.

Figure 9:
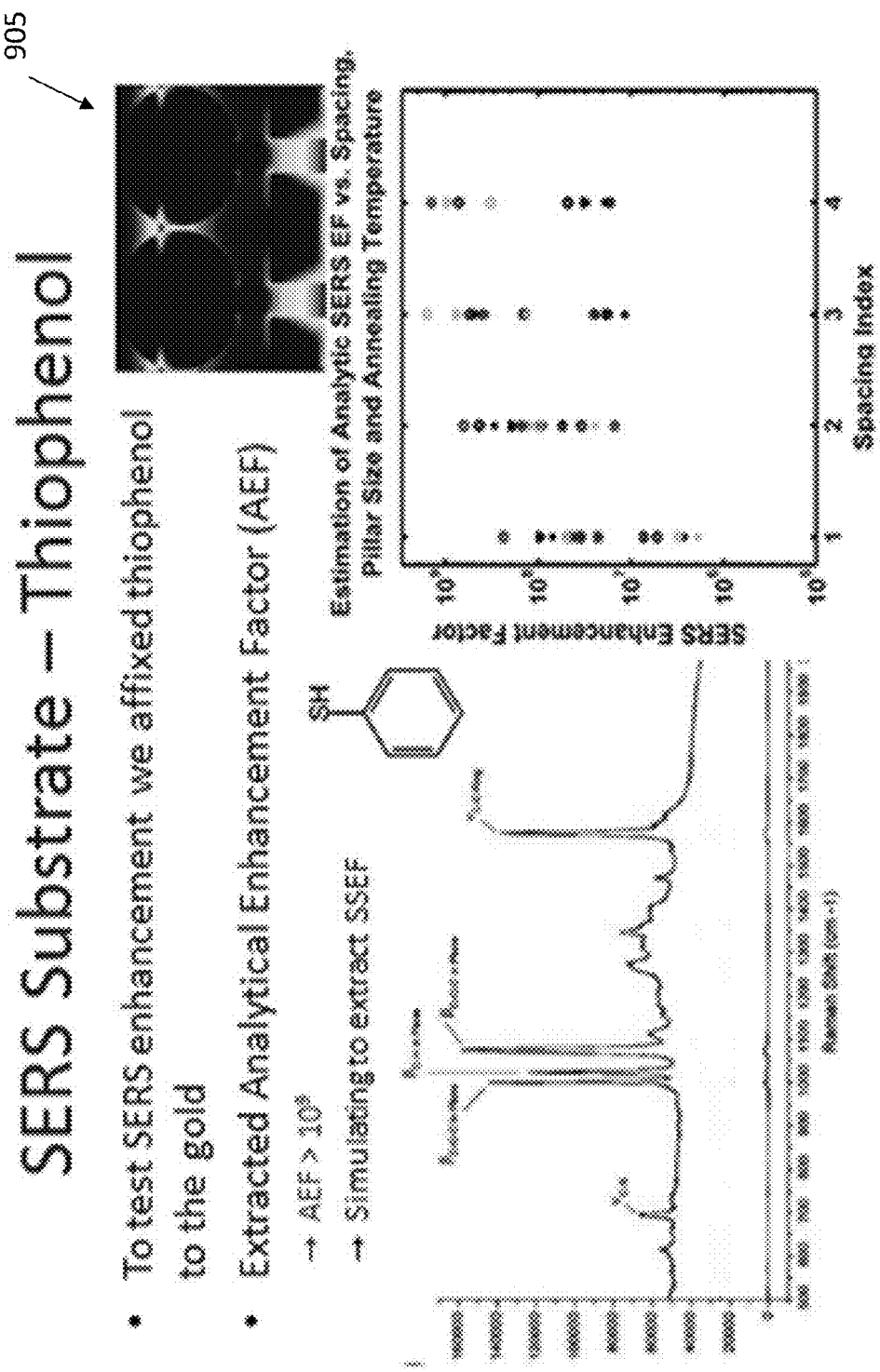
FIG. 9 illustrates thiophenol measurements.

With regard to the functionalization of the nanopillars, a variety of methods can be used to attach molecules to the metallic layer. One method, which can be used for example to detect Tracheal Cytotoxin, is to allow the substance, dissolved in a buffer solution, to dry on the surface of the chip. There are a variety of other methods that can be employed. For example, the substances of interest can be attached to the bulbs by chemical bonding, inkjet printing, metal segregation, Langmuir Blodgett films, and polymethylmethacrylate (PMMA) based masked approaches. One example of a chemical bonding approach is the gold-sulfur bond of a thiol group. This bond can be stronger than the gold-gold bond, as studies have shown that as the sulfur moves on the metal surface it can drag along the gold atom it is bonded to. As illustrated in FIG. 9, using this method, it can be possible to attach thiophenol to the metallic bulbs on the nanopillars of the present disclosure, obtaining a SERS enhancement of $2 \times 10^9$ when compared to the Raman spectra from thiophenol in water. One attachment method consists in the incubation of an $O_2$ plasma-cleaned chip in a thiophenol solution for several hours. Subsequently, a rinse with DI water can be applied. The exemplary $2 \times 10^9$ reported enhancement is the Analytical Enhancement Factor (AEF) and compares the signal received, laser spot voxel/area, and number of thiophenol molecules on the gold sphere surface/volume voxel. By taking the ratio of the two signals (surface/volume) and accounting for the number of molecules in the sample area of each, the enhancement factor provided by the chip can be calculated. In this exemplary case, the AEF is an underestimation of the actual enhancement since the field is only enhanced at most an annulus of the sphere for non-polarized light but can be reduced to two isolated spots on each sphere for linearly-polarized excitation (as shown from computer simulations), not over the entire surface.

An exemplary top-down fabrication method allows control of how the spacing/pillar size/annealing temperature affects the AEF. Computer simulations (905) show that the field can be enhanced by a factor of 300-1000 in the hot spots of the sphere.

Figure 10:
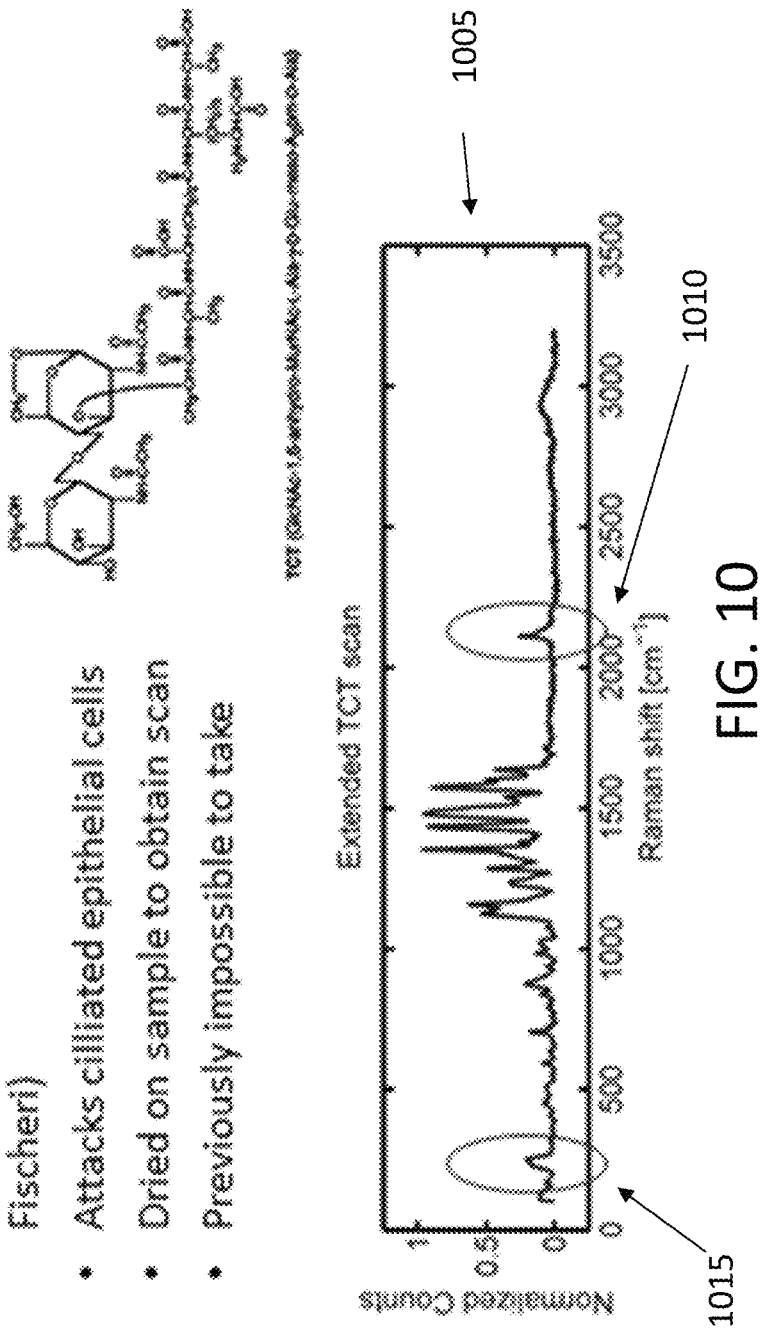
FIG. 10 illustrates TCT measurements.

In some embodiments, as for example illustrated in FIG. 10, the methods of the present disclosure can be used to find Tracheal Cytotoxin (TCT), a molecule whose spectra had not been measured previously. TCT is produced by gram negative bacteria and destroys ciliated epithelial cells. In this exemplary method, a nanomolar concentration of TCT is allowed to dry on the substrate with metal bulb nanopillars to obtain the Raman spectra (1005). Although there does not exist a previously collected Raman spectra to compare the data to, certain elements of the TCT molecule such as the bicyclic ring structure give characteristic peaks at a Raman shift of 200 cm$^{-1}$ (1015) and 2100 cm$^{-1}$ (1010).

In some embodiments, aptamers (nucleic acid strands, for example DNA or RNA, with conformations that can bind certain biomolecules) can be attached to the surface of the gold bulbs on the nanopillars by using a thiol chemistry as described above herein. Samples can be incubated overnight in a phosphate-buffered saline (PBS) solution containing the aptamer, then rinsed several times with clean PBS solution to ensure that there is no non-bound aptamer left on the surface. It is then possible to take the Raman spectra of the aptamer and see peaks associated with its conformation. Subsequently, it is possible to sequentially heat and cool the aptamer to denature and renature it and observe the Raman spectra change based on the conformation changes of the nucleic acids.

Through the methods described above, it is also possible to detect thrombin at low concentrations, for example at 500 fM concentration. Using a microfluidic chamber with an exemplary size of 1.5 cm×1.5 cm×300 μm, a 500 fM concentration corresponds to 1 thrombin molecule per 15 micron on a side cube. In this experimental set up, the laser spot used for optical measurements was 1 μm in diameter. From the concentration stated above, detection with the laser could be taken as a key indication of single molecule detection.

Figure 11:
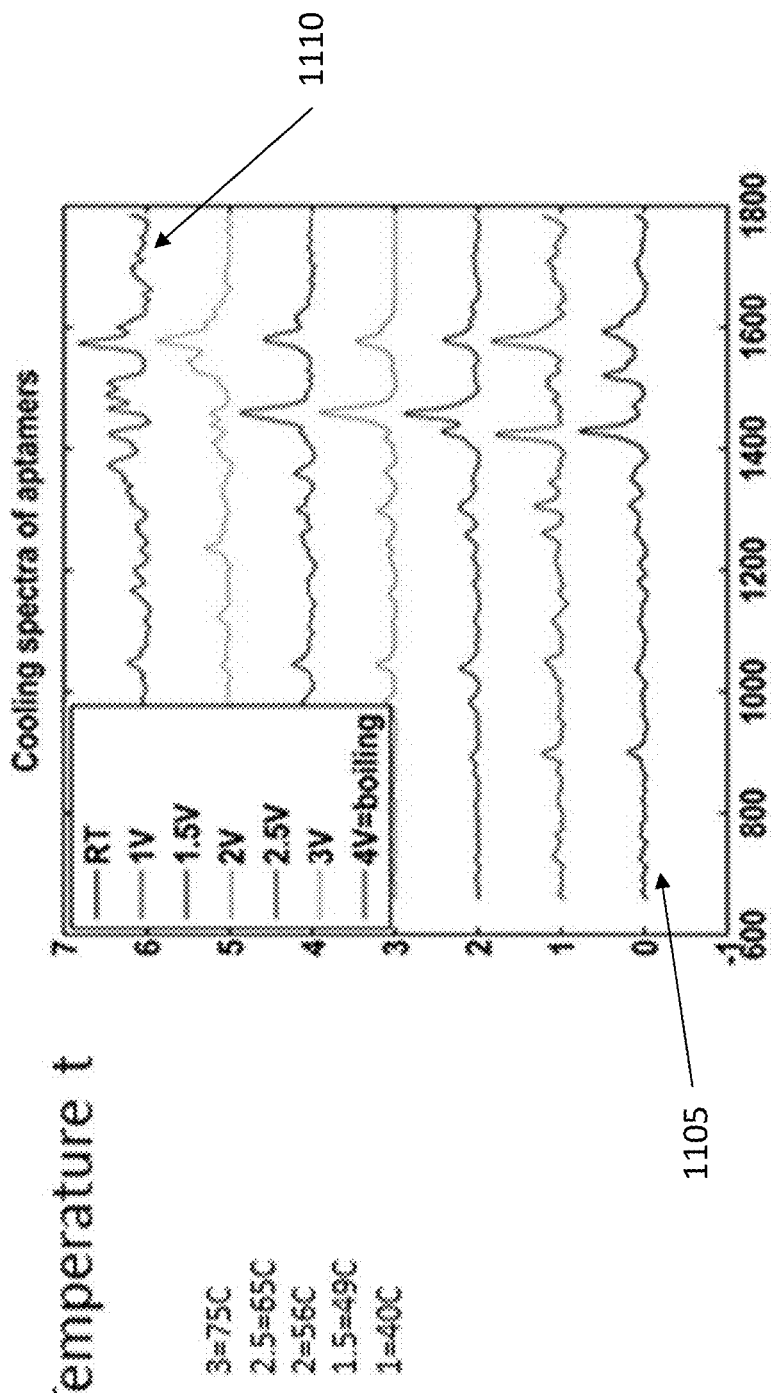
FIG. 11 illustrates thrombin measurements.

FIG. 11 illustrates a graph for the detection of thrombin. The lower curve (1105) was taken at room temperature, with monotonically increasing temperatures for the remaining curves towards the boiling temperature (1110).

Figure 12:
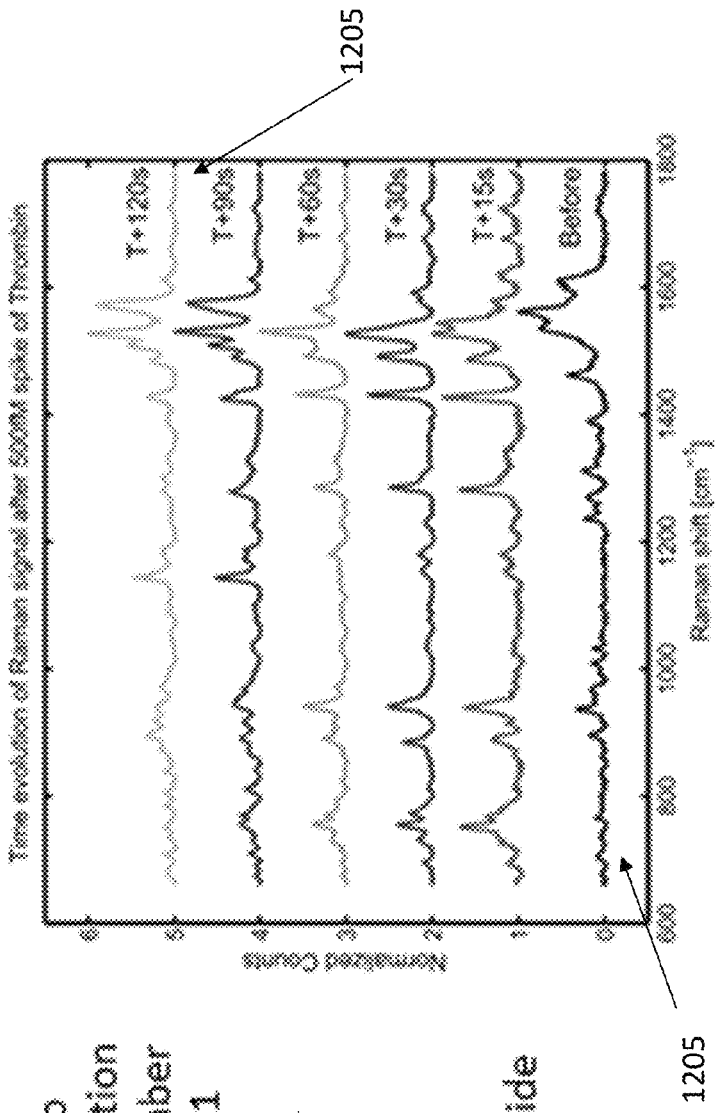
FIG. 12 illustrates additional thrombin measurements.

FIG. 12 illustrates the time spectra of a 500 fM thrombin solution evolving in time. Optical heating or resistive elements can be used to heat and desorb the thrombin and then let the aptamer renature and use it for thrombin binding again. The lower curve (1205) was taken at time zero, with monotonically increasing time for the remaining curves towards time equal to two minutes (1210).

Figure 13:
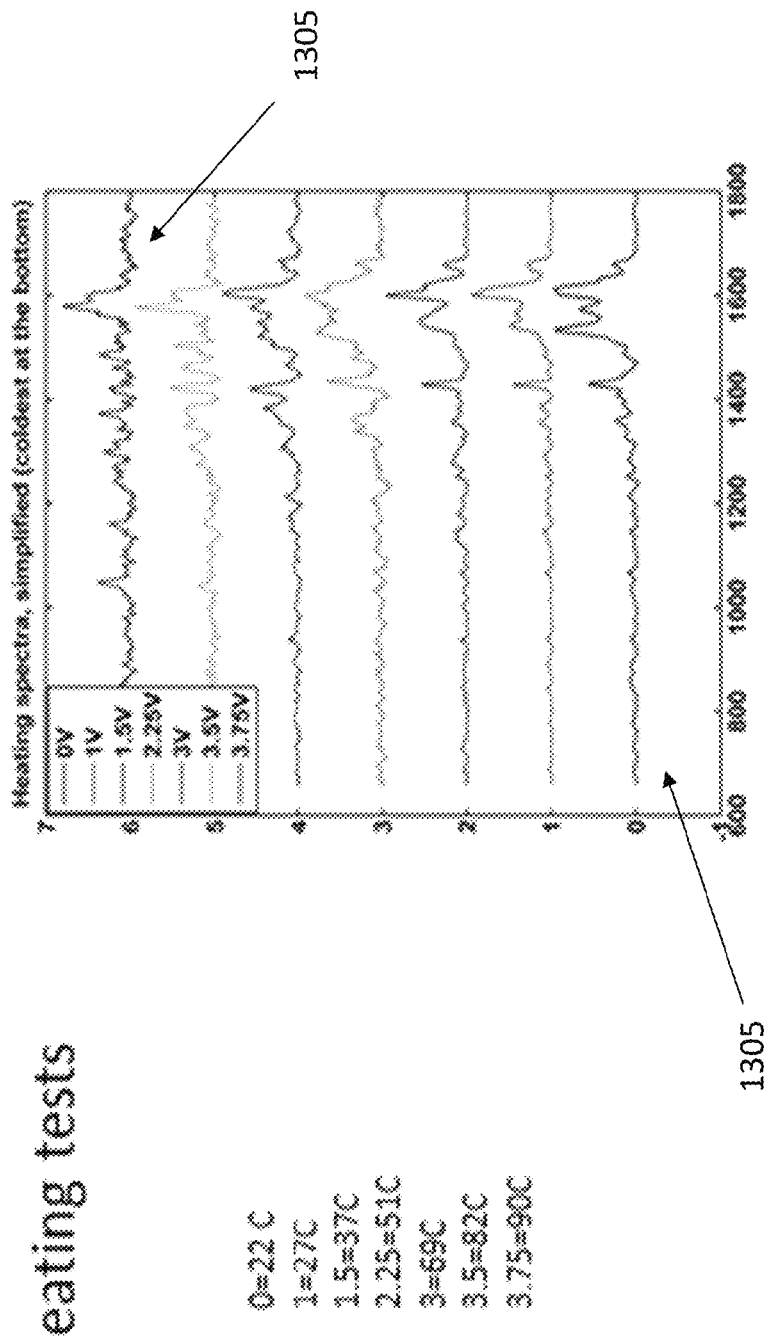
FIG. 13 illustrates a heating test for thrombin.

FIG. 13 shows the heating and desorption of thrombin followed by the unraveling of the aptamer followed by stochastic conformation behavior of the aptamer in a near boiling liquid solution. The aptamer then cools back into shape as shown in the cooling spectra of FIG. 11. The thrombin related peaks are not present as the liquid was allowed to boil, denaturing the complex structure of thrombin while not allowing binding to the aptamer. The lower curve (1305) was taken at room temperature, with mono- tonically increasing temperatures for the remaining curves towards a temperature of 90 degree Celsius (1310).

Figure 14:
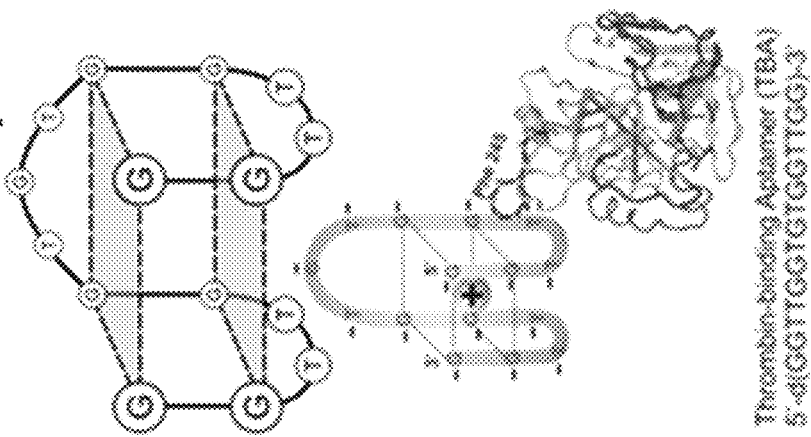
FIG. 14 illustrates an aptameric assay.
Figure 15:
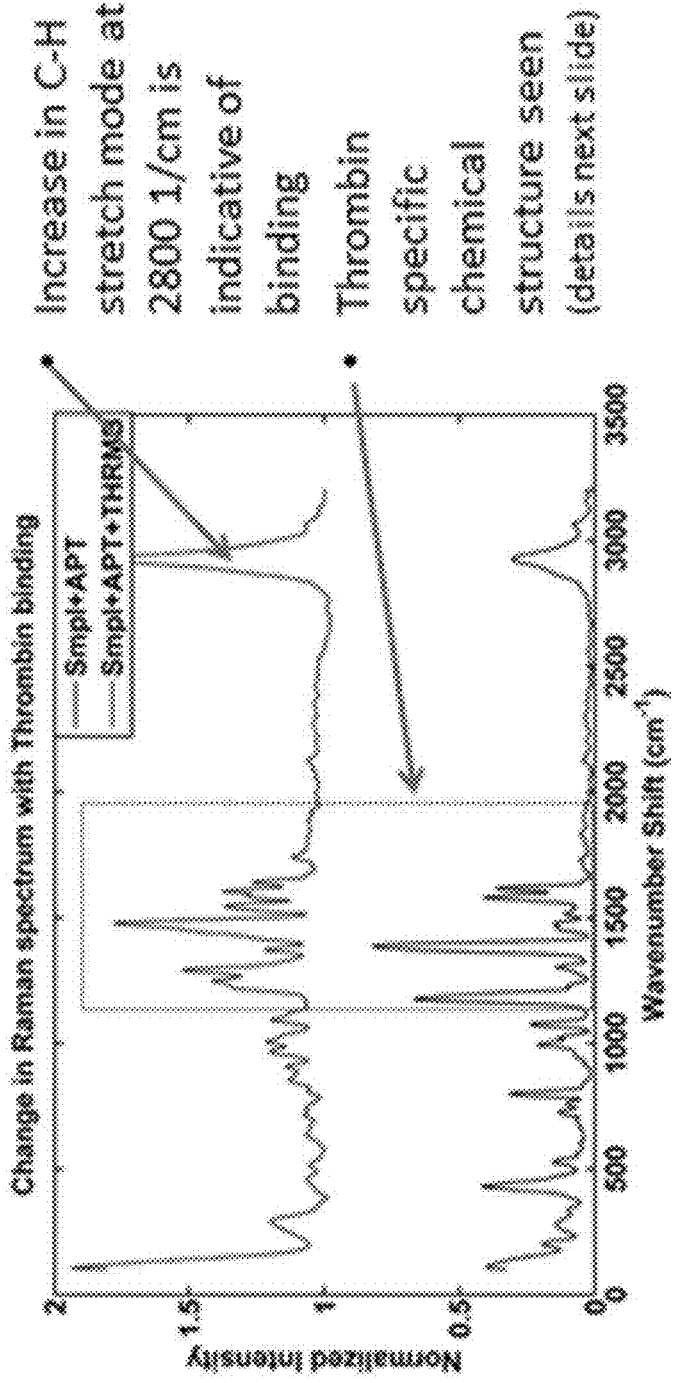
FIG. 15 illustrates SERS measurements for thrombin.
Figure 16:
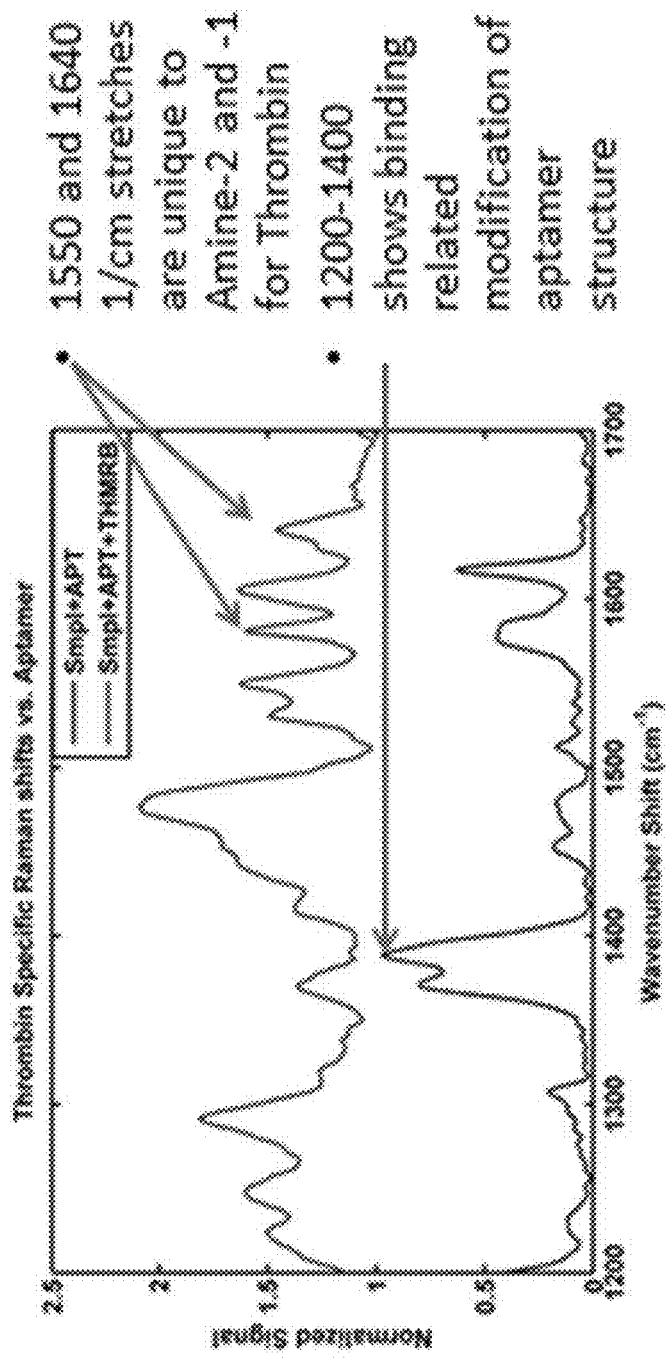
FIG. 16 illustrates Raman signals for thrombin.

FIGS. 14-16 illustrate the components and specifics of an aptamer/thrombin system, as well as specifics of the differences between some of the spectral peaks of the aptamer and the aptamer and thrombin. FIG. 14 illustrates exemplary aspects of aptameric assays, as well as a thrombin-binding aptamer and an aptamer-thrombin structure. FIG. 15 illustrates experimental measurements of thrombin-aptamer binding. FIG. 16 illustrates a detailed view of the experimental Raman measurements of thrombin shown in FIG. 15.

Figure 17:
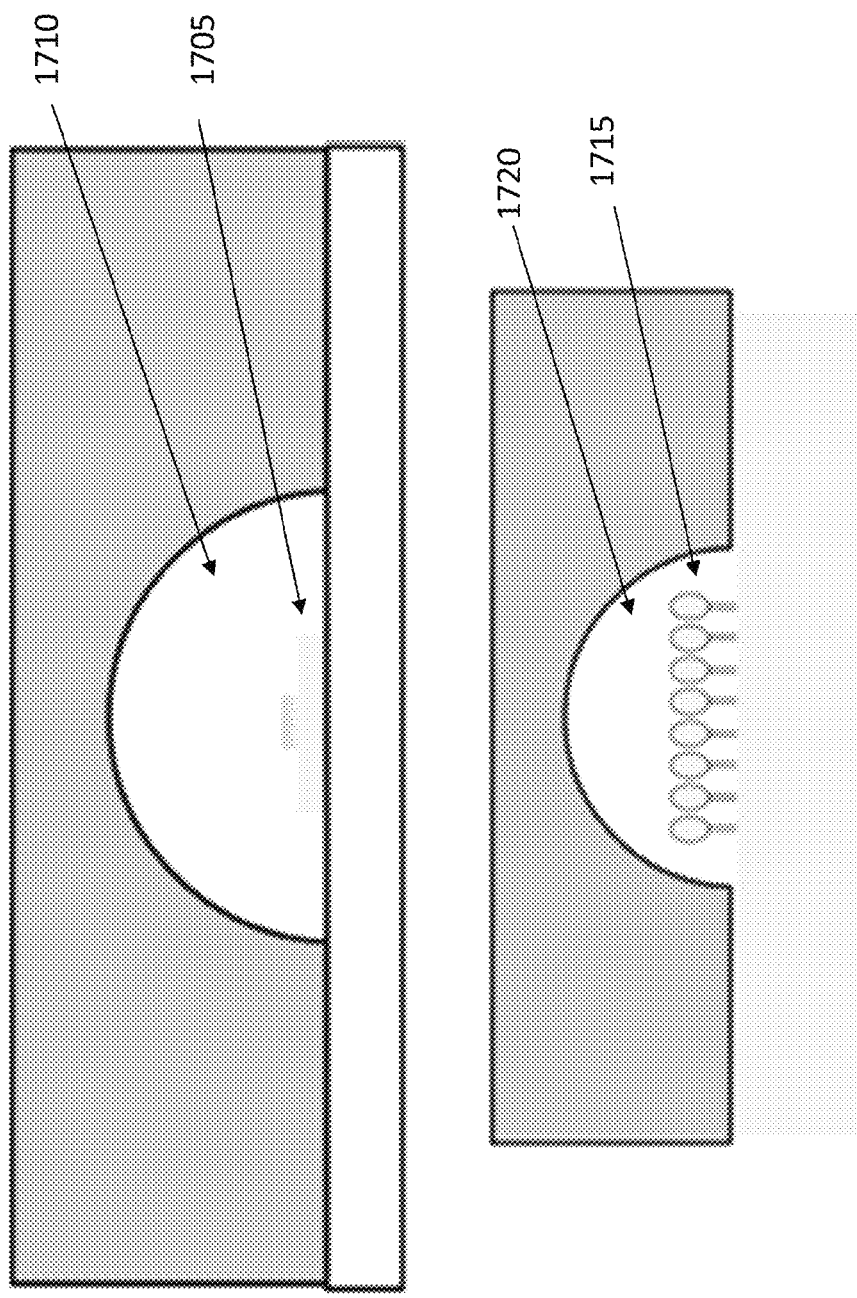
FIG. 17 illustrates an example of microfluidic chamber.

In some embodiments, measurements can be collected by placing the chips in a microfluidic environment above the Raman-sensitive chip. The microfluidic environment can encapsulate the whole chip, with the entire chip immersed in the liquid. In other embodiments, through soft lithography the microfluidics environment can be limited to an area above the sensing area as shown, for example, in FIG. 17. In FIG. 17, the sensor chip (1705) is within a microfluidic environment (1710). In other embodiments, the sensing area with nanopillars (1715) is within the microfluidic environment (1720) while a remaining part of the chip is outside the microfluidic environment (1720). A microfluidic environment may be, for example, a microfluidic chamber within a microfluidic device. In the configuration of FIG. 17 it is possible to carry out measurements on the chip in a microscope setting. In some embodiments, the microfluidic structure may be fabricated with other methods instead of soft lithography; for example, the microfluidic structure may be fabricated by pressing together cover slips and double-sided tape.

Figure 18:
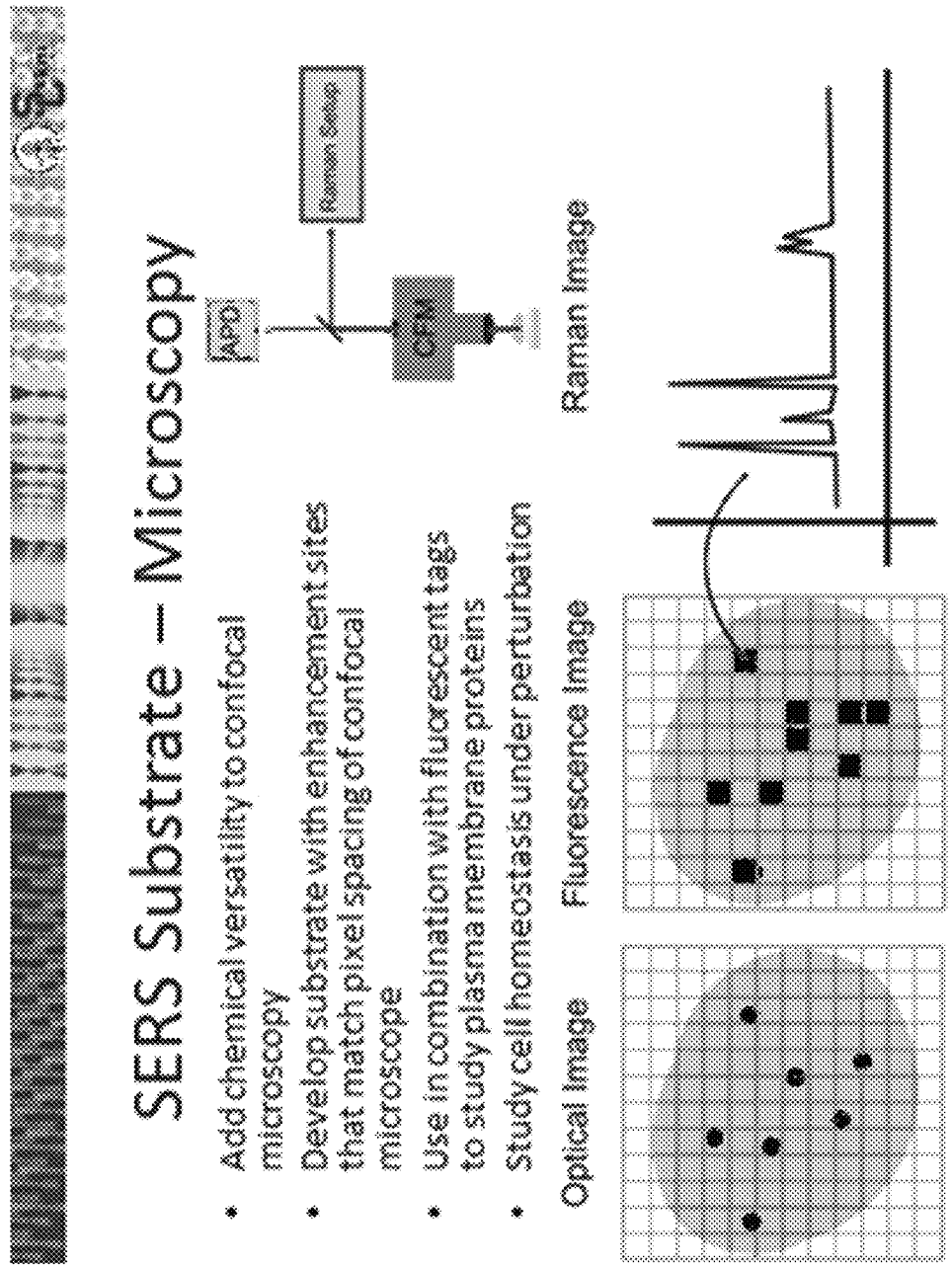
FIG. 18 illustrates microscopy measurements.

In some embodiments, the substrate itself can be used to add a chemical sensing mechanism to confocal microscopy as illustrated in FIG. 18. This method would be useful for interrogating features on cell membranes that have been fluorescently tagged. For example, the substrate can have enhancement sites that match the pixel spacing of a confocal microscope. In this embodiment, the enhancement sites on the substrate are fabricated with a spacing matching the spacing of pixels in the microscope view. This method can be used together with fluorescent tags.

Figure 19:
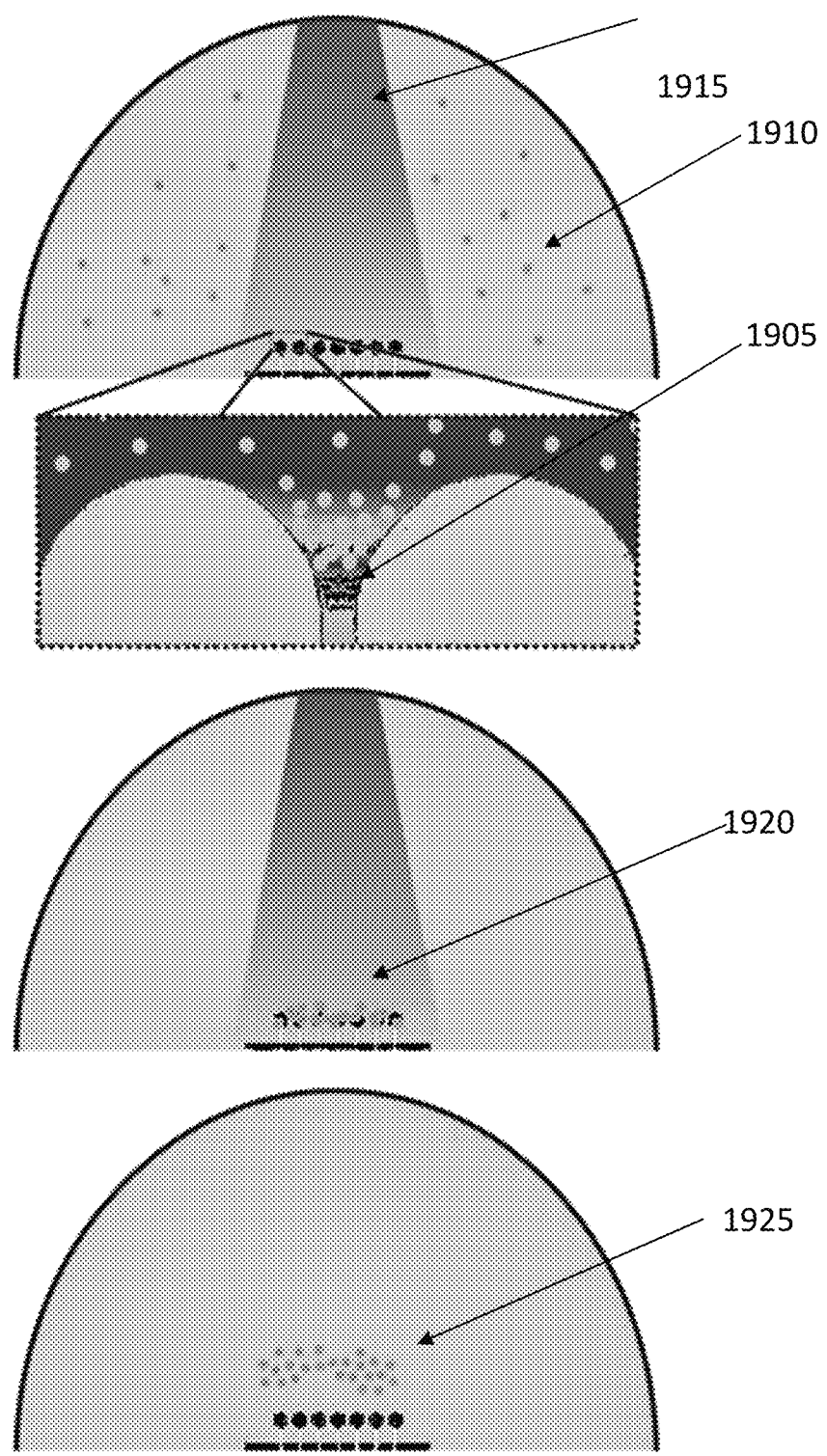
FIG. 19 illustrates a method to concentrate molecules.

In some embodiments, the sensor can be used as an optical trap, as illustrated in FIG. 19. The highly confined light in the nanogap apertures (1905) between bulbs on the nanopillars can act as a gradient electric field to capture free-floating biological molecules (1910). This embodiment can be used to concentrate diffused molecules or targets by passing a solution over the 'sticky area' multiple times while a laser (1915) is illuminating the nanostructure. Subsequently, the laser can be turned off and the targets would diffuse away to be resuspended in a much smaller volume of solution. Through the steps of localization close to nanopillars (1920) and subsequent resuspension (1925) in a smaller volume of liquid, the overall effect is to increase the concentration of molecules in the solution. In FIG. 19, the volume of solution is unchanged, therefore the average concentration does not vary, although the molecules are temporarily localized in an area before eventually diffusing away. However, in other embodiments part of the liquid can be removed from the microfluidic environment, or the volume of the liquid can be decreased by decreasing the size of the microfluidic reservoir and pushing part of the liquid solution out of the microfluidic environment.

In other embodiments the SERS substrate can be used as a peptide or protein sequencer. Proteins/peptides can be dragged through the electric field maxima, similarly to the embodiment of FIG. 19, by using optical tweezing or microfluidics techniques, while the Raman signal from this area is recorded. By tracking unique features of the Raman signal and correlating it with the position of the molecules it is possible to sequentially extract the structures that are passing through the field maxima.

Figure 20:
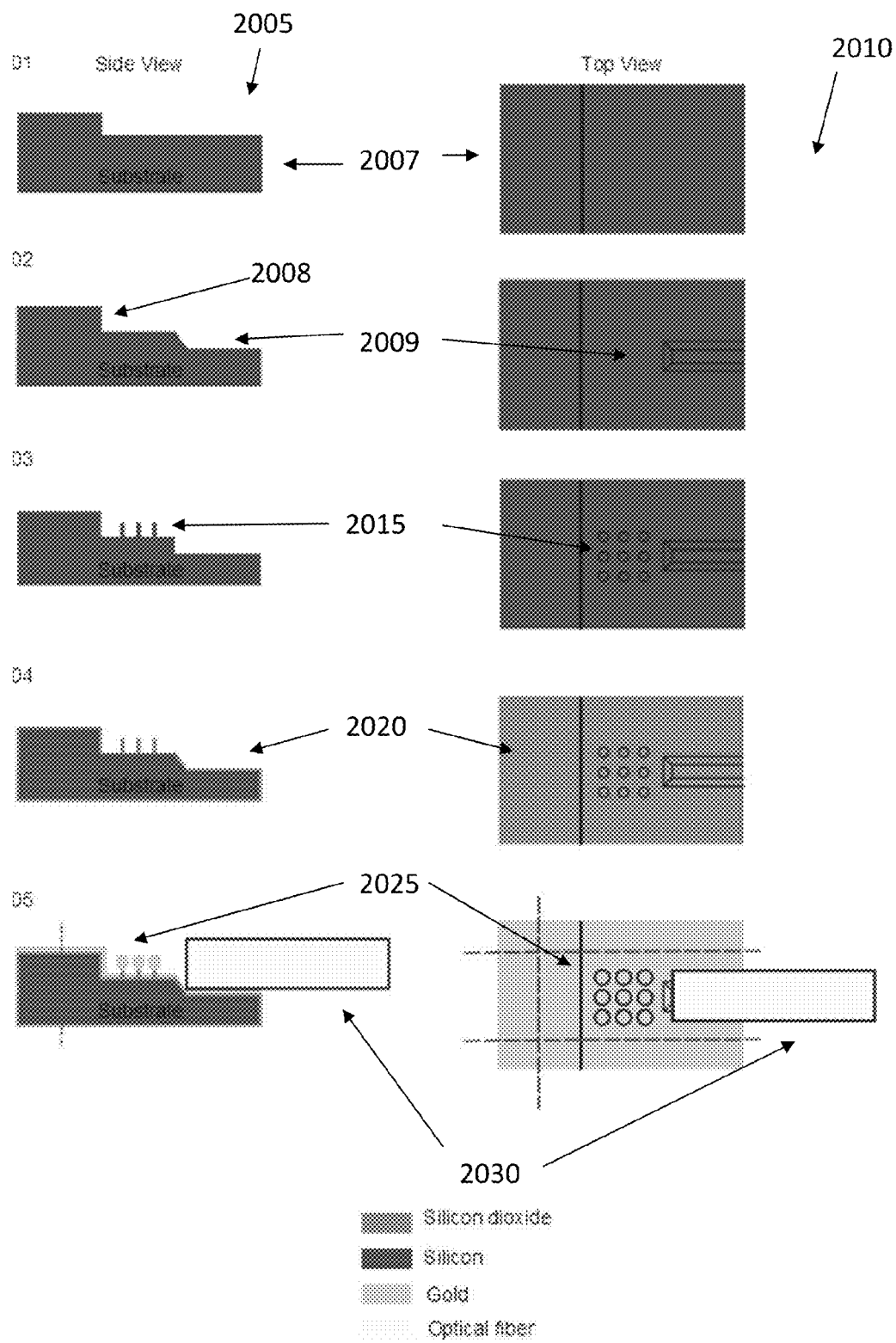
FIG. 20 illustrates fabrication steps for a sensor.

In some embodiments, and as illustrated in FIG. 20, optical fibers can be integrated into the chip in a mesa-like structure, for example with the following fabrication steps:
1) Cryo etch to define the mesa region for the sidewall reflector;
2) KOH etch to define the V groove for the optical fiber;
3) Pseudo Bosch etch for nanopillars;
4) Thermal oxidation; and
5) Au sputtering, thermal annealing, and fiber attachment (dotted lines indicate chip truncations with a laser scriber).

The person skilled in the art will understand that variations of the above fabrication steps can be carried out, for example etching with a different agent instead of KOH, or using wet etching instead of cryo etching. An exemplary flowchart of fabrication steps is illustrated in FIG. 20, both in side view (2005) and top view (2010). A recessed region is etched (2007), for example by cryo etching. The recessed region will have a side mesa (2008) which acts as a reflector for the optical fiber installed in a subsequent step. A V groove for the optical fiber is defined in the substrate (2009), for example with KOH. The substrate may be made of silicon. Subsequently, the nanopillars can be defined in the substrate, in the recessed region (2015), with methods described above in the present disclosure. For example, a pseudo Bosch process can be used. The top surface of the structure can then be oxidized, forming silicon dioxide in this example (2020). A metal, for example Au, can be deposited on the structure (2025). The optical fiber (2030) can then be attached to the structure.

Figure 21:
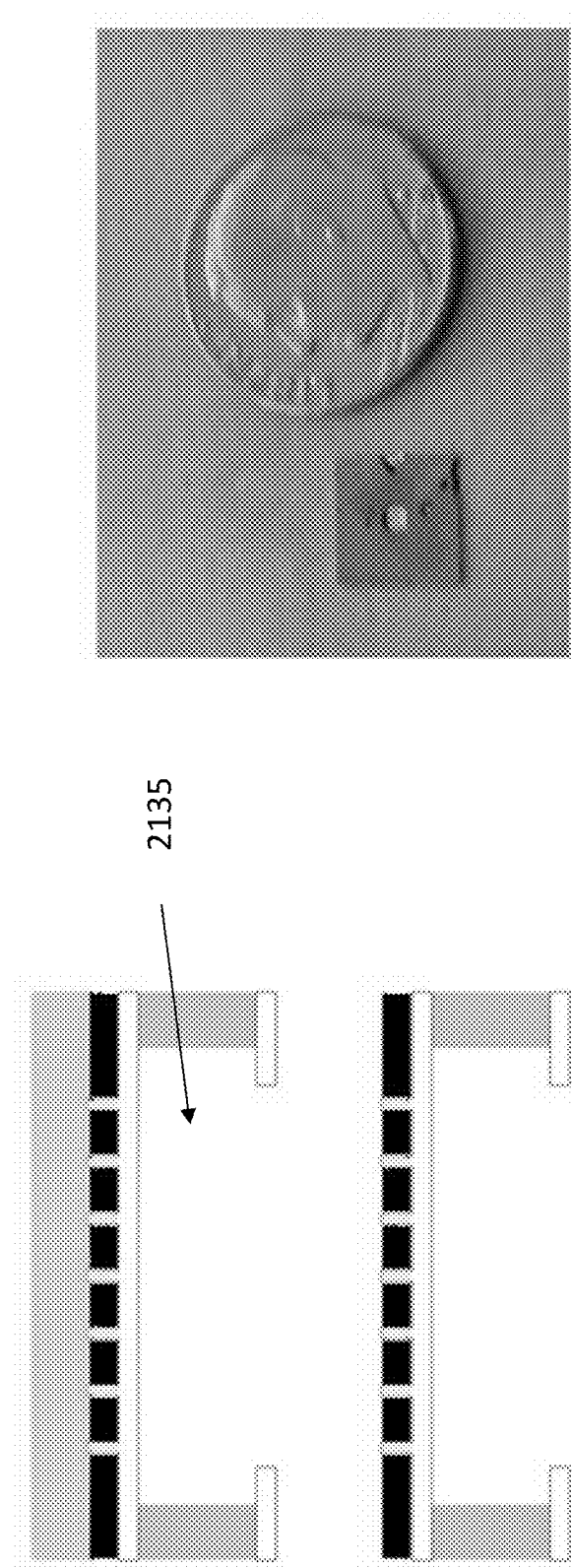
FIG. 21 illustrates fabrication steps for nanopillars on an optic fiber.
Figure 22:
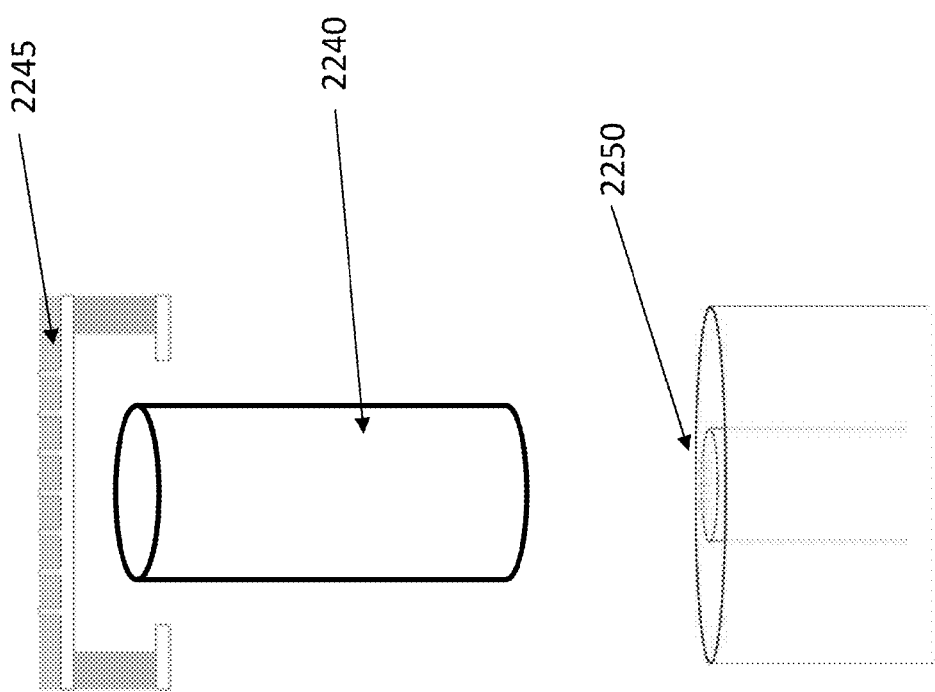
FIG. 22 illustrates further fabrication steps for nanopillars on an optic fiber.

In other embodiments, a remote sensing system that eliminates the chip altogether can be fabricated as, for example, illustrated in FIG. 21. Using methods known to the person skilled in the art, a hole can be cut through the silicon substrate (2135). For plasmonic devices a window from the front to the backside of the chip can be fabricated. This method can be carried out by masking the front of the chip with a polymer, patterning a square on the back of the chip, and etching through the silicon dioxide with buffered HF and through Si with XeF2, for example. As shown in FIG. 22, fiber (2240) can then be pushed through the hole in the chip to lift the pillars off (2245). The final device is a fiber with nanopillars on the end surface (2250).

Figure 23:
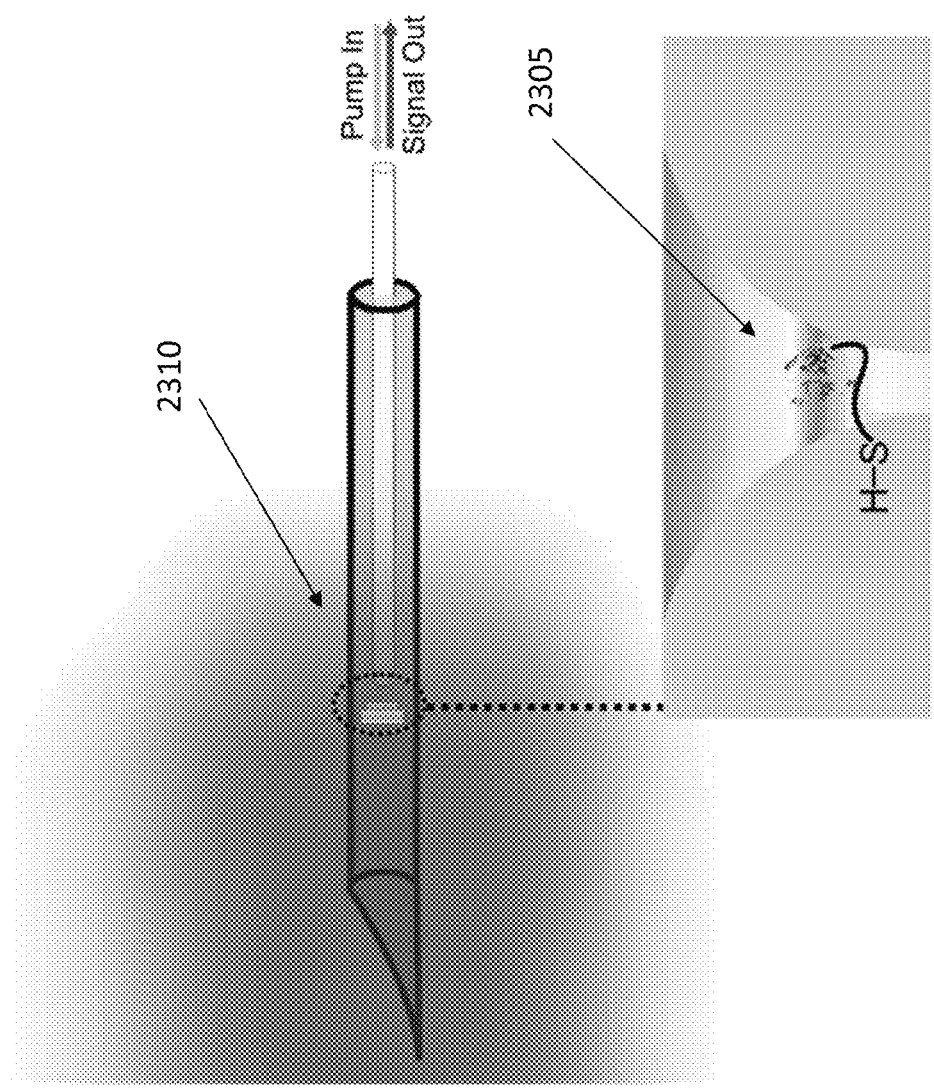
FIG. 23 illustrates fabrication steps for nanopillars on an optic fiber with a needle.

In one embodiment, the nanopillars with bulbs that act as enhancement tips are sitting within the core of the optical fiber. In this embodiment, the nanopillars are on the illuminating end of the fiber, where the laser light exits and enters the fiber. Since, in some embodiments, the pillars are only one micron tall, they are well within the acceptance angle of the fiber and can be used to efficiently measure SERS signals. The fiber can work both as the pump and the signal extraction mechanism. The gold normally found on the region below the pillars can be removed chemically or by using a thinner initial metal thickness, which would wick up onto the tops of the pillars. Such a device could have applications, for example, in remote sensing of inorganic nitrogen for explosives detection or soil monitoring or in remote, endoscopic chemical detection within organisms. The fiber can also be placed within a needle for blood-based or in vivo measurements, as illustrated in FIG. 23. In FIG. 23, an optical fiber with nanopillars is attached to a needle (2310), and a close up view of the gap between bulbs on the nanopillars is illustrated (2305).

Devices incorporating nanopillars in implantable sensors, or sensors that can attach to devices which can be injected, temporarily or permanently, can be very helpful in detecting different types of diseases, such as cancer and infectious diseases. Early detection of cancer and infectious diseases can be critical to saving lives and utilizing the least invasive treatments. To detect a disease early, a clinician may look for biological markers (e.g., proteins, mRNA, cytokines, etc.) in a patient's tissues or fluids, such as blood or saliva. Unfortunately, most diseases do not present one unique marker, but an entire constellation of molecular markers, each requiring its own preparation and testing for identification. The methods and devices of the present disclosure can provide a label-free method to detect this marker constellation in a single test—providing unambiguous, early indication of a disease. One detection method that can be used, as described above, is Raman spectroscopy. In Raman spectroscopy, the vibrational and chemical make-up of molecules is probed via laser light. Nanofabrication can be used to amplify the Raman signal 10 billion-fold by creating unique 'nano-bulb' surface enhanced Raman spectroscopy (SERS) substrates, as described above in the present disclosure. As described herein in various examples, these substrates can be sensitive enough to track single aptamer-molecule binding events. In the following, further embodiments and examples are described. Two model diseases used in the following are *Bordetella pertussis* (whooping cough) and oral cancer. Both diseases can be managed if caught early, but are often found only once severe symptoms emerge.

In some embodiments, functionalization methods can be used to expand the range of analytes that can be detected with nano-bulb chips. For example, the individual binding of two oral cancer markers—interleukin-8 (IL-8) protein and IL-8 coding mRNA—can be quantified individually, by functionalizing the gold nano-bulbs on several chips with an IL-8 antibody (AB) to detect IL-8 protein and with cDNA to detect the IL-8 coding mRNA. This individual quantification can be followed by multiplexed sensitization to quantify binding of both markers, simultaneously, from a mixed sample. Furthermore, evolutionary selection can be used to create probes, such as aptamers or ligand probes, to detect tracheal cytotoxin (TCT), the epithelium-destroying secretion of *B. pertussis*. Understanding TCT secretion from cultured *B. pertussis* during growth can help decrease Pertussis-related injury to the lungs. Training in functionalization, probe design, and cell culture from these projects can be used to expand the scope and utility of these sensors in other applications.

In some embodiments, the methods of the present disclosure focus on multiplexed and portable sensing. A bacterial sensor can be used, for example, to monitor shifts in *B. pertussis* phenotype via protein expression; study of this effect can allow for targeted treatment to reduce virulence and transmissibility of whooping cough. Multiplexed functionalization can also be used to simultaneously detect eight key pre-oral cancer markers from a single saliva sample. In other embodiments, SERS diagnostics can be expanded beyond the lab using hand-held Raman spectrometers and microfluidics to create field-based assays and fabrication to put a sensor on the tip of a fiber for in-vivo, endoscopic measurements.

The methods and devices described in the present disclosure serve as an important early step in the long-term research goal of linking electro-optical sensing to the needs of diagnostic medicine. Key biological techniques combined with nanofabrication approaches can allow for sensor design with distinct levels of complexity for the lab, hospital, clinic, or field.

As described above, to find all markers pertaining to a disease, normally the blood has to be fractionated and different tests for each molecule type must be performed, delaying diagnosis. The present disclosure describes instead a label-free method to quantify an entire constellation of markers in one test. The use of surface enhanced Raman spectroscopy (SERS) provides direct chemical information about the markers for unambiguous detection. Specifically, the sensitivity of the 'nano-bulb' SERS substrates is exploited to make a multiplexed, lab/clinical based sensor.

For example, an early detection assay can simultaneously detect two pre-cancer markers. In a first step, the sensor can detect and quantify IL-8 protein and IL-8 coding mRNA (both pre-cancer markers in saliva) by functionalizing the SERS substrate with antibodies or cDNA. Quantification can be done by calibrating relative intensities of unique analyte/functionalization peaks against known concentrations. In a second step, photo-uncageable linkers can be used to selectively functionalize half the bulbs (the metallic structures on the nanopillars) with antibody and half the bulbs with cDNA to simultaneously detect both IL-8 protein and IL-8 mRNA in a mixed sample—a first step toward building an early disease detection device.

Additionally, it is possible to measure tracheal cytotoxin (TCT) secretion from in vitro *B. pertussis* (Bp) colonies. TCT secreted by Bp during cell division is responsible for epithelial damage to the lungs in "whooping cough" and is a unique infection marker. Currently a TCT binding molecular probe does not exist. However, it is possible to create an aptamer-based and peptide-based probe, using in vitro evolutionary selection methods, and use them for TCT detection. In a first step, it is possible to make and verify binding performance of probes separate from the sensor. In a second step, it is possible to functionalize the sensor with the probes, and use the sensor to quantify concentrations of TCT as described above. In parallel, liquid-gelling growth media and an incubator can be used for culturing Bp in vitro. By using nanofabrication techniques the sensor can be embedded in the top layer of agar. Subsequently, TCT release rate can be tracked in situ as compared to the time/growth phase using the probes.

In some embodiments, in situ measurement of *B. pertussis* secretions using phenotypic markers can be carried out. A detailed study can be carried out centered on the unique 3-phase phenotypic regulatory system of *B. pertussis* known as BvgAS. Based on certain environmental conditions, the BvgAS system shifts the bacteria between dormant, infectious, and virulent phenotypes, each with a unique protein profile. The implanted sensors described in the present disclosure can be used to look for the current phenotype through detection of the secreted proteins. Aptamers can be evolutionarily selected to bind these proteins. Aptamers can be chosen to allow for "catch and release" measurements via optical heating so that the sensor does not become saturated and can remain in place during the entire experiment. A better understanding of the phenotypic regulatory process of Bp can allow for early detection and targeted treatment that can decrease virulence and transmissibility.

In some embodiments, multiplexed detection of constellations of markers for unambiguous disease detection can be carried out. Oral cancer presents several non-unique proteins and mRNA fragments whose simultaneous presence is a disease indicator. Through selective photo-uncaged functionalization, it is possible to create a multiplexed chip to quantify, for example, eight of these specific markers concurrently. Development of this sensor can follow an iterative path that leads to the creation of a new clinical early detection tool.

SERS is a powerful detection technique, but spectrometers and microscopes normally tether it to the lab. By using commercial, hand-held Raman devices, microfluidics, and multiplexing it is possible to perform infrastructure-free, field-based diagnostics for constellations of disease markers. Endoscopic sensors can be made with nanofabrication methods to place the sensor on the end of an optical fiber. Micron sized optical fibers allow sensor placement inside 30 gauge needles for in vivo analysis. These schemes extend the power of SERS detection beyond the lab or clinic and into the world.

In some embodiments, nano-bulb SERS detection methods allow the measurement of new bio-molecules under challenging mixed sample or in vitro conditions. Early disease detection is critical to saving lives and utilizing the least invasive or irreversibly damaging treatment procedures. For example, finding life-threatening cancers at the pre-cancer or carcinoma in situ phase can allow for endoscopic excision of the neoplasm before its progression requires treatment with radiation and chemotherapy. Similarly, early detection and treatment of respiratory bacterial infections can reduce permanent damage to the airway or lungs and reduce the duration of infectiousness to help prevent disease transmission. In addition to improving patient health, early detection can reduce health-care costs for both hospitals and patients through simpler treatments and preventative care. Current "detection methods" (ELISA, qPCR, etc.) are analyte specific; therefore, to find a marker pattern typical of a disease, a fluid sample must be fractionated, precipitated, and tested separately for each individual type of marker—a time and cost prohibitive method.

For example, oral cancer is a form of head and neck cancer that is indicated by cancerous growth within the mouth. Around the world more than 125,000 people die per year as a result of this disease. In America, of the approximately 37,000 people diagnosed with oral cancer each year, about two-thirds will be diagnosed once the cancer has entered late stage III or stage IV of growth, resulting in a 62% five-year survival rate. However, if detected early and treated with life-style changes or pre-cancer targeted excision, the prognosis improves dramatically. To that end, there have been a great number of studies to determine various correlated pre-cancerous markers, but no method to detect these marker constellations simultaneously in a clinical setting.

As another example, whooping cough is caused by the epithelial damage done to the respiratory tract during a *Bordetella pertussis* infection. Around the world, approximately 45 million people contract the disease and approximately 300,000 die each year, with the highest mortality rate in infants less than 4 months old. Internationally, it is the leading causes of vaccine preventable death. Even amongst the well-vaccinated American populace, the rate of infection is on the rise—represented by focal outbreaks in California (in 2010), Washington and Vermont (in 2012)—with the highest rate of infections since the 1950s. Early treatment can cut mortality, shorten the infectious period, and abate respiratory tract damage. However, due to a partially vaccinated populace and the typical delay in seeking treatment, current methods of detection, including qPCR and culturing, can be ineffective for early detection. Therefore a new, direct oral or serological detection method is needed for early diagnosis.

As yet another example, real-time data on changes in phenotypic phase in response to environmental conditions can provide a unique window into the adaptation mechanisms of a bacterial colony. For example, the bacteria *B. pertussis* has a unique regulatory system which transfers the bacteria between dormant, highly transmissible, and maximally toxic phenotypes. Unfortunately, the lack of animal models and the inability to track phenotypic specific secretions in situ has left scientists in the dark as to what environmental conditions propel the bacteria from phase to phase—even to the point that there is no consensus on what causes the "whoop" or the cough in whooping cough. The devices described in the present disclosure can enable a method to track the bacteria's phenotypic state in real-time, in situ and in vitro, to obtain a greater understanding of the possible in vivo bacterial growth cycle to inform methods for early detection and eradication.

One detection mechanism in the present disclosure is Raman spectroscopy. In Raman spectroscopy, laser light is scattered off a molecule and returns at a different wavelength, having donated or accepted energy from a vibrational mode. The wavelength differences between the incident and collected light gives unique information about the molecule's chemical bonding, conformation and atomic species; by collecting a spectrum of these shifts, it is possible to essentially find a "chemical fingerprint." Unfortunately, Raman is a very weak effect, returning 1 photon for every 10 million input photons, and requires long collection times (minutes) and intense lasers (~500 mW) to produce spectra. However, as described above, by creating nanostructured metallic surfaces it is possible to amplify this effect in a technique known as surface enhanced Raman spectroscopy (SERS).

For example, the gold "nano-bulb" SERS substrate of FIG. 1 can show a 10-100 billion-fold enhancement in signal over standard Raman measurements. When combined with aptamer sensitization of the gold bulbs, it is possible to measure sub-clinical concentrations of proteins, for example measuring 100 pM to 500 fM concentrations of thrombin as illustrated in FIG. 24. The measurements represented in FIG. 24 were not taken by inference, such as tracking a binding related shift in a sensor property such as an optical resonance or threshold voltage. Instead, when the thrombin is captured by the aptamer, it is possible to see in the SERS spectrum, unique chemical structures only found in the thrombin that was not present before binding. Furthermore, the measurements in FIG. 24 were taken with 1 W of laser power and 5 second collection times; a great improvement over standard Raman sensing.

Previous Raman or SERS methods have had difficulty in performing concentration measurements based on absolute signal intensities. This stems from the fact that the signal intensity of both of these spectroscopic techniques can be heavily dependent on particular optical excitation and collection conditions, and SERS can also be dependent on the location-specific enhancement factor. Therefore, particularly for SERS, it can be difficult to have an "apples to apples" comparison when comparing concentration measurements on different chips or even different locations on a single chip. In the present disclosure, a method is described to perform "relative peak quantification," that takes advantage of the fabrication methods of the present disclosure to normalize chip to chip or optical variability.

For example, quantification can be performed by first finding unique Raman peaks associated with (1) the molecular probe and (2) the target molecule. In some embodiments, these peaks were (1) the thrombin binding aptamer (TBA) and (2) thrombin. After determining unique TBA/thrombin peaks, solutions with known concentrations of thrombin can be applied to the substrate and the SERS spectrum can be taken at a random location. At each thrombin concentration the same thrombin specific peak intensity can be compared to the TBA specific peak intensity and this ratio can be plotted with respect to thrombin concentration. It is thus possible to find that the thrombin:TBA peak intensity ratio scales linearly with thrombin concentration. Therefore, when analyzing a sample with an unknown concentration of thrombin, the concentration can be deduced by finding the relative SERS peak ratio and locating where it sat on the concentration curve. For example, data collected at 1-100 pM concentrations on three separate chips is shown in FIG. 24.

Despite the random selection of measurement points and slight differences in enhancement factors between chips, the relative peak intensities scale identically with thrombin concentration (2405), as can be seen in FIG. 24. This quantification method is based on two unique features. The first feature is the ability to measure both the "yardstick" and "target" peaks in a single measurement. By measuring both the TBA and thrombin peaks in a simultaneous measurement, any optical measurement imperfection (misalignment, defocusing etc.) applies equally as a transfer function to the signal from both species; scaling both peaks but not scaling their relative intensities. By taking a 5-10 s measurement any differential contributions based on probe gyration can also be averaged out.

The second feature is that each binding site within the laser spot can be "equal" (as in has a similar enhancement factor). Since the substrates used for the measurement of FIG. 24 were created through deterministic fabrication and not through stochastic "hot-spots", the enhancement factor within the laser spot was uniform with respect to binding sites. Therefore, each additional bound thrombin located in a field maximum contributed equally to an increase in the relative intensity of its unique peak. It can be shown that this is a reasonable estimate for the substrates by raster scanning to collect the SERS signal from a thiophenol marker and finding less than 5% variability in enhancement factor over an entire 100 μm square pad of nano-bulbs.

In FIG. 24, the top graph (2410) illustrates the evolution of 500 fM thrombin addition. Some peaks are shifted (2415) and some peaks (2420) are new thrombin specific peaks. The graph on the left (2425) illustrates the intensity ratio of thrombin, thrombin binding aptamer (TBA) vs thrombin concentration on 3 separate chips. The graph on the right (2430) illustrates optical denaturing and recovery of TBA. Guanine peaks are blue-shifted due to reduced steric hindrance, while conformation dependent peaks disappear during denaturing and reappear during TBA recovery.

To extend single analyte chips to multiplexed/multi-biomolecule detection a combination of a photo-uncageable linkers and photo-lithographic techniques can be used. The process, an exemplary embodiment of which is illustrated in FIG. 25, can begin by the functionalization of the gold nano-bulbs (2510) with a thiol-alkane-amine (TAA) linker (2505). A variant of coumarin, {7-N,N-diethylamino 4-hydroxymethyl coumarin caged glutamic acid} (DECM-CG) can then be attached (2515) to the amine (2505). To prevent non-specific binding any uncomplexed TAA can be passivated with acetic anhydride (2520). Photolysis of the DECM-CG can be performed with light at wavelengths between about 350-410 nm, conveniently capturing two common photo-lithographic exposure lines (365 nm and 405 nm). A photo-lithographic mask can be used to expose a certain area of functionalized nano-bulbs releasing the DECM-CG, re-exposing the amine in that region (2525). A molecular probe can be attached to the amine group followed by acetic anhydride passivation of any left-over amine groups. Then a new area will be uncaged by the photo-mask, functionalized and passivated, and so on, iteratively. At each functionalization step, completely different binding agents, such as antibodies, aptamers (2530), cDNA, etc., can be attached creating a multiplexed/multi-molecule sensor. While this repetitive process may seem time intensive to perform on a single-chip, using the parallelism of wafer scale lithography thousands of chips could be sensitized simultaneously.

As will be understood by one skilled in the art, various suitable linkers and passivating agents may be used in the methods above. For example, the TAA linker may be replaced with any suitable linker comprising an amine group, and the DECM-CG can be replaced with any suitable photo-uncageable linker. Additionally, any appropriate passivating agent may be used instead of the acetic anhydride. Furthermore, the above steps of creating a multiplex sensor need not be performed on a chip as illustrated, for example, in FIG. 1 of the present disclosure. Any suitable substrate may be used to attach the amine-comprising linker and then the photo-uncageable linker to the amine linker. For example, a silicon or glass surface may be used in the method of fabricating a multiplex sensor as described above.

In some embodiments, the unique reflow fabrication process described in the present disclosure allows to make wafer scale arrays of gold nano-bulb SERS sensors with tunable enhancement gaps, for example from 5 to 30 nm. In some embodiments, these structures have demonstrated average SERS enhancements of up to $10^{11}$ over 100 μm scale pads of pillars, and through aptamer functionalization these structures have detected thrombin at femtomolar concentrations—4 orders of magnitude below clinical levels, as described above.

In some embodiments, the SERS sensors can detect two correlated oral cancer markers with single chip, multiplexed SERS. One of the oral cancer markers is Interleukin-8 (IL-8). In some embodiments, a first step comprises functionalizing the gold nano-bulbs on several chips with an IL-8 antibody (AB). A possible gold attachment method is through AB thiolation, but other methods can be considered based on AB size and specific residues/moieties. After functionalization, microscope-coupled SERS can be performed within a fluidic environment containing appropriate buffers to determine the unique spectral features of the antibody. Subsequently, IL-8 protein can be introduced over the sensitized chips at known sub- to supra-clinical concentrations found in patients at risk for oral cancer and spectral features unique to IL-8 residues/moieties can be determined. For each concentration, the relative intensity of IL-8 vs. AB specific peaks can be considered to perform relative peak concentration quantification as described in the present disclosure. In another step, the detection specificity can be tested against other commonly coincident proteins due to oral cancer, such as IL-6 and IL-1. Another oral cancer marker is IL-8 coding mRNA. In some embodiments, the steps for detection of IL-8 coding mRNA are similar to those described above for IL-8 protein, but functionalizing with cDNA to bind the IL-8 coding mRNA. For functionalization, thiolated cDNA oligos can be commercially obtained; however, they are typically provided as two oligos linked by a disulfide bond. Methods to cleave this bond into two thiols, without re-oxidation, can be carried out through the use of biochemical tools such as reductants and de-salting columns to prepare DNA for functionalization. As with the protein measurements at several sub- to supra-clinical concentrations, measurements can be performed to determine the relative-peak quantification curve. To uniquely identify mRNA, one possibility is to determine the presence of Uracil and ribose sugars in the Raman spectrum. Specificity can be tested against other possible oral cancer mRNA markers, such as mRNA coding for IL-1B and a-TNF.

Figure 25:
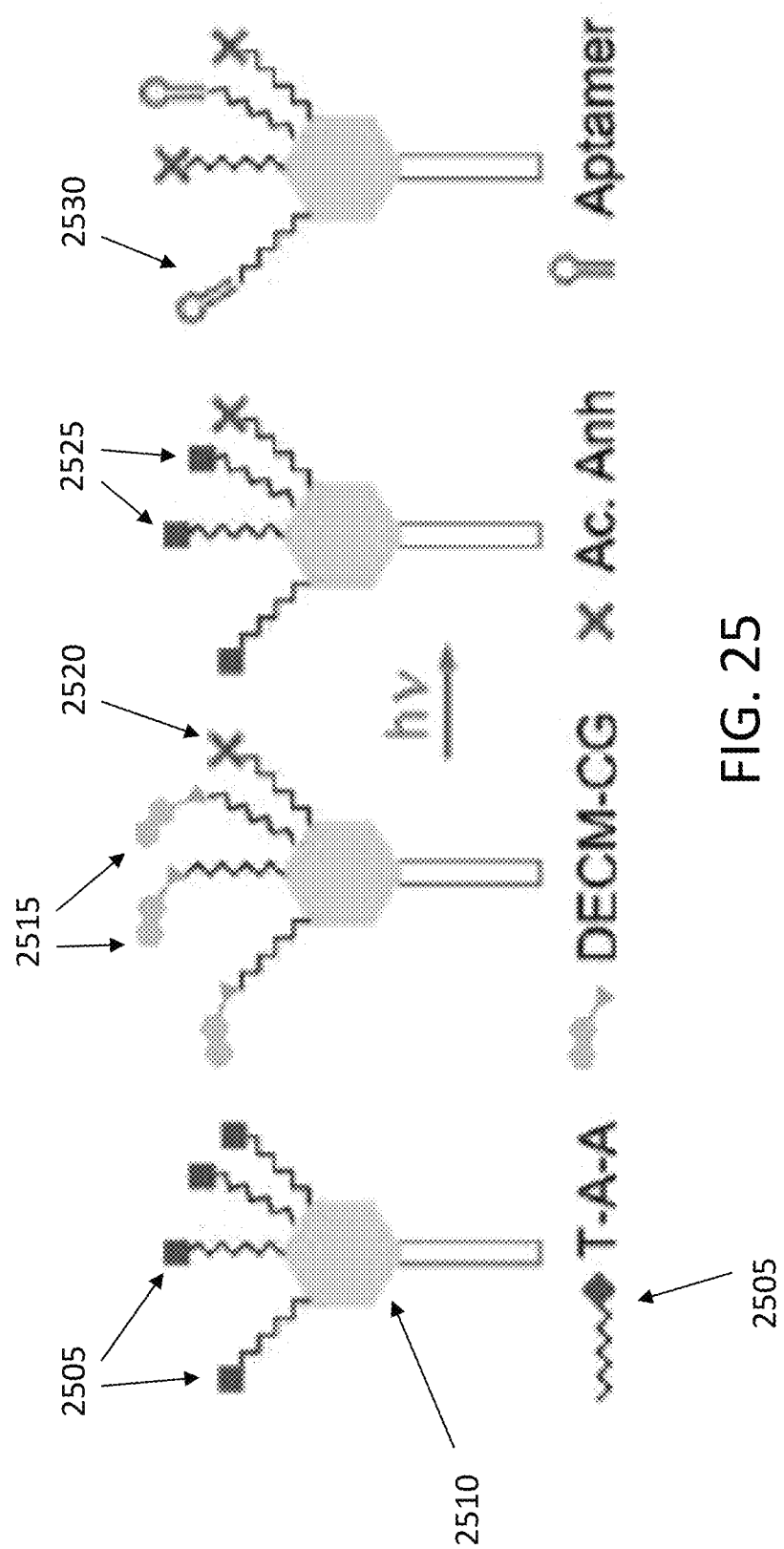
FIG. 25 illustrates different functionalization processes.

Subsequently, simultaneous, multi-molecule quantification using photo-uncageable linkers can be carried out. In this step the multiplexed functionalization method of FIG. 25 can be used to sensitize half the nano-bulbs on a chip with the IL-8 AB and half with the cDNA probe for IL-8 coding mRNA. After sensitization the chip can be placed in a buffered fluidic environment where SERS measurements can be taken of the molecular probes on each half of the nano-bulb array and compared to previously collected spectra to check for cross contamination during functionalization. Subsequently, IL-8 protein and mRNA can be introduced in a single mixed sample with the analytes at various concentrations that simulate baseline, pre-cancerous, and symptomatic oral cancer samples. SERS can be performed on both halves of the nano-bulbs and the relative peak intensity versus concentration results can be compared to those previously collected to check for any confounding effects of the photolytic functionalization. Finally, specificity can be re-verified by measuring the mixed sample after adding the same coincident mRNA/proteins from above.

In other embodiments, the IL-8 antibody might not be suitable for thiolation as linkers could push the AB out of the SERS sensing zone between bulbs. In these embodiments, an alternative probe can be used. For example, a recently created IL-8 specific aptamer could be used as a probe. This 44-mer hairpin can bind the IL-8 close to the bulb surface for effective SERS detection as seen with the TBA-thrombin system. Alternatively, custom aptamer/peptide probes can be designed as described below.

Under certain conditions, nucleic acids can nonspecifically physisorb onto gold surfaces, reducing both the accuracy of concentration measurements and the specificity against non-target mRNA. To prevent this, post-functionalization passivation of any empty bulb areas can be considered, with a mixture of short and long-chain alkane-thiols. This method can create a carpet to fill in the gaps between any probes, such as cDNA probes, and stop physisorption of nucleic acids such as mRNA directly onto the gold.

When uncaging the coumarin on the bulbs, UV light can become trapped between the chrome mask and gold substrate, exposing masked areas through multiple reflections. If this occurs, it is possible to substitute the chrome mask with an iron oxide mask which masks the chip through UV absorption instead of reflection and would therefore stop multiple reflections.

To measure tracheal cytotoxin (TCT) secretion from *B. pertussis* colonies, in vitro evolutionary selection of aptamer and peptide probes can be carried out. To detect TCT (the epithelial cell destroying toxin produced during *B. pertussis* growth) a probe that can bind it is necessary. To develop a TCT specific ligand, some possible methods can depend upon in vitro evolutionary selection. In these methods, a large, combinatorial library of ligands (e.g., DNA strands or peptides tethered to their coding mRNA) is exposed to the molecular target. Any candidates that bind to the target are isolated and purified. The exact method of the isolation depends on the technique used and the target molecule. The isolated DNA or peptide candidates are amplified (in the case of the peptide, via the mRNA tag) and the binding/isolation process is repeated with this new library. After several cycles of binding and amplification, the probes with the highest affinity will be preferentially amplified. These can be collected and sequenced; in the case of DNA, the sequence constitutes an aptamer and in the case of the mRNA the peptide translation constitutes a ligand probe. This selection can be performed at 37° C. to match future culturing conditions.

Figure 24:
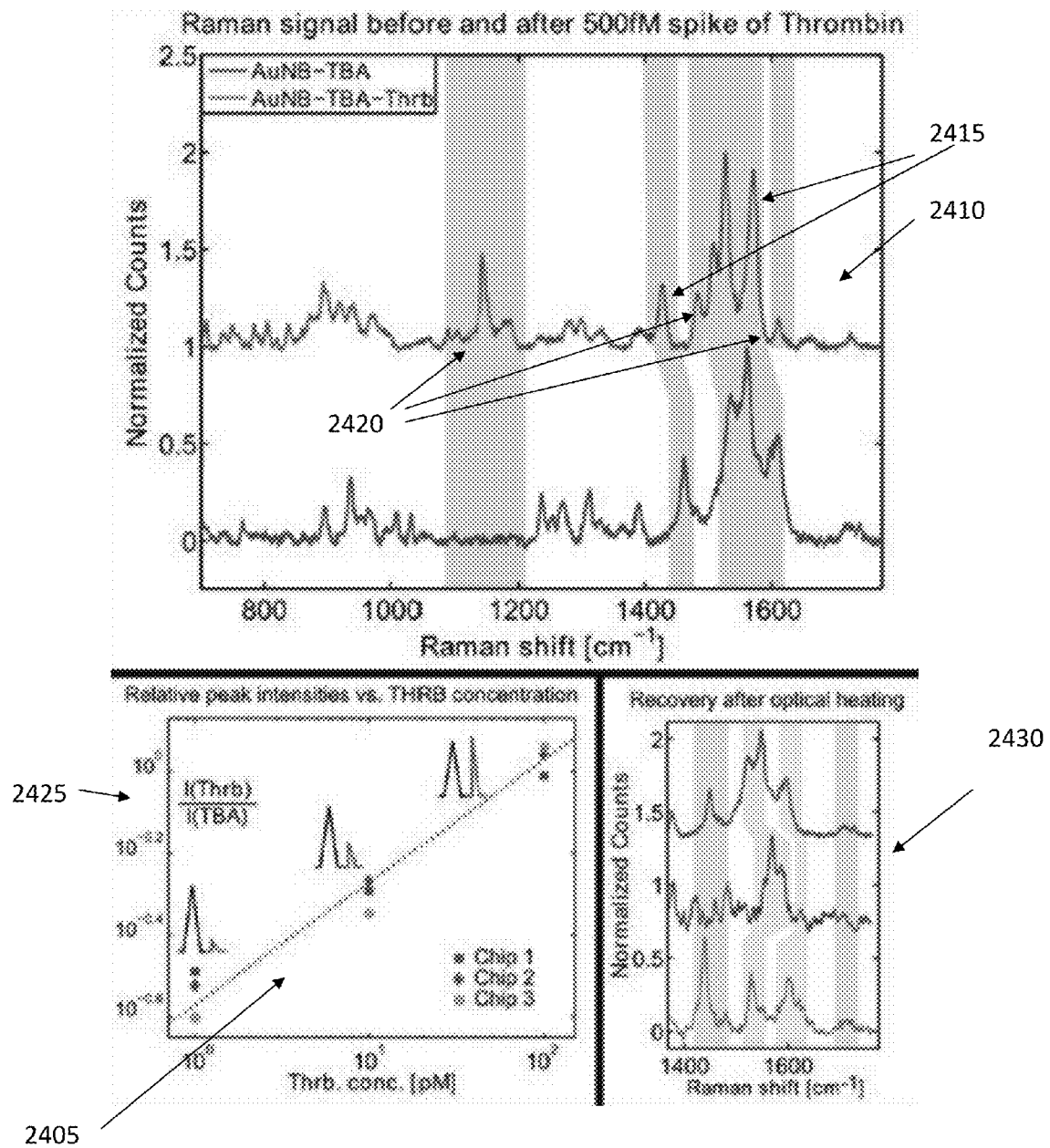
FIG. 24 illustrates measurements for thrombin experiments.

A next step in the above method can comprise a catching and releasing SERS detection of TCT using selected probes comprises quantifying the detection of TCT with the two probes developed in the previous sub-aim. This step can be done with a microscope using commercially available TCT. In a first step, the functionalization of the sensor with one of the probes can be carried out, subsequently taking its SERS spectrum in a buffered fluidic environment at 37° C. to find the probe's characteristic Raman peaks. In a next step, TCT can be introduced at various known concentrations and the previously mentioned relative peak intensity vs. concentration relationship can be calculated. Using this data it is possible to obtain an estimate of the limit of detection (LOD) of each probe when coupled to a nano-bulb SERS chip. In a next step, a second measurement can be taken where, with a known concentration of TCT in the fluidic chamber, the SERS chip is exposed to a 488 nm pulse of light to rapidly and locally heat the nano-bulbs and denature the probe. The conformation recovery of the probe can be tracked, and the return of the probe plus target signal can also be tracked. This "catch and release" type aptamer recovery is similar to that of FIG. 24 with the TBA-thrombin system. In some embodiments, a chip can spend an extended period of time in a cell-culture environment; to prevent probe saturation and to find an accurate measure of the current concentration of TCT, one can flash the chip and measure the concentration immediately after recovery. The best performing probe from these two tests described above can be used for future ex- and in-vitro sensing.

To carry out cell culture of *B. pertussis* for TCT extraction and testing, the following steps can be taken. In a first step, *B. pertussis* can be cultured for TCT time correlated extraction and detection. Agar plates can be prepared, for example, with standard 15% sheep's blood Bordet-Gengou liquid setting medium. This liquid component can be rendered transparent. In some embodiments, seventy plates can be streaked with commercial *B. pertussis* and incubated at 37° C. for 1-14 days. Each day, 5 plates can be selected and imaged to determine the stage of colony development. Subsequently, the cells/agar (from individual plates) can be centrifuged and the supernatant collected and passed through a 0.2 μm filter to remove gross debris. The resulting liquid can be passed over the SERS chips sensitized with the TCT probe. The concentration of TCT in the liquid extract from each plate can be measured based on calibration standards developed in previous aims. With a successful measurement it is possible to track the concentration of TCT vs. incubation time to understand at which point during infection *B. pertussis* causes the most damage to respiratory epithelial cells.

In some embodiments, steric hindrance or charge neutralization at the metallic surface can cause selected probes to exhibit reduced binding efficiency after attachment to the gold bulbs. There are some possible solutions to obviate this problem. For direct attachment to the gold, the thiolated end can be switched to the other side of the probe to allow for better folding without hindrance. Alternatively, a thiol-alkane-amine linker can be used to tether the probe far enough from the metal to allow for correct folding and to avoid charge neutralization. Alternatively, a modified version of the selection process can be performed, starting with the library of probes already attached to a gold surface. Using a bead based sequestration technique it can be possible to segregate the binding candidates from the gold surface and amplify them. With this method, probes can be explicitly designed to take into account metallic surface effects.

In the following passages, the skewed concentration that results from cell wall polymers is discussed. TCT in a polymeric form makes up the cell wall of *B. pertussis* and other gram negative bacteria. In some embodiments, the biological entities of interest are the free TCT monomers which cause epithelial cell degradation. In some embodiments the probes have selectivity to the TCT monomer over the polymer due to size and conformation differences. In some cases, however, cell wall fragments may be bound. This issue may be approached with a direct or indirect approach. One example of a direct approach is to explicitly add a step in probe design that selects against cell wall polymers: once likely candidates have been selected with affinity to TCT it is possible to add a TCT polymer binding step and remove the probes with affinity to the polymer, amplifying the rest. One example of an indirect approach is to compare SERS spectra of monomer/probe vs. polymer/probe binding and find peaks that are only present in the monomer/probe case. With this method, relative peak quantification can still be used to determine TCT monomer concentration in a mixed sample.

In some embodiments, in situ measurement of *B. pertussis* secretions can be carried out to understand phenotypic regulation. These embodiments focus on detailed study of the unique 3-phase phenotypic regulatory system of *B. pertussis* known as BvgAS. Based on environmental conditions the BvgAS system moves the bacteria between a dormant (Bvg−), infectious (Bvgi), and virulent (Bvg+) phenotype.

Some embodiments are directed at developing growth medium with implanted sensors. In some embodiments, the method to embed the sensor in the growth medium relies on the following steps. The agar plate can be prepared in two steps: first preparing and setting a standard Bordet-Gengou plate, and subsequently, using a photoresist spinner, it is possible to coat a thin layer (for example about 300-500 nm) of a translucent, blood-free B-G agar on an un-sensitized SERS chip, allowing the bulbs to protrude from this layer. High-pressure RF oxygen plasma can be used to clean any excess agar off the bulbs prior to functionalization. Subsequently, it is possible to spin a thicker layer of blood-free agar on the pre-set plate (for example, about 300 μm) and as it sets, place the coated chip in the layer. Since the chip is approximately 350 μm thick it will protrude from the spun layer; as the agar is setting it is possible to "paint" the edges of the chip with the liquid agar so that once it sets it will be locally flush with the spun layer. This can be done with several SERS sensors on a single plate to simultaneously monitor several colonies.

In some embodiments, in situ measurement of TCT during *B. pertussis* culture can be carried out with the following methods. Using embedded sensor plates developed in the previous steps described above combined with probes this method can track the emission of TCT from a single cultured colony of *B. pertussis* during various stages of incubation/growth. Prepared plates can be streaked with commercial *B. pertussis* taking care to ensure there is a possible culture in proximity to the embedded sensor(s). Plates can be incubated at 37° C. for 14 days. At predefined intervals (for example, about 4 times a day) plates can be removed from the incubator and each time the same colony can be measured. Measurement can consist of a) collecting data on colony size and shape to estimate the stage of bacterial growth, and b) using the above described "catch and release" SERS technique to measure the TCT concentration at the embedded sensor. The example choice of 4 measurement intervals per day is chosen based on the understanding that *B. pertussis* divides at relatively slow 6 hour intervals, but can be made more frequent as the experiment demands. This data can be compared with the ex-situ data collected with other methods described in the present disclosure, to determine the role of colony size on TCT production.

To develop probes for full phenotypic assay the following methods can be carried out. In the three phase BvgAS regulatory system, proteins or lack of proteins identify the current phenotype. The production of two proteins, filamentous hemagglutinin (FHA) and Pertussis Toxin (PTx), can serve as phenotypic indicators. Absence of both proteins indicates the dormant $Bvg^-$ phase; presence of PTx and FHA indicates the virulent $Bvg^+$ phase; and presence of FHA only indicates the highly infectious $Bvg^i$ phase. Methods of amplified selection and probe development at 37° C. can be used to create aptamer and peptide probes that correspond to these two proteins. Quantification of SERS detection, LOD determination, as well as "catch and release" performance can be completed as described above to determine the ideal probe for each protein that can detect low concentrations and survive repeated laser interrogation in cell culture environments.

In some embodiments, multiplexed embedded sensor can be used to track TCT and phenotypic phases. Methods for embedding the sensor, proximal streaking, and multiplexed functionalization based on photo-uncaging can be used to create agar plates with multiple, multiplexed, implanted sensors sensitized to track TCT, FHA and PTx. Following the 14-day in-situ procedure described above it is possible to track the phenotypic phase and TCT production of individual colonies as compared to colony size, shape, growth phase, and incubation time. Success in this aim is critical to understanding both the developmental progress of *B. pertussis* infections, and the conditions under which the bacteria begins to produce secretions that damage the epithelial tissue causing paroxysmal coughing.

Although the humidity of the incubator used to grow the bacterial cultures can be high to simulate respiratory tract conditions, the question remains if the water/extracellular fluid at the agar surface is sufficient to ensure correct folding of molecular probes. If it is found that the binding affinity of the probe is reduced under these conditions, it can be possible to add a translucent Stainer-Scholte, *B. pertussis* liquid growth medium on top of the plate. This medium has an ionic profile similar to the buffers used in selecting the molecular probes and is amenable to optical interrogation.

In some embodiments, the sensors described in the present disclosure can be used to simultaneously track a peptidoglycan (TCT), a filamentous protein (FHA), and an AB5 exotoxin (PTx) through the use of sensors embedded in agar plates. The secretion of these molecules from the *B. pertussis* bacteria can serve as indicators of its infectiousness, virulence, and toxicity. With an understanding of the phenotypic evolution over time it is possible to use this same sensor system to probe how outside influences (antibiotics, inorganic molecules, etc.) affect growth and phenotypic expression, a currently outstanding problem. Finding a method, benign to the body, that can trap the *B. pertussis* bacteria in the dormant phase can allow for a reduction in respiratory tract damage while antibiotics take their course. Additionally, by combining the multiplexing method with the methods described below, it is possible to create an early detection, rapid response assay to find these proteins in throat swabs or saliva. This assay can not only detect *B. pertussis* days faster than culturing methods but, based on the protein spectrum, indicate the current phase of infection. In other embodiments, the techniques described above for *B. pertussis* can be directly applied to study properties of any other cultured bacteria.

In some embodiments, multiplexed detection of constellations of markers for unambiguous disease detection can be carried out. For example, a sensor can quantify a panel of pre-cancerous oral cancer markers that can be used for pre-symptomatic detection in a lab or clinical setting.

In some embodiments, the following methods can be carried out to choose and individually test eight viable pre-cancerous oral cancer markers. In a first step, for example, eight possible markers and probes can be chosen. Some exemplary candidates can be divided by class: p proteins (IL-1, IL-6, IL-8, and TNF-a); mRNA (IL-8, IL-1p, DUSP1, OAZ1 and S100P); small RNA (miR-125, miR-200a, and miR-31); and Telomerases.

In some embodiments, four-fold multiplexed testing can be carried out. Using the photo-uncaging method described above it is possible to initially sensitize two SERS substrates, with four molecular probes on each, and test them against a mixed sample of the corresponding four markers at known concentrations; if there is no untoward interactions and individual marker relative peak intensity concentration curves are replicated, it is possible to proceed to test with a mixed sample of all eight markers on both four-fold multiplexed chips.

In some embodiments, full marker panel testing under lab, blind, and salivary conditions can be carried out. As described above, in a first step it is possible to functionalize a SERS substrate with the eight chosen marker probes and test them against known concentrations of the markers in a mixed solution. After verifying against known concentrations, it is possible to test with the researcher blinded against marker concentration and presence during the collection and analysis of the relative peak data. If the experimenter in the blinded study can use the relative peak method to deduce the concentration of mixed samples with greater than 90% accuracy, this device can be considered successful in a lab setting. Subsequently, it is possible to replicate these results in sterile, simulated saliva and if greater than 90% quantification accuracy is reported the device can be considered a candidate tool in a clinical setting.

In some embodiments, tests with human saliva can be carried out, initially using sterile saliva and spiking with known concentrations of markers and then moving to use saliva samples collected by physicians and comparing marker profiles with patient prognosis. Subsequently, the detection can be automated rather than using manual microscope manipulation. This can be accomplished, for example, by making optical alignment marks to ensure the correct start point and then moving the optical stage in a serpentine pattern to take 5-10 data points from each differently sensitized area. For example, for a large 25 marker panel, with 5 data points per marker, and 5 seconds collection time, the entire chip can be read in just over 10 minutes.

In some embodiments, SERS sensors with functionalized nano-bulb chips can be integrated with commercially available hand-held Raman spectrometers. For example, these sensors can be used for bulk analysis of chemical samples for law enforcement or pharmaceutical applications. To compensate for the inefficiencies of Raman spectroscopy and the lack of focusing objectives these devices can be equipped with 500 mW lasers.

Figure 26:
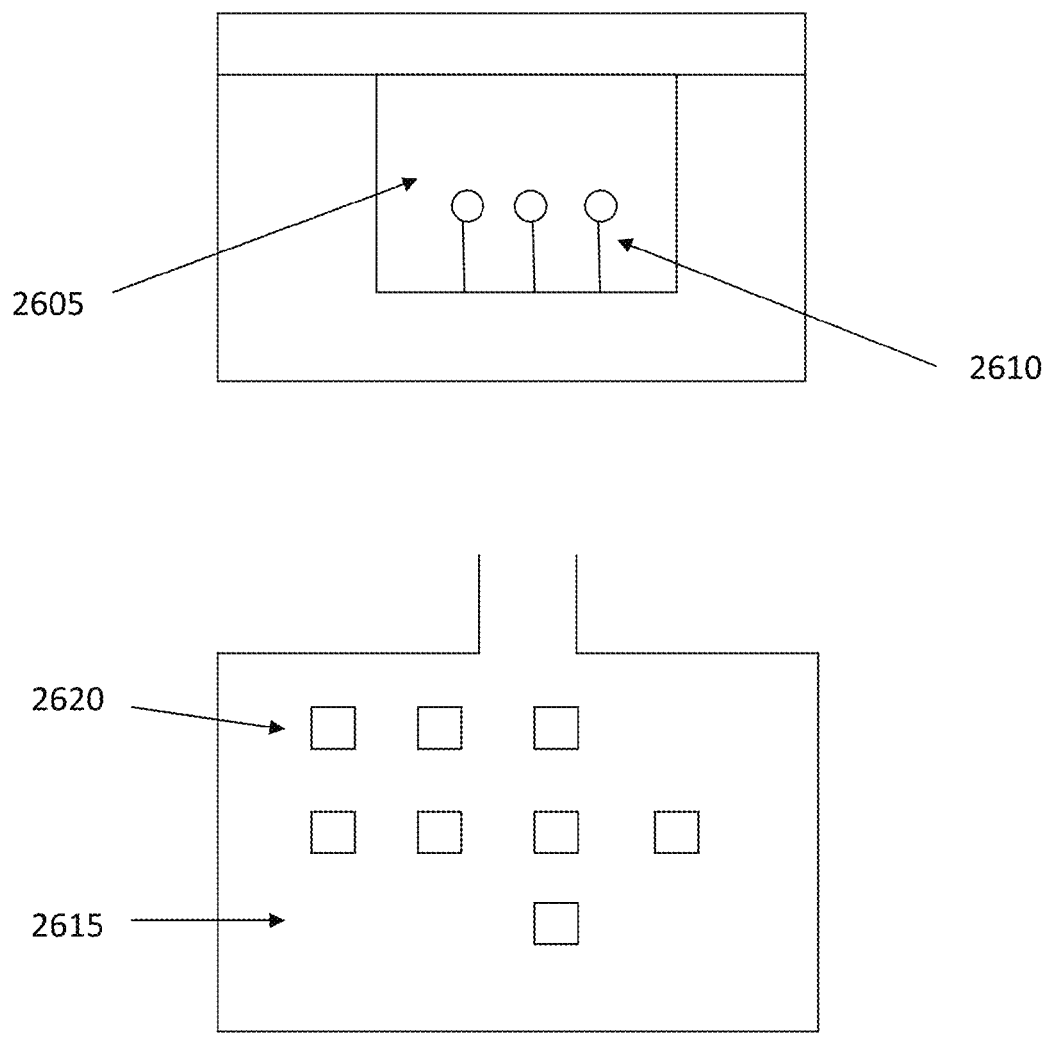
FIG. 26 illustrates an array of sensors.

In some embodiments, a single chip SERS cartridge with the nano-bulbs can be integrated in a hard microfluidic chamber. For example, the sensor can comprise a microfluidic chamber as illustrated in FIG. 26. For example, a chamber (2605) can be filled with liquid and can comprise nanopillars with bulbed metal (2610). A microfluidic chamber (2615) can comprise multiple sensors (2620). Silicon etching techniques can be used to create a 50 micron deep chamber into which it is possible to pattern the nano-bulbs. In some embodiments, the chamber can feature input and output ports for loading or extracting fluid samples and be sealed with a thin glass slide for optical access as in FIG. 26. Multiplexed sensitization can be carried out prior to sealing or after sealing with the introduction of probes through the input and output ports.

In order to create a device that can probe samples in opaque media or perform disease detection in the body, the nano-bulb sensor can be placed on the tip of an optic fiber. In some embodiments, the gold layer, which is normally present due to the fabrication process on the flat surface in between the nanopillars, can be removed in order to be able to etch a window in the silicon substrate and suspend the nanopillar bulbs. The resulting chip can be placed on a jig and a 50 micron core, multimode fiber can be pushed through the membrane, picking it up (with the nano-bulbs) on the end. Van der Waals forces can keep the membrane/bulbs attached, however vapor phase glues can also be used on the tip of the fiber prior to attachment. Multiplexed sensitization of the bulbs can be done prior to attachment or single-probe functionalization can occur after placement on the fiber. SERS excitation and collection can be performed through the fiber itself. Since most of the 500 nm tall bulbs sit well within the near-field acceptance angle of the 50 micron fiber core this process can be quite efficient.

By attaching the nano-bulbs to, for example, a 150 micron wide fiber the entire assembly can be threaded into a 27-30 gauge needle for intravenous measurements. Such a device could be used to monitor the blood during critical care and extract information such as clotting factor concentration during anticoagulant administration in case of a stroke or infarction.

Figure 27:
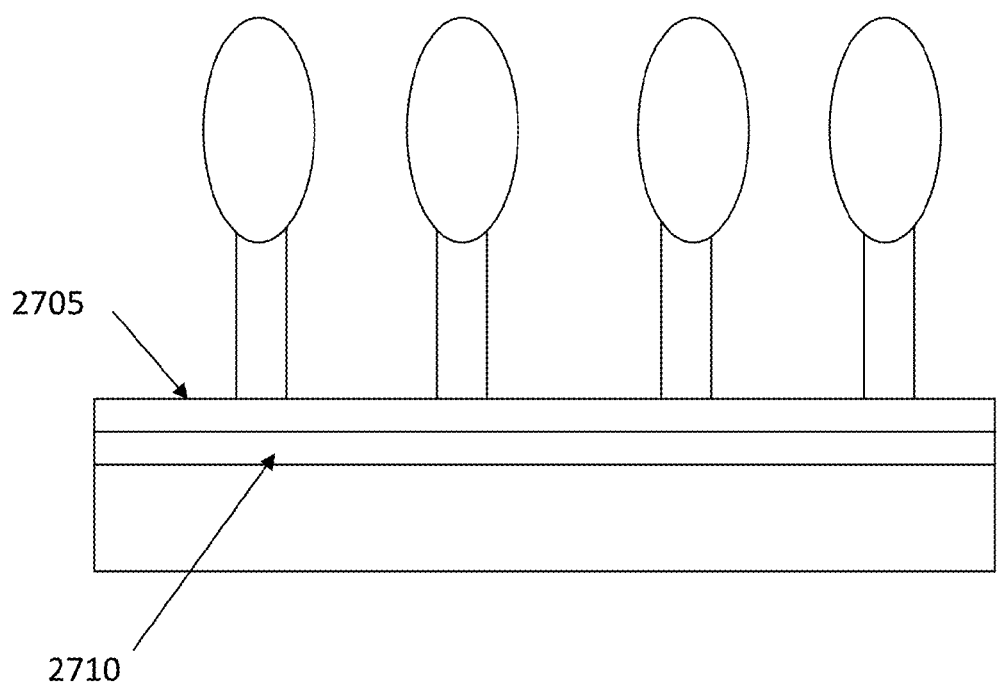
FIG. 27 illustrates an example of nanopillars with bulbs.

In some embodiments, the nanopillars with a beaded metallic layer described in the present disclosure can be fabricated according to the following methods. For example, silicon nanopillars can be etched as described above in the present disclosure, for example according to Reference [4]. The pillars can be oxidized, as for example in step (C) of FIG. 1. Subsequently, gold can be sputtered on the nanopillars, for example as in step (D) of FIG. 1. Gold can then be reflowed by heating, for example at 675° C. Gold's poor adhesion to silicon oxide combined with its surface tension in liquid form causes the gold to bead on top of the silicon oxide nanopillars. The nanopillars are therefore electrically insulated due to the absence of gold on the middle portion of the nanopillars, as visible for example in step (E) of FIG. 1. The nanopillars are therefore electrically insulated between each other and the substrate. By tuning the pillar spacing and gold thickness, nanometer gaps between bulbs can be uniformly formed across large areas of nanopillars. Repeatability can be ensured by use of top-down fabrication techniques to define the pillar spacing and metal thickness. A thin polymer (2705) can be spun on to passivate the remaining gold surface (2710), as illustrated in FIG. 27. Excess polymer can be removed from the bulbs prior to functionalization with an oxygen plasma.

In some embodiments, the devices of the present disclosure can be used to detect chemical compounds, for example hydrogen sulfide ($H_2S$). Hydrogen sulfide is a naturally occurring molecule that can be found in high concentrations in natural gas, crude oil, volcanos and hot springs. In these cases $H_2S$ is formed from the hydrolysis of minerals containing sulfur. It can also be found in swamps and wells formed by the anaerobic breakdown of organic matter by bacteria. In either case the resulting $H_2S$ is heavier than air and tends to pool in high concentration within low lying areas with poor ventilation. $H_2S$ has a wide flammability range (about 4-45%) and is quick to explode in places like mines or drill shafts. In addition $H_2S$ is highly toxic to humans: at high levels (>500-1000 ppm) it can be almost instantly fatal; at levels above 300 ppm it shuts down mitochondria and prevents cellular respiration as well as causing pulmonary edema; above 100 ppm it shuts down the olfactory nerve preventing detection by smell and can cause irreparable eye damage; chronic exposure to lower concentrations (<2 ppm) has been associated with fatigue, nausea, headaches, irritability, dizziness, and an increased risk of miscarriage.

The present disclosure describes a method for detecting $H_2S$ at the above injurious ppm range as well as in much lower concentrations such as the single digit ppb range. This can serve as a preventative indicator for pockets of $H_2S$ as well as an 'early warning' for exposure.

The sensors for hydrogen sulfide can rely on the use of Raman vibrational spectroscopy. In this method laser photons directed at a molecule return after donating a small fraction of their energy (and thus moving to a lower wavelength) to vibrational modes. These modes and their corresponding change in photon energy are unique to types of chemical bonds and elements; thus by examining multiple shifted photons it can be possible to determine the bonding and chemical makeup of a molecule, and therefore identify it. As such the Raman spectrum has been called a "chemical footprint." As described above, standard Raman measurements can be very inefficient; roughly 1 in 10 million photons bounced off a molecule will scatter after donating energy. Therefore powerful lasers, intricate detectors, long collection times and high concentrations of sample molecule are normally required. These characteristics can prevent any sort of construction of a scalable and portable, 'in-field' Raman system that can analyze samples at ppm/ppb concentrations.

As described in the present disclosure, by taking advantage of the unique properties of gaps between adjacent gold particles, a method can be carried out that amplifies the Raman signal by over 1 billion. This is known as surface enhanced Raman spectroscopy. The SERS substrates can be fabricated using top-down lithography as described above, obtaining electrically isolated bulbs atop the pillars with, for example, less than 10 nm gaps between them.

The gold reflow process to form the bulbs, can, in some embodiments, be tuned to provide gaps that are resonant at several popular wavelengths corresponding to portable diode or gas lasers. For example, 488, 514, 633, 790, and 1050 nm can be used. Other wavelengths can also be used, for example with lasers tuned deeper in the UV or Near-IR as well.

The method described herein comprises allowing the $H_2S$ to pass over the SERS substrate, where it can form a uniquely strong Au—S bond while releasing a hydrogen atom resulting in an Au—S—H bonding configuration. After some time 10% of these adsorbed molecules can release the second hydrogen resulting in an Au—S bonding configuration, as described in Reference [41]. Both the S—H and the Au—S bond give unique peaks in a Raman spectrum.

Figure 28:
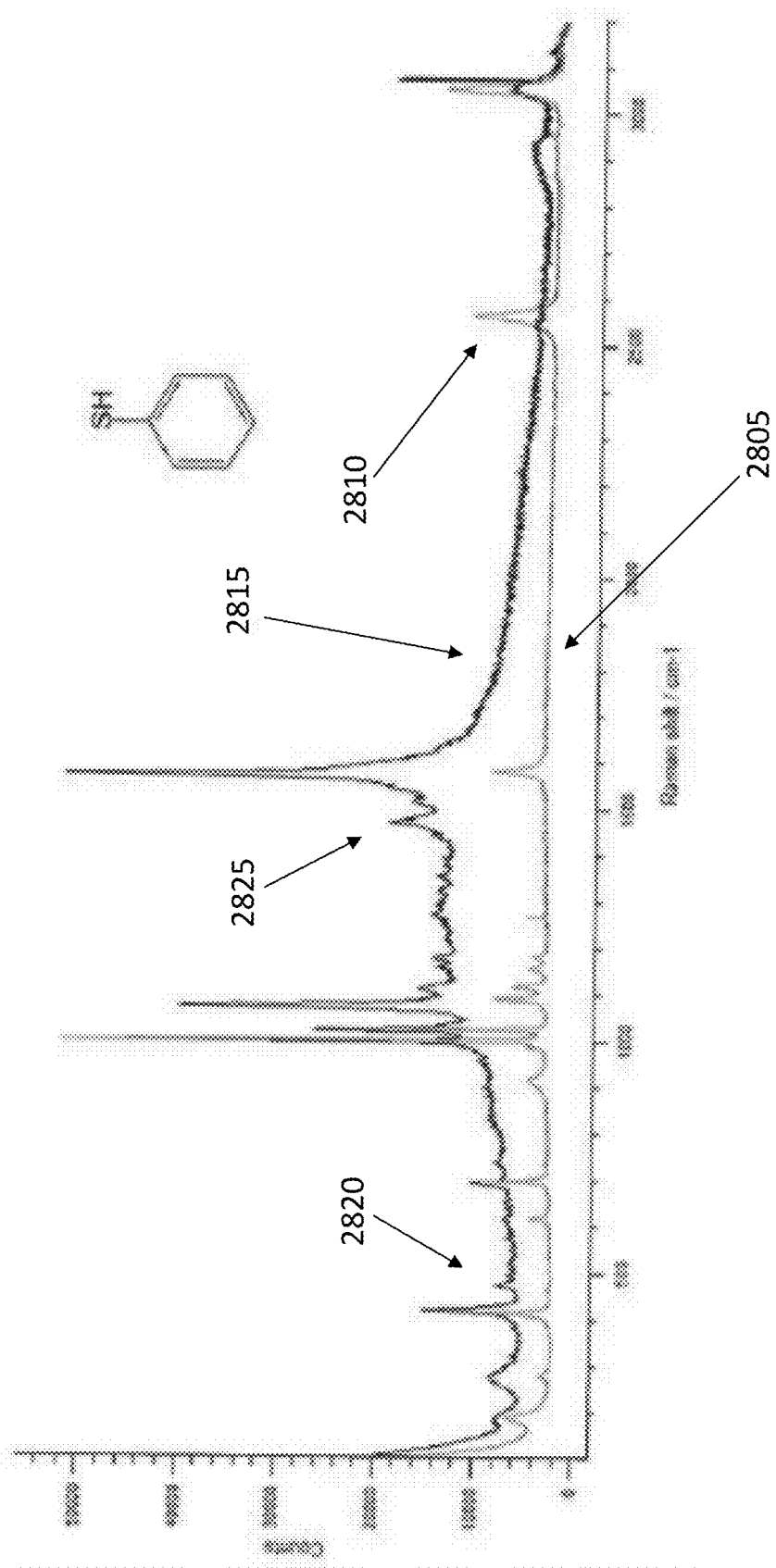
FIG. 28 illustrates detection of hydrogen sulfide.

FIG. 28 illustrates two spectra of the thiophenol molecule. One curve (2805) is a spectrum of a high concentration of thiophenol in solution prior to adsorption—the peak corresponding to the S—H stretch can be easily seen (2810) at approximately 2575 $cm^{-1}$. The other curve (2815) is a measurement of a single monolayer of thiophenol adsorbed on the gold. The S—H stretch peak disappears due to the donation of the H in providing the Au—S bond. However it is possible to see peaks at 490 $cm^{-1}$ (2820) and 1475 $cm^{-1}$ (2825) corresponding to the Au—S bond. The rest of the peaks remain similar across both spectra (2805, 2815) and correspond to modes of the carbon ring and S—C bond. In the case with the Au—S—H complex formation it is possible to see both sets of peaks corresponding to Au—S and S—H with the added benefit of no other bonding features to discriminate against. Utilizing the billion fold increase in Raman signal associated with the SERS chip it is possible to see single molecules adsorbed onto the surface of the gold nanostructures—as a result it is possible to see miniscule concentrations of $H_2S$ adsorbed onto the surface, even at concentrations lower than the ppb range.

This method can be replicated using Cu, Al, Pt, Ni and Ag as the metal of choice, instead of Au, and is applicable to any gas, liquid, or particulate that can be adsorbed onto the surface or that the surface can be immersed in. Each metal used can have a unique set of gas/liquid adsorption affinities (such as CI with Al/Ag, $H_2$ with Pt). In some embodiments, introduction of gas/liquid/particulate can be carried out through ambient air means; microchannels and/or specific molecule/atom permeable membranes can be used in the sensors; spiking the chip with a known concentration of a calibration molecule and comparing the relative intensities of the peaks to extract the concentration can be applied; use of two or more identical enhancement structures in proximity to serve as methods of calibration or to perform differential measurements can be carried out; the use of on-chip light sources, detectors, and other optical components (eg., Resonators, waveguides etc.) may also be useful; the use of the chip in coordination with a hand-held Raman spectroscopy system is possible; the use of the chip in coordination with a fiber (attached in front of or on the tip of) can be carried out; the use of the chip in coordination with a microscope based Raman system can be carried out; the disposable use of chips may be advantageous; the integration of the chip into a badge or portable warning/measurement system can be carried out; the use of functionalization of particles/liquid/gas with tags to aid in Raman detection can be carried out; mass production of chips using CMOS foundries can be carried out; use of methods other than sputtering for the application of metals can be carried out; the use of other substrates than silicon can be carried out; the use of other methods than etching and lithography to fabricate pillars of material can be carried out; the attachment of the chip to remote probes with fiber coupling to a Raman spectrometer can be carried out; the use of a non-regular array of structures to provide unique optical effects to affect the Raman signal can be carried out; methods such as but not limited to oxygen plasma or $H_2SO_4/H_2O_2$ to clean and reuse the sensing chip can be carried out; methods of making the chip out of biocompatible materials so it can be implanted or digested can be carried out.

In the following an example is described on the detection of a gas in very low concentrations with the devices of the present disclosure. The test was carried out with gas used in camping applications. A typical composition for camping gas is propane adulterated with 17 ppm of ethyl-mercaptan (EM). The sensing chip was exposed to the vented gas from a distance of a few inches. Although in the bottle the EM is at 17 ppm, when vented to the air the concentration drops significantly, for example to about 5 ppm of EM diluted in propane and air.

Figure 29:
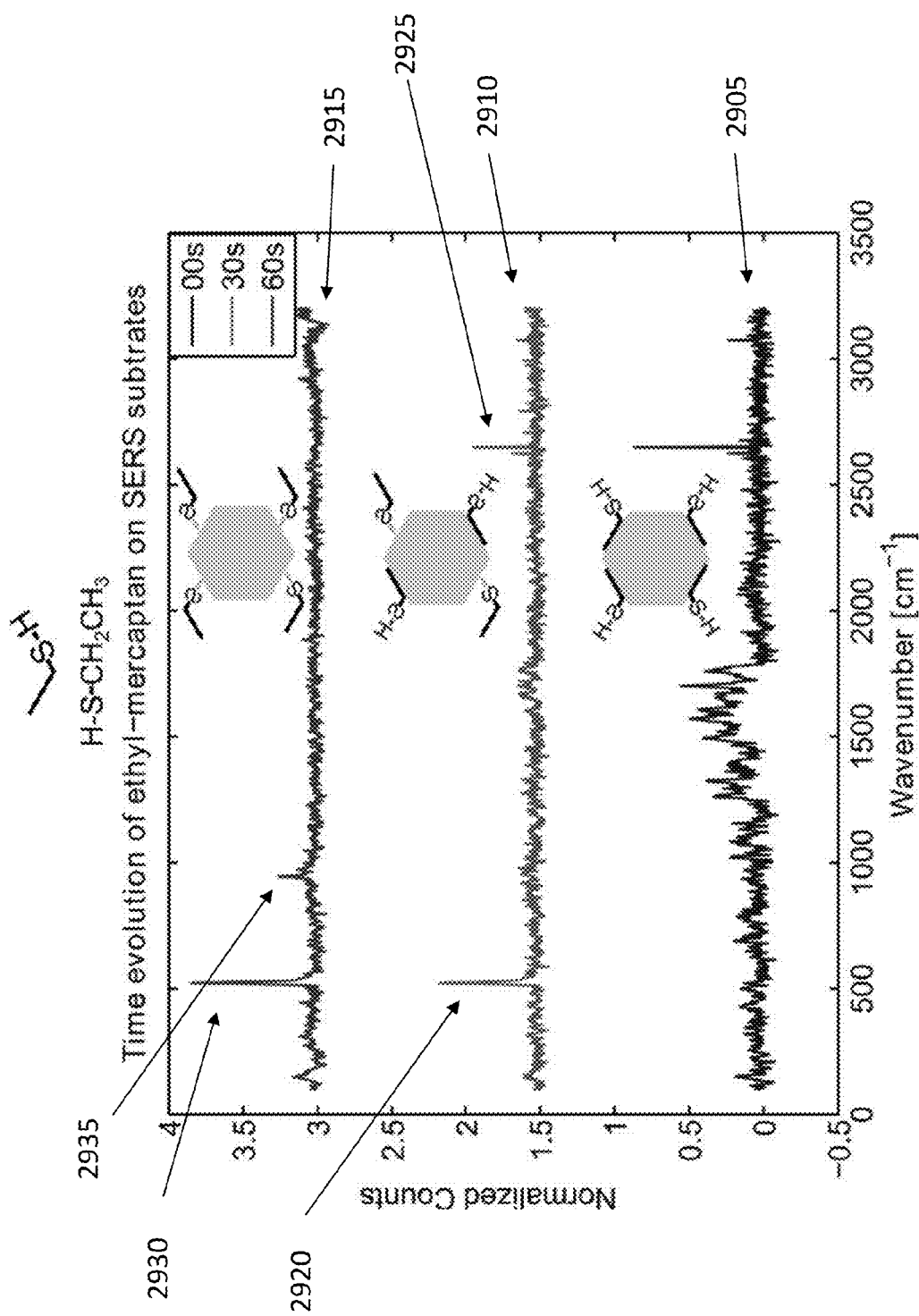
FIG. 29 illustrates detection of ethil-mercaptan.

Samples were measured for 10 s at 50 microW of power using a 633 nm laser. The data immediately after exposure is visible in FIG. 29 (2905) and shows a huge H—S bond-stretch signal at 2650 $cm^{-1}$ as well as some small propane related signals. This comes from physically adsorbed EM molecules. The data in FIG. 29 is plotted at zero seconds (2905), 30 s (2910) and 60 s (2915).

When measured 30 s after exposure (2910) it was evident that some of the physically adsorbed EM had donated a hydrogen and covalently bonded to the gold. This gave two key peaks—one at 525 $cm^{-1}$ (Au—S, 2920) and one at 2600 $cm^{-1}$ (S—H, 2925). Therefore, a portion of the population was physiabsorbed and a portion chemiabsorbed.

When measured after a minute (2915) it was found that all of the physically adsorbed EM had covalently bonded and given up its hydrogen, leaving only an Au—S stretch signal at 525 $cm^{-1}$ (2930). A signal was also visible at 945 cm (2935) which corresponds to a C—C stretch of the ethane that only becomes prominent when the molecules are aligned with an Au—S—C—C configuration perpendicular to the gold surface. The reason is that the dipole of the vibrational mode is well aligned with the bound electric field of the laser light.

This is a first demonstration of measuring an $H_2S$ analog gas at low concentrations. Based on the large signal to noise from this simple measurement it can be estimated that an LOD can be several orders of magnitude less than what measured in FIG. 29. This LOD is well past the requirements of an $H_2S$ sensor required for oil-field applications.

In some embodiments, in order to create a "stand-off" or remote sensor, nano-bulb surface enhanced Raman substrates (SERS) can be applied onto the ends of fibers. In the following, an embodiment of a method of fabrication for the fiber-tip sensor mounting process is described. In this embodiment a chip was used with a triangular shaped area of SERS enhancement pillars. The triangular area is shown (3005) in FIG. 30 in an optical image (3007) and a zoomed in SEM image of the pillars (250 nm center to center spacing, 3010).

Figure 30:
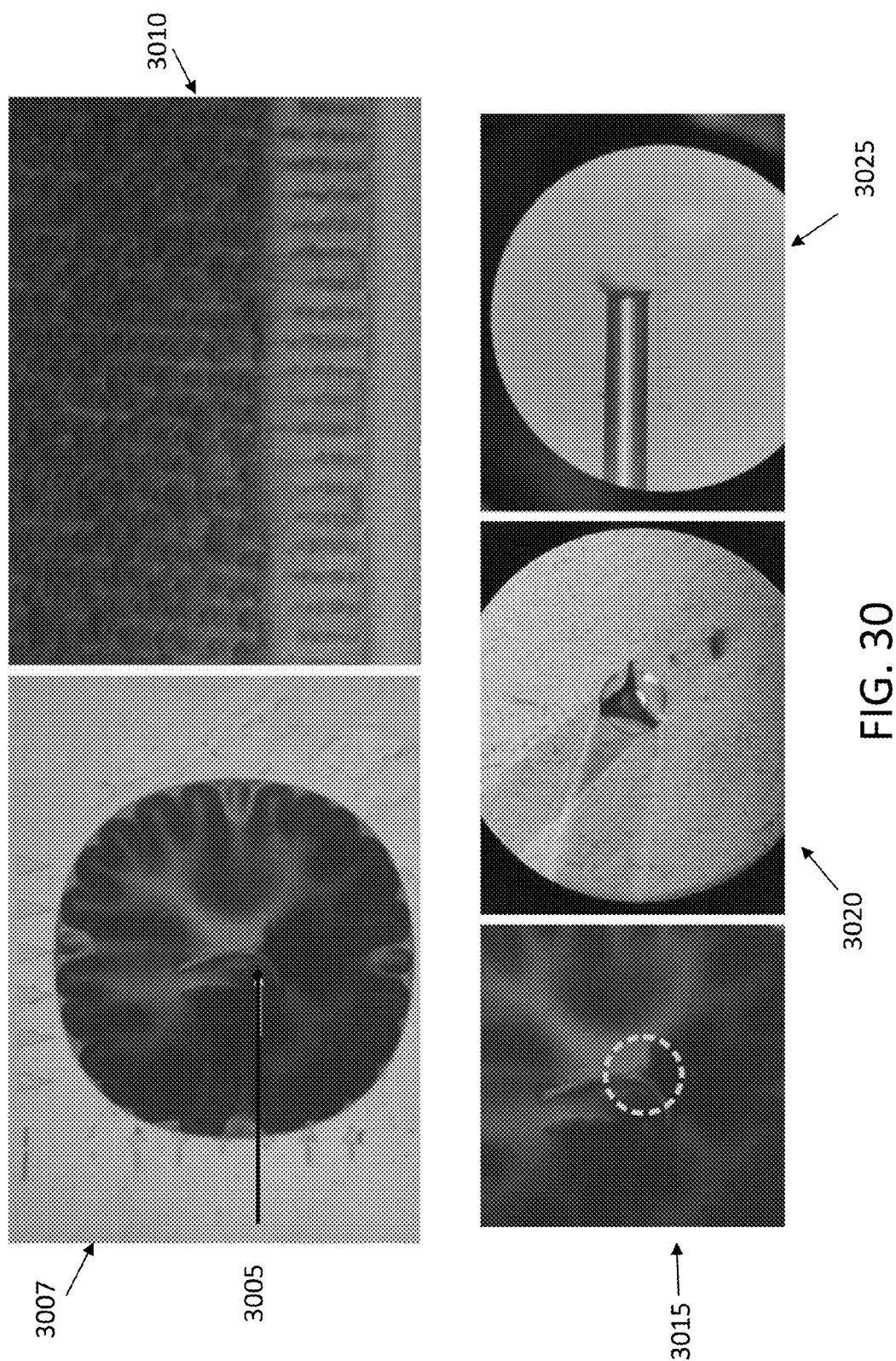
FIGS. 30-31 illustrate methods of attaching nanopillars to an optic fiber.

In the optical image (3007) the dark circle is the area of the hole etched through the silicon substrate and the T-shaped region is the location of the pillars. In FIG. 30, image (3015) shows the area that will be lifted off by the fiber. Image (3020) shows a top-down view of the fiber-cladding and fiber-core after lifting off the triangular region. Image (3025) shows the side-view of the fiber after membrane attachment.

Figure 31:
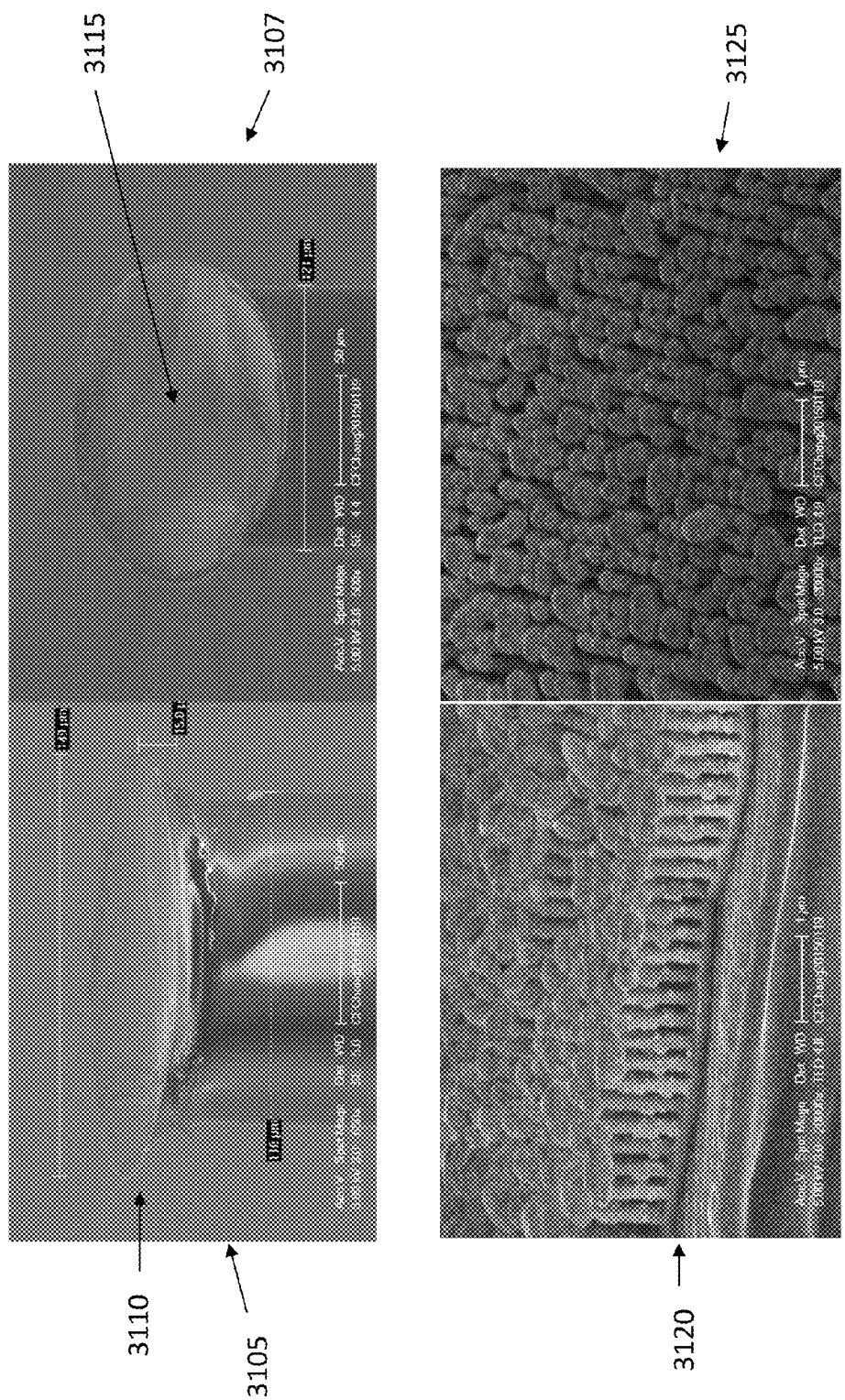

The fiber was then ashed in an oxygen plasma to remove the PMMA stabilization layer. The two SEM images (3105, 3107) in FIG. 31 show the fiber-sensor after oxygen plasma treatment. From the side view (3105) it is possible to see the layer (3110) of index matched, UV-cured epoxy used to stick the membrane to the fiber. The 45° view (3107) clearly shows the triangular nanobulb area (3115). FIG. 31 also illustrates two closer images (3120, 3125) of the nanobulbs after attachment. It is possible to see that the nanopillars have remained unchanged after transfer to the optic fiber as described above in the present disclosure. The spacing, quality and density are consistent before and after fiber mounting.

Figure 32:
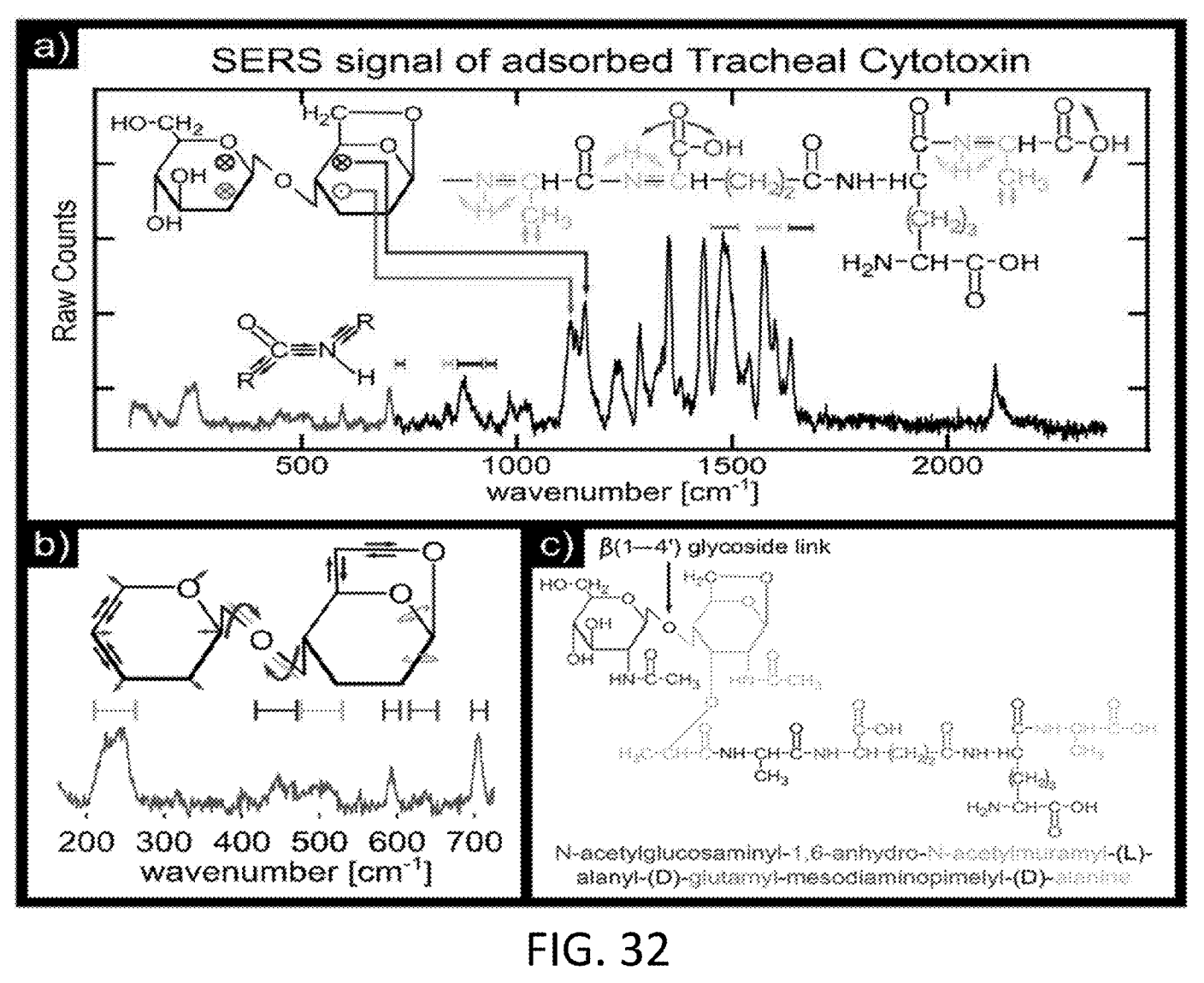
Figure 33:
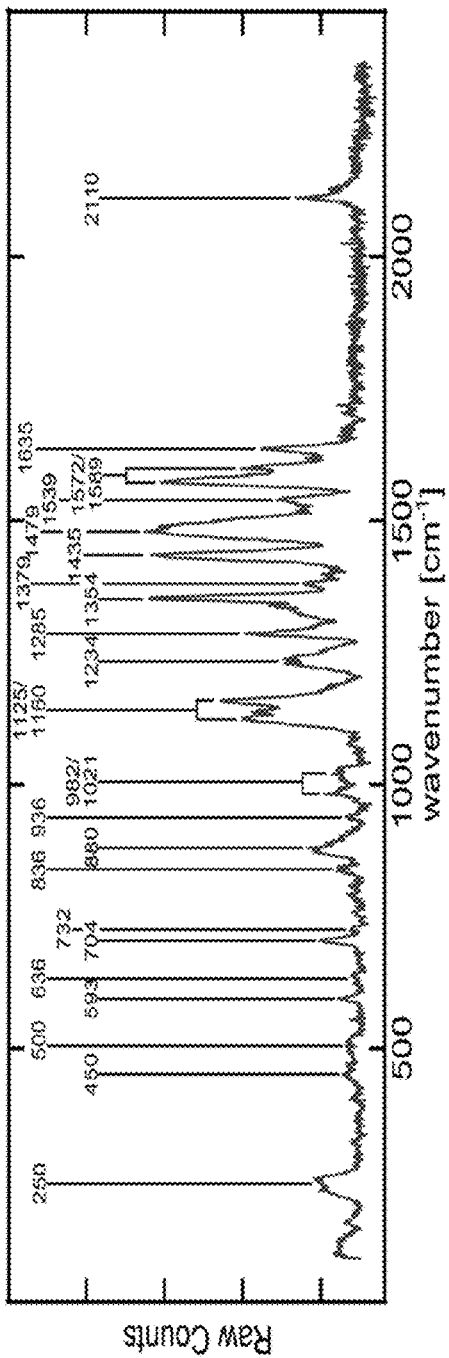
Figure 34:
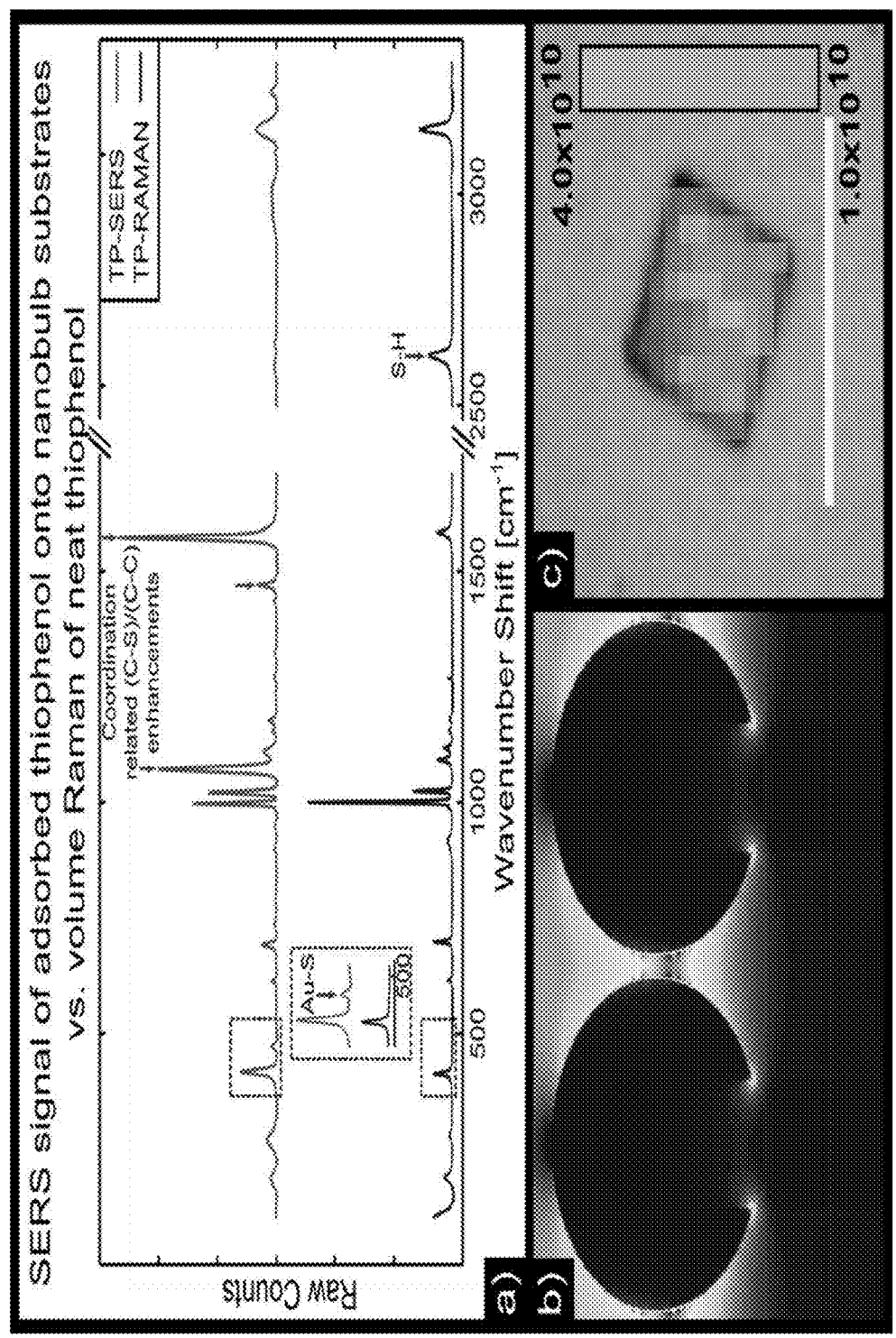

FIGS. 32-34 illustrate data on thiophenol experiments.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The present disclosure includes a References section below. The disclosures of all the references are incorporated by reference in their entirety.

LIST OF REFERENCES

[1] S. Walavalkar et al., "Scalable Method for the Fabrication and Testing of Glass-Filled, Three-Dimensionally Sculpted Extraordinary Transmission Apertures," *Nano Lett.* 14 (1), pp. 311-317 (2014).

[2] I. Barman et al., "Accurate Spectroscopic Calibration for Noninvasive Glucose Monitoring by Modeling the Physiological Glucose Dynamics," *Anal. Chem.* 82, pp. 6104-6114 (2010).

[3] Henry, M. D., et al., Alumina etch masks for the fabrication of high-aspect-ratio silicon micropillars and nanopillars. Nanotechnology, 2009. 20.

[4] Walavalkar, S. S., et al., Controllable deformation of silicon nanowires with strain up to 24%. Journal of Applied Physics, 2010. 107: p. 124314.

[5] Walavalkar, S. S., et al., Tunable visible and near-IR emission from sub-10 nm etched single crystal Si nanopillars. Nano Letters, 2010. 10: p. 4423-4428.

[6] Walavalkar, S. S., et al., Size tunable visible and near-infrared photoluminescence from vertically etched silicon quantum dots. Applied Physics Letters, 2011. 98: p. 153114-153117.

[7] Walavalkar, S. S., et al., Three-dimensional etching of silicon for the fabrication of low-dimensional and suspended devices. Nanoscale, 2013. 5: p. 927-931.

[8] Walavalkar, S. S., P. Latawiec, and A. Scherer, Coulomb blockade in vertical, bandgap engineered silicon nanopillars. Applied Physics Letters, 2013. 102: p. 183101-183104.

[9] Walavalkar, S. S., et al., Scalable method for the fabrication and testing of glass-filled, three-dimensionally sculpted extraordinary transmission apertures. Nano letters, 2014. 14: p. 311-7.

[10] Wulfkuhle, J. D., L. A. Liotta, and E. F. Petricoin, Proteomic applications for the early detection of cancer. Nature reviews. Cancer, 2003. 3: p. 267-75.

[11] Dalby, T. and K. A. Krogfelt, Laboratory diagnosis of pertussis: agglutination is not suitable. Respirology (Carlton, Vic.), 2011. 16: p. 1160-2.

[12] Campbell, H., et al., Oral fluid testing for pertussis, England and wales, June 2007-August 2009. Emerging infectious diseases, 2014. 20: p. 968-75.

[13] Rasooly, A. and J. Jacobson, Development of biosensors for cancer clinical testing. Biosensors & bioelectronics, 2006. 21: p. 1851-8.

[14] Soper, S. A., et al., Point-of-care biosensor systems for cancer diagnostics/prognostics. Biosensors & bioelectronics, 2006. 21: p. 1932-42.

[15] Wang, J., Electrochemical biosensors: towards point-of-care cancer diagnostics. Biosensors & bioelectronics, 2006. 21: p. 1887-92.

[16] Wei, F., et al., Electrochemical sensor for multiplex biomarkers detection. Clinical cancer research: an official journal of the American Association for Cancer Research, 2009. 15: p. 4446-52.

[17] Tothill, I. E., Biosensors for cancer markers diagnosis. Seminars in cell & developmental biology, 2009. 20: p. 55-62.

[18] Lozano, R., et al., Global and regional mortality from 235 causes of death for 20 age groups in 1990 and 2010: a systematic analysis for the Global Burden of Disease Study 2010. Lancet, 2012. 380: p. 2095-128.

[19] Howlader N, N. A., Krapcho M, Garshell J, Miller D, Altekruse S F, Kosary C L, Yu M, Ruhl J, Tatalovich Z, Mariotto A, Lewis D R, Chen H S, Feuer E J, Cronin K A (eds), SEER Cancer Statistics Review, 1975-2011, 2014: National Cancer Institute. Bethesda, Md.

[20] Shah, F. D., et al., A review on salivary genomics and proteomics biomarkers in oral cancer. Indian journal of clinical biochemistry: IJCB, 2011. 26: p. 326-34.

[21] Punyani, S. R. and R. S. Sathawane, Salivary level of interleukin-8 in oral precancer and oral squamous cell carcinoma. Clinical oral investigations, 2013. 17: p. 517-24.

[22] Cheng, Y.-S. L., T. Rees, and J. Wright, A review of research on salivary biomarkers for oral cancer detection. Clinical and translational medicine, 2014. 3: p. 3.

[23] Tondella, M. L., et al., International *Bordetella pertussis* assay standardization and harmonization meeting report. Centers for Disease Control and Prevention, Atlanta, Ga., United States, 19-20 July 2007. Vaccine, 2009. 27: p. 803-14.

[24] Melvin, J. A., et al., *Bordetella pertussis* pathogenesis: current and future challenges. Nature reviews. Microbiology, 2014. 12: p. 274-88.

[25] Atwell, J. E., et al., Nonmedical vaccine exemptions and pertussis in California, 2010. Pediatrics, 2013. 132: p. 624-30.

[26] Locht, C., Molecular aspects of *Bordetella pertussis* pathogenesis, in International Microbiology. p. 137-144.

[27] de Gouw, D., et al., Pertussis: a matter of immune modulation. FEMS microbiology reviews, 2011. 35: p. 441-74.

[28] Shembekar, V. R., et al., A protecting group for carboxylic acids that can be photolyzed by visible light. Biochemistry, 2005. 44: p. 7107-14

[29] Kumar, S., J. Aaron, and K. Sokolov, Directional conjugation of antibodies to nanoparticles for synthesis of multiplexed optical contrast agents with both delivery and targeting moieties. Nature protocols, 2008. 3: p. 314-20.

[30] Li, Y., et al., Salivary transcriptome diagnostics for oral cancer detection. Clinical cancer research: an official journal of the American Association for Cancer Research, 2004. 10: p. 8442-50.

[31] Sung, H. J., et al., Inhibition of human neutrophil activity by an RNA aptamer bound to interleukin-8. Biomaterials, 2014. 35: p. 578-89.

[32] Ellington, A. D. and J. W. Szostak, In vitro selection of RNA molecules that bind specific ligands. Nature, 1990. 346: p. 818-22.

[33] Hamaguchi, N., A. Ellington, and M. Stanton, Aptamer beacons for the direct detection of proteins. Analytical biochemistry, 2001. 294: p. 126-31.

[34] Roberts, R. W. and J. W. Szostak, RNA-peptide fusions for the in vitro selection of peptides and proteins. Proceedings of the National Academy of Sciences, 1997. 94: p. 12297-12302.

[35] Takahashi, T. T., R. J. Austin, and R. W. Roberts, mRNA display: ligand discovery, interaction analysis and beyond. Trends in biochemical sciences, 2003. 28: p. 159-65.

[36] Wilson, D. S., A. D. Keefe, and J. W. Szostak, The use of mRNA display to select high-affinity protein-binding peptides. Proceedings of the National Academy of Sciences of the United States of America, 2001. 98: p. 3750-5.

[37] Aoyama, T., et al., Comparison of blood-free medium (cyclodextrin solid medium) with Bordet-Gengou medium for clinical isolation of *Bordetella pertussis*. J. Clin. Microbiol., 1986. 23: p. 1046-1048.

[38] Yang, X., et al., Construction and selection of bead-bound combinatorial oligonucleoside phosphorothioate and phosphorodithioate aptamer libraries designed for rapid PCR-based sequencing. Nucleic acids research, 2002. 30: p. e132.

[39] Goldman, W. E., D. G. Klapper, and J. B. Baseman, Detection, isolation, and analysis of a released *Bordetella pertussis* product toxic to cultured tracheal cells. Infect. Immun., 1982. 36: p. 782-794.

[40] Rosenthal, R. S., et al., Major fragment of soluble peptidoglycan released from growing *Bordetella pertussis* is tracheal cytotoxin. Infect. Immun., 1987. 55: p. 2117-2120.

[41] Andrew J. Leavitt, T. P. B., *Chemical reactive studies of hydrogen sulfide on Au*(111). Surface Science, 1994. 314: p. 22-33.

What is claimed is:

1. A method comprising:
providing a substrate;
defining at least one recessed region in the substrate;
forming nanopillars in the at least one recessed region;
depositing a metallic layer on a top end of the nanopillars and between the nanopillars in the at least one recessed region, the metallic layer being continuous throughout the top end of the nanopillars and between the nanopillars;
by heating the metallic layer, reflowing the metallic layer on the top end of the nanopillars while removing the metallic layer from a middle portion of the nanopillars, thereby forming metallic bulbs on the top end of the nanopillars; and
functionalizing the metallic bulbs on the top end of the nanopillars.

2. The method of claim 1, further comprising:
defining at least one blank region in the substrate, the at least one blank region being at least one recessed region void of nanopillars; and
depositing a metallic layer on the at least one blank region.

3. The method of claim 1, wherein forming nanopillars and reflowing the metallic layer comprise forming a distance between the metallic bulbs between 5 and 50 nanometers.

4. The method of claim 1, further comprising attaching an imaging device to the substrate on a surface opposite to a surface where the nanopillars are formed.

5. The method of claim 4, wherein the imaging device is a wirelessly-powered complementary metal-oxide semiconductor (CMOS) device, configured to transmit images wirelessly to a receiver.

6. The method of claim 1, wherein the substrate comprises mesas having a height higher than the at least one recessed region on the substrate, and a height of the nanopillars is equal or less than the height of the mesas.

7. The method of claim 1, wherein:
defining at least one recessed region comprises defining an array of recessed regions in the substrate, and
forming nanopillars comprises forming nanopillars in each recessed region of the array of recessed regions.

8. The method of claim 7, wherein forming nanopillars in each recessed region of the array of recessed regions comprises forming nanopillars with at least a first nanopillar shape in at least one recessed regions of the array of recessed regions, and forming nanopillars with at least a second nanopillar shape in at least one recessed regions of the array of recessed regions.

9. The method of claim 7, wherein functionalizing the metallic bulbs comprises using a different functionalizing agent for at least two regions of the array of recessed regions.

10. The method of claim 7, wherein the array of recessed regions is a square array and each corner region of the square array of recessed regions is functionalized with thiol groups.

11. The method of claim 1, further comprising implanting the sensor in human tissue.

12. The method of claim 1, wherein a spacing between the metallic bulbs allows electrical insulation between the metallic bulbs.

13. The method of claim 1, wherein the substrate is silicon, the nanopillars are silicon dioxide and the metallic layer is gold.

14. The method of claim 1, further comprising attaching an optical fiber to one end of the at least one recessed region, wherein an opposite wall of the at least one recessed region comprises a metallic layer, thereby acting as a reflector for the optical fiber, the optical fiber being configured to shine a laser light on the metallic bulbs and collect a signal reflected from the metallic bulbs.

15. The method of claim 1, further comprising, after forming nanopillars and prior to depositing a metallic layer, oxidizing the nanopillars.

16. The method of claim 1, wherein:
defining at least one recessed region comprises etching the substrate; and
forming nanopillars comprises etching the at least one recessed region; and depositing a metallic layer comprises sputtering the metallic layer.

17. The method of claim 1, further comprising applying a polymer layer on a top surface of the at least one recessed region in between the nanopillars.

18. The method of claim 1, wherein forming nanopillars comprises spacing the nanopillars and the metallic bulbs at a distance based on a desired resonant wavelength.

19. The method of claim 1, wherein heating the metallic layer is at 675° C.

20. The method of claim 1, further comprising, after defining at least one recessed region and prior to forming nanopillars, forming mesas in the substrate and oxidizing the mesas.

21. The method of claim 1, wherein functionalizing the metallic bulbs comprises applying one or more functionalizing agents on the metallic bulbs on the top end of the nanopillars.

22. The method of claim 21, wherein the one or more functionalizing agents is a nucleic acid aptamer.

23. The method of claim 21, wherein the one or more functionalizing agents comprise an antibody.

24. The method of claim 21, wherein the one or more functionalizing agents comprise cDNA.

25. The method of claim 21, wherein the one or more functionalizing agents comprise two or more different functionalizing agents.

26. The method of claim 21, wherein the one or more functionalizing agents specifically bind to one or more biomolecules.

27. The method of claim 26, wherein said binding is reversible.

28. The method of claim 26, wherein at least one of the one or more biomolecules is a protein.

29. The method of claim 26, wherein at least one of the one or more biomolecules is an mRNA.

30. The method of claim 26, wherein at least one of the one or more biomolecules is a cytokine.

31. The method of claim 26, wherein the one or more biomolecules comprise a molecular marker of disease.

32. The method of claim 31, wherein the disease is oral cancer.

33. The method of claim 31, wherein the disease is whooping cough.

34. The method of claim 26, wherein the one or more biomolecules comprise tracheal cytotoxin.

35. The method of claim 26, wherein the one or more biomolecules comprise thrombin.

36. A method comprising:
providing a substrate;
etching at least one recessed region in the substrate;
etching at least one groove on a surface of the at least one recessed region;
forming nanopillars in the at least one recessed region close to but not within the groove;
depositing a metallic layer on a top end of the nanopillars, on a side surface of the at least one recessed region, and between the nanopillars in the at least one recessed region, the metallic layer being continuous throughout the top end of the nanopillars and between the nanopillars;
by heating the metallic layer, reflowing the metallic layer on the top end of the nanopillars while removing the metallic layer from a middle portion of the nanopillars, thereby forming metallic bulbs on the top end of the nanopillars;
functionalizing the metallic bulbs on the top end of the nanopillars; and
attaching an optic fiber to the groove, the optic fiber having a surface substantially parallel and opposite to the side surface of the at least one recessed region.

37. The method of claim 36, wherein heating the metallic layer is at 675° C.

38. A method comprising:
providing a substrate;
forming nanopillars on the substrate;
depositing a metallic layer on a top end of the nanopillars and between the nanopillars in the at least one recessed region, the metallic layer being continuous throughout the top end of the nanopillars and between the nanopillars;
by heating the metallic layer, reflowing the metallic layer on the top end of the nanopillars while removing the metallic layer from a middle portion of the nanopillars, thereby forming metallic bulbs on the top end of the nanopillars;
functionalizing the metallic bulbs on the top end of the nanopillars;
etching the substrate on a surface opposite the surface with the nanopillars;
inserting an optic fiber in the etched side of the substrate, on the surface opposite the surface with the nanopillars; and
lifting the nanopillars with the optic fiber.

39. The method of claim 38, further comprising inserting the optic fiber with the nanopillars within a needle.

40. The method of claim 38, further comprising applying a layer of glue to a surface of the optic fiber prior to inserting, thereby gluing the nanopillars to the optic fiber when lifting the nanopillars with the optic fiber.

41. The method of claim 38, wherein heating the metallic layer is at 675° C.

* * * * *